(12) United States Patent
Mikami et al.

(10) Patent No.: US 7,473,793 B2
(45) Date of Patent: Jan. 6, 2009

(54) TRANSITION METAL COMPLEX AND PROCESS FOR PRODUCING OPTICALLY ACTIVE ALCOHOL

(75) Inventors: Koichi Mikami, Tokyo (JP); Noburo Sayo, Tokyo (JP)

(73) Assignee: Takasago International Corporation, Tokyo (JP)

( * ) Notice: Subject to any disclaimer, the term of this patent is extended or adjusted under 35 U.S.C. 154(b) by 353 days.

(21) Appl. No.: 11/353,533

(22) Filed: Feb. 13, 2006

(65) Prior Publication Data

US 2006/0142603 A1    Jun. 29, 2006

Related U.S. Application Data

(63) Continuation of application No. PCT/JP2004/011693, filed on Aug. 13, 2004.

(30) Foreign Application Priority Data

Aug. 13, 2003    (JP) .............................. 2003-293145

(51) Int. Cl.
*C07F 15/00* (2006.01)
*C07C 29/14* (2006.01)
(52) U.S. Cl. .............................. 556/18; 568/8; 568/17; 568/881
(58) Field of Classification Search .................. 556/18; 568/8, 17, 881
See application file for complete search history.

(56) References Cited

FOREIGN PATENT DOCUMENTS

| | | |
|---|---|---|
| DE | 102 05 702 A1 | 8/2002 |
| EP | 1 323 724 A2 | 7/2003 |
| JP | 2002-308816 | 10/2002 |
| WO | WO-01/74829 A1 | 10/2001 |

OTHER PUBLICATIONS

Reetz et al., Organic Letters, vol. 3, No. 25, pp. 4083-4085 (2001).*
Doucet et al., "Trans-[RuCI$_2$(phosphane)$_2$(1,2-diamine)] and Chiral trans-[RuCI$_2$(diphosphane)(1,2-diamine)]: Shelf-Stable Precatalysts for the Rapid, Productive, and Stereoselective Hydrogenation of Ketones", Angew. Chem. Int. Ed., vol. 37, No. 12, pp. 1703-1707 (1998).
Kranenburg et al., "New Diphosphine Ligands Based on Heterocyclic Aromatics Inducing Very High Regioselectivity in Rhodium-Catalyzed Hydroformylation: Effect of the Bite Angle", Organometallics, vol. 14, No. 6, pp. 3081-3089 (1995).
Lesueur et al., A Bidentate Bisphosphine Functioning in Intramolecular Aliphatic Metalation and as an NMR Spectroscopic Probe for the Metal Coordination Environment, Inorganic Chemistry, Amer. Chem. Soc., vol. 36, No. 15, pp. 3354-3362 (1997).

* cited by examiner

*Primary Examiner*—Porfirio Nazario Gonzalez
(74) *Attorney, Agent, or Firm*—Peter F. Corless; Christine C. O'Day; Edwards Angell Palmer & Dodge LLP

(57) ABSTRACT

A novel transition metal complex, preferably a ruthenium-phosphine complex or rhodium-phosphine complex, which is effectively usable in various asymmetric syntheses and, in particular, is more effectively usable in the asymmetric hydrogenation of various ketones; and a novel process for producing an optically active alcohol with the complex. The novel transition metal complex includes a ligand obtained by introducing a diarylphosphino group into each of the 2- and 2'-positions of diphenyl ether, benzophenone, benzhydrol, or the like. It preferably further includes an optically active 1,2-diphenylethylenediamine coordinated thereto. The complex preferably is a novel diphosphine-ruthenium-optically active diamine complex or diphosphine-rhodium-optically active diamine complex. The process comprises using the complex as an asymmetric hydrogenation catalyst to conduct the asymmetric hydrogenation of a ketone compound to thereby obtain an optically active alcohol in a high optical purity and a high yield.

12 Claims, No Drawings

TRANSITION METAL COMPLEX AND PROCESS FOR PRODUCING OPTICALLY ACTIVE ALCOHOL

This application is a continuation of International Application PCT/JP2004/011693 having an International filing date of Aug. 13, 2004, which is incorporated herein by reference in its entirety.

TECHNICAL FIELD

The present invention relates to a novel transition metal complex, preferably a ruthenium phosphine complex, or rhodium phosphine complex. In particular, the present invention relates to a transition metal complex, wherein a metal complex having an achiral diphosphine compound as a ligand is coordinated with an optically active diamine derivative, preferably a ruthenium complex or rhodium complex; an asymmetric catalyst comprising the complex; and a process for producing an optically active alcohol by use of the catalyst.

BACKGROUND ART

Hitherto, it has been known to use, as an asymmetric catalyst, a complex comprising a transition metal atom and an organic ligand as its constituents. It has also been known to select an optically active compound as the organic ligand, in particular an axially-asymmetric diphosphine ligand compound. However, the axially-asymmetric diphosphine ligand compound is very expensive in many cases. Thus, the compound is disadvantageous for industrial use.

Consequently, if there is any way an achiral ligand can be used instead of the axially-asymmetric diphosphine ligand compound, the method can be an advantageous method by which an optically active compound can be obtained at low costs.

As an example of asymmetric hydrogenation using such an achiral diphosphine ligand, there is a report wherein 2,2'-bis(diarylphosphino)-1,1'-biphenyl is used (see Non-patent Document 1). This describes an example of asymmetric hydrogenation using a diphosphine-ruthenium-optically active diamine complex. However, the asymmetric yield of the diphosphine-ruthenium-optically active diamine complex described therein is not very high in certain kinds of ketone used as the starting material thereof. The yield does not reach a practical level in some cases.

Non-patent Document 1: K. Mikami et al., Angew, Chem. Int. Ed., vol. 38, 495 (1999).

DISCLOSURE OF THE INVENTION

The present invention has been made in light of the above circumstance, and an object thereof is to provide a novel transition metal complex, such as a ruthenium phosphine complex or rhodium phosphine complex, which can be effectively used for various asymmetric synthesis and can be more effectively in particular for asymmetric hydrogenation of various ketone; and a novel process for producing an optically active alcohol, using the same.

In the middle of eager researches for solving the above-mentioned problems, the inventors have considered that an achiral diphosphine ligand is made into a ruthenium complex and further the complex is coordinated with an optically active diamine ligand, thereby fixing the configuration thereof to make up a pseudo asymmetric environment. In other words, the inventors have considered that if such a configuration can be fixed, this complex can function as an asymmetric complex catalyst and can be applied to asymmetric hydrogenation, and repeated further researches. As a result, the inventors have found out the following: a ligand wherein diarylphosphino groups are introduced into 2,2'-positions of diphenyl ether, benzophenone, benzhydrol or the like is synthesized; this ligand is used to prepare a metal complex of ruthenium, rhodium or the like; this is coordinated with optically active 1,2-diphenylethylenediamine to form a complex which is a diphosphine-ruthenium-optically active diamine complex or diphosphine-rhodium-optically active diamine complex; this is used to hydrogenate ketone compound; consequently, hydrogenation of ketone compound proceeded as expected so that an optically active alcohol is obtained in a high optical purity and a high yield; and a high asymmetric yield is attained in the same manner as attained when an optically pure catalyst is used. Thus, the present invention has been accomplished.

The present invention include the following constitutions (1) to (13):

(1) A transition metal complex represented by the following formula [1]:

$$[LMX_pZ^1{}_n] \quad [1]$$

wherein L represents a compound represented by the formula [2]:

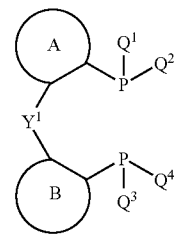

[2]

wherein ring A and ring B each independently represent an aromatic ring which may have a substituent, $Q^1$, $Q^2$, $Q^3$, and $Q^4$ each independently represent an aryl group which may have a substituent or an alicyclic group which may have a substituent, and $Y^1$ represents a spacer; M represents a transition metal; X represents a halogen atom or an anion; $Z^1$ represents a compound represented by the formula [3]:

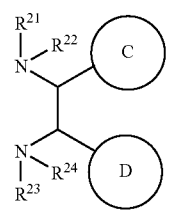

[3]

wherein ring C and ring D each independently represent a phenyl group which may have a substituent or an alicyclic group which may have a substituent, and $R^{21}$, $R^{22}$, $R^{23}$, and $R^{24}$ each independently represent a hydrogen atom or an alkyl group; p represents 1 or 2; and n is a natural number.

(2) The transition metal complex according to (1), wherein $Y^1$ in the compound represented by the formula [2] is a carbonyl group, a sulfonyl group, a thiocarbonyl group, —CH(OH)— or —CH(SH)—.

(3) The transition metal complex according to (1) or (2), wherein the compound represented by the formula [3] is an optically active compound, and the transition metal complex is an asymmetric transition metal complex.
(4) The transition metal complex according to any one of (1) to (3), wherein the transition metal of the complex is selected from the Groups VIII to X of the periodic table of the element.
(5) The transition metal complex according to any one of (1) to (4), wherein the transition metal of the complex is ruthenium or rhodium.
(6) The transition metal complex according to (5), which is an optically active ruthenium phosphine diamine complex represented by the following formula [1-1a]:

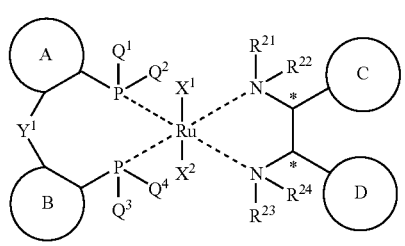

[1-1a]

wherein ring A and ring B each independently represent an aromatic ring which may have a substituent, $Q^1$, $Q^2$, $Q^3$, and $Q^4$ each independently represent an aryl group which may have a substituent or an alicyclic group which may have a substituent, $Y^1$ represents a spacer selected from a carbonyl group, a sulfonyl group, a thiocarbonyl group, —CH(OH)— or —CH(SH)—, $X^1$ and $X^2$ each independently represent a halogen atom, ring C and ring D each independently represent a phenyl group which may have a substituent or an alicyclic group which may have a substituent, $R^{21}$, $R^{22}$, $R^{23}$, and $R^{24}$ each independently represent a hydrogen atom or an alkyl group, and * represents asymmetric carbon atom.
(7) The transition metal complex according to (5), which is a rhodium phosphine complex represented by the following formula [1-2a]:

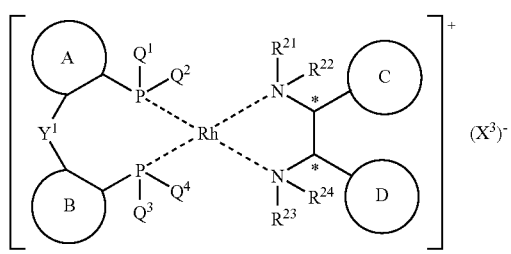

[1-2a]

wherein ring A and ring B each independently represent an aromatic ring which may have a substituent, $Q^1$, $Q^2$, $Q^3$, and $Q^4$ each independently represent an aryl group which may have a substituent or an alicyclic group which may have a substituent, $Y^1$ represents a spacer selected from a carbonyl group, a sulfonyl group, a thiocarbonyl group, —CH(OH)— or —CH(SH)—, ring C and ring D each independently represent a phenyl group which may have a substituent or an alicyclic group which may have a substituent, $R^{21}$, $R^{22}$, $R^{23}$, and $R^{24}$ each independently represent a hydrogen atom or an alkyl group, $(X^3)^-$ represents an anion, and * represents asymmetric carbon atom.
(8) The transition metal complex according to any one of (3) to (7), which is obtained in situ in a system for reaction of the formula [4]:

$$[LMX_qZ^2_m]_r \quad [4]$$

wherein L represents a compound represented by the following formula [2]:

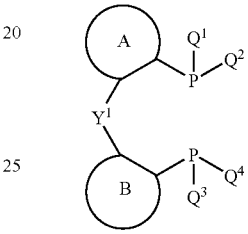

[2]

wherein ring A and ring B each independently represent an aromatic ring which may have a substituent, $Q^1$, $Q^2$, $Q^3$, and $Q^4$ each independently represent an aryl group which may have a substituent or an alicyclic group which may have a substituent, and $Y^1$ represents a spacer; M represents a transition metal; X represents a halogen atom or an anion; $Z^2$ represents a neutral ligand; q represents 1 or 2; r represents 1 or 2; and m is 0 or a natural number; with the compound represented by the formula [3] which is an optically active compound represented by the following formula [3a]:

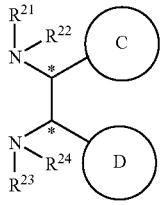

[3a]

wherein ring C and ring D each independently represent a phenyl group which may have a substituent or an alicyclic group which may have a substituent, and $R^{21}$, $R^{22}$, $R^{23}$, and $R^{24}$ each independently represent a hydrogen atom or an alkyl group.
(9) An asymmetric catalyst, comprising at least one transition metal complex according to any one of (3) to (8).
(10) An asymmetric catalyst or an asymmetric catalyst composition comprising a transition metal compound represented by the following formula [4]:

$$[LMX_qZ^2_m]_r \quad [4]$$

wherein L represents a compound represented by the following formula [2]:

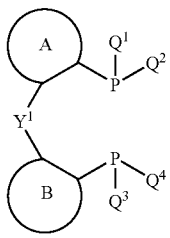

[2]

wherein ring A and ring B each independently represent an aromatic ring which may have a substituent, $Q^1$, $Q^2$, $Q^3$, and $Q^4$ each independently represent an aryl group which may have a substituent or an alicyclic group which may have a substituent, and $Y^1$ represents a spacer; M represents a transition metal; X represents a halogen atom or an anion; $Z^2$ represents a neutral ligand; q represents 1 or 2; r represents 1 or 2; and m is 0 or a natural number;

and an optically active compound represented by the following formula [3a]:

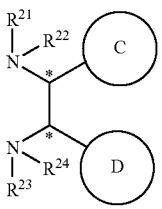

[3a]

wherein ring C and ring D each independently represent a phenyl group which may have a substituent or an alicyclic group which may have a substituent, $R^{21}$, $R^{22}$ $R^{23}$, and $R^{24}$ each independently represent a hydrogen atom or an alkyl group, and * represents asymmetric carbon atom.

(11) The asymmetric catalyst according to (9) or (10), which is an asymmetric hydrogenation catalyst.

(12) A compound represented by the following formula [2']:

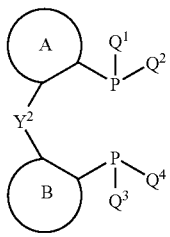

[2']

wherein ring A and ring B each independently represent an aromatic ring which may have a substituent, $Q^1$, $Q^2$, $Q^3$, and $Q^4$ each independently represent an aryl group which may have a substituent or an alicyclic group which may have a substituent, and $Y^2$ represents a carbonyl group (C=O), a sulfonyl group ($SO_2$), a thiocarbonyl group (C=S), —CH(OH)— or —CH(SH)—.

(13) A process for producing an optically active alcohol represented by the following formula [12]:

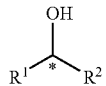

[12]

wherein $R^1$ and $R^2$ each independently represent a hydrocarbon group which may have a substituent, an aliphatic heterocyclic group which may have a substituent, or an aromatic heterocyclic group which may have a substituent (provided that a case where $R^1$ and $R^2$ are equal to each other is excluded), and $R^1$ and $R^2$ may be bonded to each other so as to form a ring together with the adjacent carbon atom, thereby forming a ring which may have a substituent; * represents asymmetric carbon atom, which comprises reacting with a ketone compound represented by the following formula [11]:

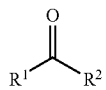

[11]

wherein $R^1$ and $R^2$ have the same meanings as described above, in the presence of the asymmetric catalyst according to any one of (9) to (11) by asymmetric hydrogenation.

The transition metal complex of the present invention is described.

Firstly, the ligand represented by L in the transition metal complex of the invention represented by the above-mentioned formula [1] is described. The ligand L is made of a diphosphine compound represented by the formula [2], and is made of an achiral compound. The aromatic ring of the aromatic ring which may have a substituent and is represented by the ring A or ring B in the formula [2] may be monocyclic, polycyclic or condensed cyclic if the aromatic ring is an aromatic ring which can form a system of π electrons the number of which is 4n+2 (wherein n is an integer). The aromatic ring, which is not particularly limited, may be a monocyclic, polycyclic or condensed cyclic aromatic ring which preferably has 6 to 20 carbon atoms and more preferably has 6 to 14 carbon atoms. Examples of such an aromatic ring include benzene, naphthalene, anthracene, and tetrahydronaphthalene.

In these aromatic rings, at least one of their hydrogen atoms may be substituted with a substituent. Examples of such a substituent include a hydrocarbon group, an alkoxy group, an aryloxy group, an aralkyloxy group, a halogen atom, an alkylenedioxy group, an amino group, a substituted amino group, a nitro group, a hydroxy group, a carboxyl group, a sulfo group and a halogenated alkyl group.

Examples of the hydrocarbon group include alkyl, alkenyl, alkynyl, aryl and aralkyl.

The alkyl group may be linear, branched or cyclic and may be a lower alkyl group or a cycloalkyl group, and examples thereof include, for example, an alkyl group having 1 to 10 carbon atoms, preferably 1 to 6 carbon atoms, or a cycloalkyl group having 3 to 10 carbon atoms, preferably 3 to 6 carbon atoms. Specific examples thereof include methyl, ethyl, n-propyl, isopropyl, n-butyl, isobutyl, tert-butyl, n-pentyl, 1-methylbutyl, 2-methylbutyl, 3-methylbutyl, 2,2-dimethylpropyl, n-hexyl, 1-methylpentyl, 2-methylpentyl, 3-methylpentyl, 4-methylpentyl, 2,2-dimethylbutyl, cyclopropyl, cyclobutyl, cyclopentyl, and cyclohexyl.

The alkenyl group is, for example, a group wherein the above-mentioned alkyl group having 2 or more carbon atoms has one or more double bonds. Specific examples thereof include ethenyl, 1-propenyl, 2-propenyl, isopropenyl, 1-butenyl, 2-butenyl, 1,3-butadienyl, 2-pentenyl, and 2-hexenyl.

The alkynyl group is, for example, a group wherein the above-mentioned alkyl group having 2 or more carbon atoms has one or more triple bonds. Specific examples thereof include ethynyl, 1-propynyl, and 2-propynyl.

The aryl group is a group made of the above-mentioned aromatic ring. Examples thereof include 5- to 7-membered monocyclic, polycyclic, or condensed cyclic aryl groups having 6 to 20 carbon atoms, preferably 6 to 14 carbon atoms. Specific examples thereof include phenyl, naphthyl, anthryl, and biphenyl.

The aralkyl group may be a group wherein at least one hydrogen atom of the above-mentioned alkyl group is substituted with the above-mentioned aryl group, for example, an aralkyl group having 7 to 26 carbon atoms, preferably 7 to 12 carbon atoms. Specific examples thereof include benzyl, 2-phenethyl, 1-phenylpropyl, and 3-naphthylpropyl.

The alkoxy group may be a group wherein an oxygen atom is bonded to the above-mentioned hydrocarbon group, for example, a lower alkoxy group or cycloalkyl group which may be linear, branched or cyclic wherein an oxygen atom is bonded to the above-mentioned alkyl group. Examples thereof include alkoxy groups having 1 to 6 carbon atoms, and cycloalkoxy groups having 3 to 6 carbon atoms. Specific examples thereof include methoxy, ethoxy, n-propoxy, 2-propoxy, n-butoxy, isobutoxy, tert-butoxy,. n-pentyloxy, 2-methylbutoxy, 3-methylbutoxy, 2,2-dimethylpropyloxy, n-hexyloxy, 2-methylpentyloxy, 3-methylpentyloxy, 4-methylpentyloxy, 5-methylpentyloxy, and cyclohexyloxy.

The aryloxy group may be a group wherein an oxygen atom is bonded to the above-mentioned aryl group, for example, an aryloxy group having 6 to 14 carbon atoms. Specific examples thereof include phenoxy, naphthyloxy, and anthryloxy.

The aralkyloxy group may be a group wherein an oxygen atom is bonded to the above-mentioned aralkyl group, for example, an aralkyloxy group having 7 to 12 carbon atoms. Specific examples thereof include benzyloxy, 2-phenethyloxy, 1-phenylpropoxy, 2-phenylpropoxy, 3-phenylpropoxy, 1-phenylbutoxy, 2-phenylbutoxy, 3-phenylbutoxy, 4-phenylbutoxy, 1-phenylpentyloxy, 2-phenylpentyloxy, 3-phenylpentyloxy, 4-phenylpentyloxy, 5-phenylpentyloxy, 1-phenylhexyloxy, 2-phenylhexyloxy, 3-phenylhexyloxy, 4-phenylhexyloxy, 5-phenylhexyloxy, and 6-phenylhexyloxy.

Examples of the halogen atoms include fluorine, chlorine, bromine, and iodine.

The substituted amino group may be an amino group wherein one or two hydrogen atoms of an amino group are substituted with the above-mentioned hydrocarbon group(s), aryl group(s) or aralkyl group(s). Examples of the hydrocarbon group(s) include alkyl, aryl and aralkyl groups. Definitions of the alkyl, aryl and aralkyl groups, and specific examples thereof are the same as described above. Specific examples of the amino group substituted with the alkyl group(s), that is, the alkyl-substituted amino group include mono- or di-alkylamino groups such as N-methylamino, N,N-dimethylamino, N,N-diethylamino, N,N-diisopropylamino, and N-cyclohexylamino. Specific examples of the amino group substituted with the aryl group(s), that is, the aryl-substituted amino group include mono- or di-arylamino groups such as N-phenylamino, N,N-diphenylamino, N-naphthylamino, N-naphthyl-N-phenylamino. Specific examples of the amino group substituted with the aralkyl group(s), that is, the aralkyl-substituted amino group include mono- or di-aralkylamino groups such as N-benzylamino, and N,N-dibenzylamino.

When the substituent is an alkylenedioxy group, two adjacent hydrogen atoms of the above-mentioned aromatic ring may be substituted with the alkylenedioxy group. The alkylenedioxy group is, for example, an alkylenedioxy group having 1 to 3 carbon atoms. Specific examples thereof include methylenedioxy, ethylenedioxy, trimethylenedioxy, and propylenedioxy.

The halogenated alkyl group may be a halogenated alkyl group having 1 to 10 carbon atoms, preferably 1 to 6 carbon atoms, wherein at least one hydrogen atom, preferably 1 to 3 hydrogen atoms of the above-mentioned alkyl group is halogenated (for example, fluorinated, chlorinated, brominated or iodinated) with one or more halogen atoms. Specific examples thereof include chloromethyl, bromomethyl, trifluoromethyl, 2-chloroethyl, 3-bromopropyl, and 3,3,3-trifluoropropyl.

In the formula [2], the aryl group which may have a substituent represented by $Q^1$ to $Q^4$ may be an aryl or substituted aryl group comprising the above-mentioned aromatic ring.

The alicyclic group which may have a substituent may be an alicyclic group or a substituted alicyclic group.

The aryl group may be the same as the above-mentioned aryl group.

The alicyclic group may be monocyclic, polycyclic or crosslinked, and is, for example, a saturated or unsaturated cyclic aliphatic hydrocarbon group having 5 to 12 carbon atoms. Specific examples thereof include cyclopentyl, cyclohexyl, decahydronaphthyl, and norbornyl.

The substituted aryl group may be an aryl group wherein at least one hydrogen atom of the above-mentioned aryl group is substituted with a substituent.

The substituted alicyclic group may be an alicyclic group wherein at least one hydrogen atom of the above-mentioned alicyclic group is substituted with a substituent.

Examples of the substituent in the substituted aryl group and the substituted alicyclic group include a hydrocarbon group, an alkoxy group, an aryloxy group, an aralkyloxy group, a halogen atom, an alkylenedioxy group, an amino group, a substituted amino group, a nitro group, a hydroxyl group, a carboxyl group, a sulfo group and a halogenated alkyl group.

Examples of the hydrocarbon, alkoxy, aryloxy, aralkyloxy, halogen, alkylenedioxy, substituted amino and halogenated alkylare the same groups as described above.

Specific examples of the substituted aryl group include tolyl, xylyl, and mesityl.

Specific examples of the substituted alicyclic group include a methylcyclohexyl.

The spacer represented by $Y^1$ in the formula [2] may be a group which is capable of linking the ring A and ring B with each other and has 1 to 5 atoms, preferably 1 to 3 atoms. The group may have various substituents. Examples of such a spacer include a carbonyl group (C=O); a sulfur atom; a sulfonyl group ($SO_2$); an oxygen atom; alkylene groups which may have a substituent, such as methylene and ethylene which may have a substituent; a thiocarbonyl group (C=S); —CH(OH)—; —CH(SH)—; an imino group (—NH—); and substituted imino groups (—NR— wherein R represents an alkyl group).

The alkylene group may be an alkylene group having 1 to 3 carbon atoms. Specific examples thereof include methylene, ethylene, trimethylene, and propylene. These alkylene groups may have the above-mentioned substituent.

Preferred examples of the spacer represented by $Y^1$ include a carbonyl group (C=O), a sulfonyl group ($SO_2$), a thiocarbonyl group (C=S), —CH(OH)—, and —CH(SH)—. The carbonyl group (C=O), sulfonyl group ($SO_2$), and —CH(OH)— are more preferred.

Preferred examples of the compound represented by the above-mentioned formula [2] include compounds represented by the following formula [2-1]:

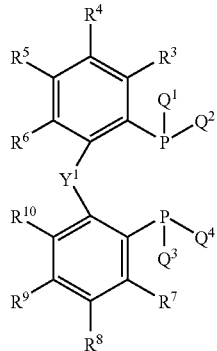

[2-1]

wherein $R^3$, $R^4$, $R^5$, $R^6$, $R^7$, $R^8$, $R^9$ and $R^{10}$ each represent the above-mentioned substituent in the ring A and ring B, and $Q^1$, $Q^2$, $Q^3$, and $Q^4$ and $Y^1$ are the same as described above.

In the formula [2], compounds wherein the spacer represented by $Y^1$ is a carbonyl group (C=O), a sulfonyl group ($SO_2$), a thiocarbonyl group (C=S), —CH(OH)— or —CH(SH)— are preferred. The compounds can be represented by the following formula [2']:

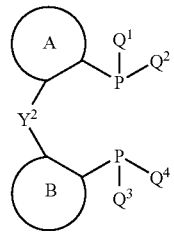

[2']

wherein ring A and ring B each independently represent an aromatic ring which may have a substituent, $Q^1$, $Q^2$, $Q^3$, and $Q^4$ each independently represent an aryl group which may have a substituent, or an alicyclic group which may have a substituent, $Y^2$ represents a carbonyl group (C=O), a sulfonyl group ($SO_2$), a thiocarbonyl group (C=S), —CH(OH)— or —CH(SH)—.

More preferred compounds among the compounds represented by the formula [2'] are compounds represented by the following formula [2'-1]:

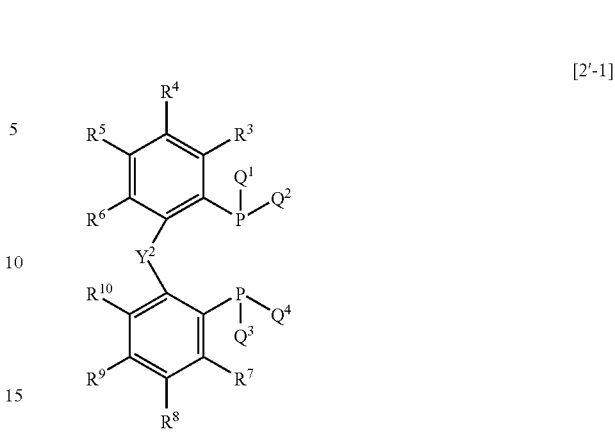

[2'-1]

wherein $R^3$, $R^4$, $R^5$, $R^6$, $R^7$, $R^8$, $R^9$, and $R^{10}$ each represent the above-mentioned substituent in the ring A and ring B, $Y^2$ represents a carbonyl group (C=O), a sulfonyl group ($SO_2$), a thiocarbonyl group (C=S), —CH(OH)— or —CH(SH)—, and $Q^1$, $Q^2$, $Q^3$, and $Q^4$ are the same as described above.

Preferred examples of the compounds represented by the formula [2] include the following compounds:

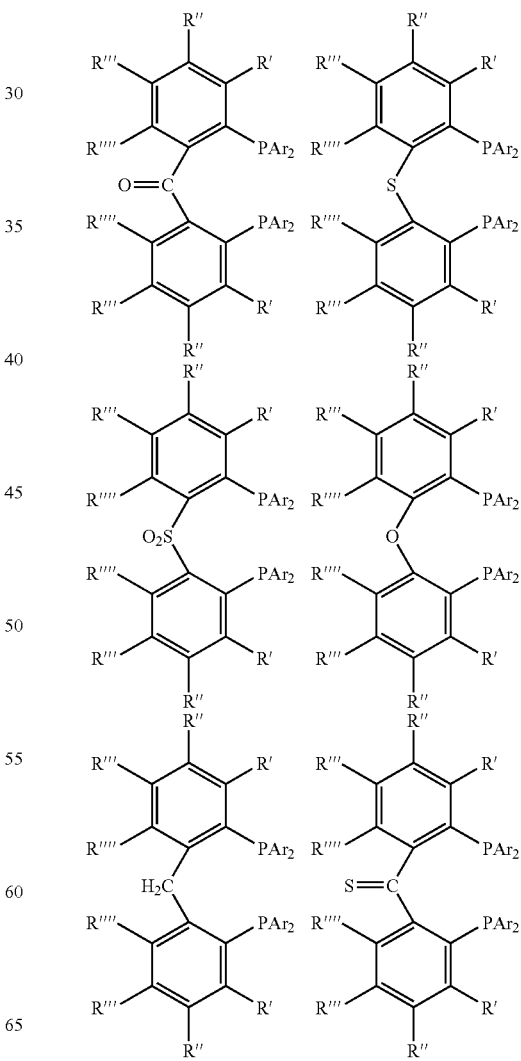

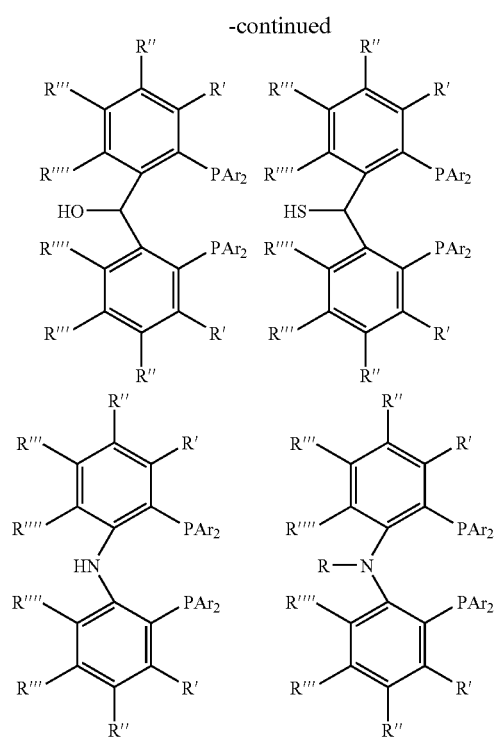
Ar: phenyl group, 4-methylphenyl,
3,5-dimethylphenyl,
4-methoxyphenyl,
1,3,5-trimethylphenyl,
1,3,5-trimethoxyphenyl etc.
R: $CH_3$, $C_2H_5$, $C_3H_7$, $CH(CH_3)_2$ etc.
R′, R″, R‴, R″″: H, $CH_3$, $C_2H_5$, $C_3H_7$, $OCH_3$, $OC_2H_5$, $OC_3H_7$ etc.
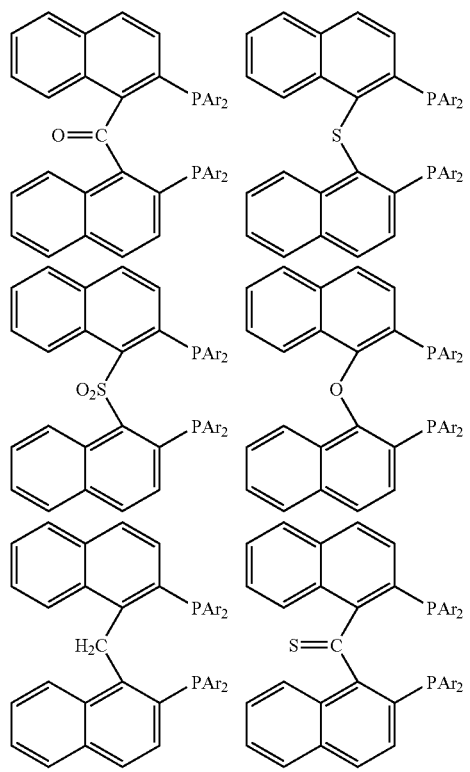
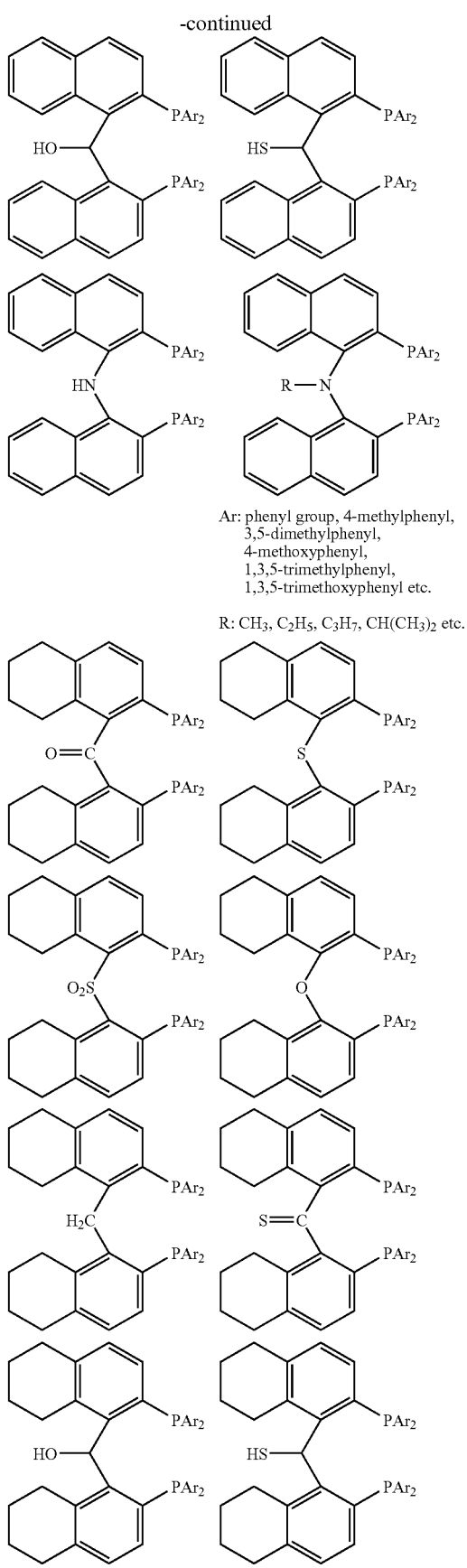
Ar: phenyl group, 4-methylphenyl,
3,5-dimethylphenyl,
4-methoxyphenyl,
1,3,5-trimethylphenyl,
1,3,5-trimethoxyphenyl etc.
R: $CH_3$, $C_2H_5$, $C_3H_7$, $CH(CH_3)_2$ etc.

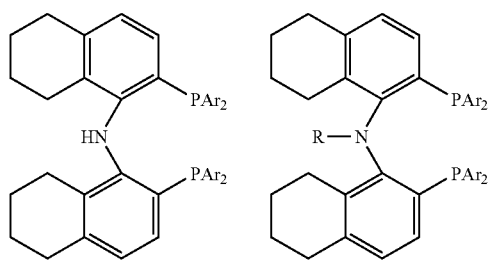

Ar: phenyl group, 4-methylphenyl,
3,5-dimethylphenyl,
4-methoxyphenyl,
1,3,5-trimethylphenyl,
1,3,5-trimethoxyphenyl etc.

R: $CH_3$, $C_2H_5$, $C_3H_7$, $CH(CH_3)_2$ etc.

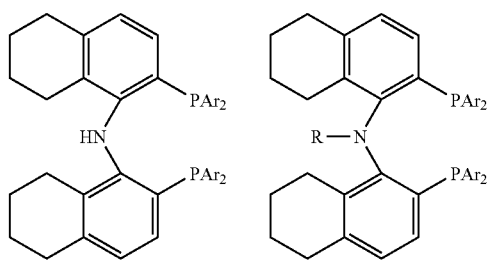

Ar: phenyl group, 4-methylphenyl,
3,5-dimethylphenyl,
4-methoxyphenyl,
1,3,5-trimethylphenyl,
1,3,5-trimethoxyphenyl etc.

R: $CH_3$, $C_2H_5$, $C_3H_7$, $CH(CH_3)_2$ etc.

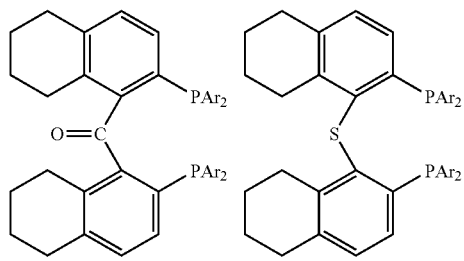

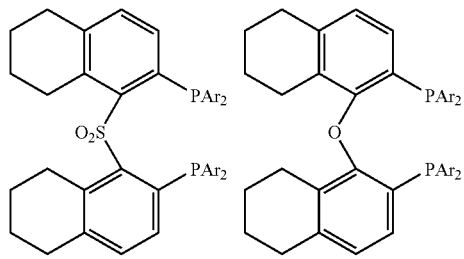

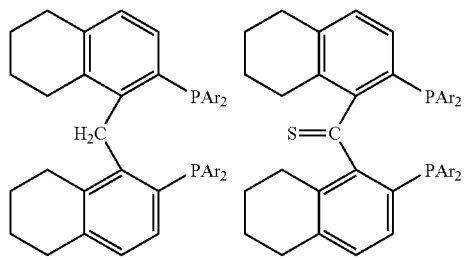

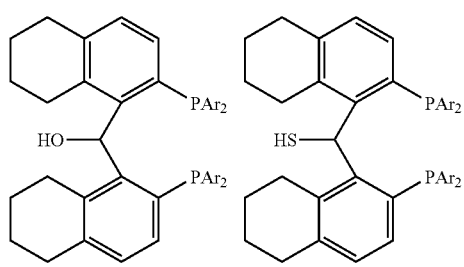

Also, more preferred examples of the compounds represented by the above-mentioned formula [2'] include the following compounds:

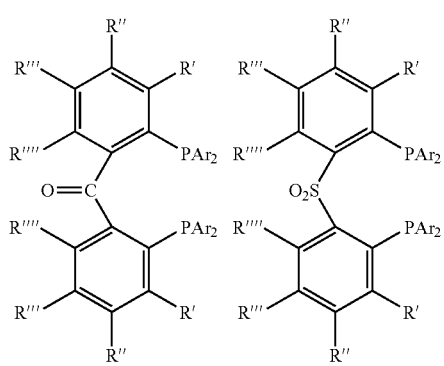

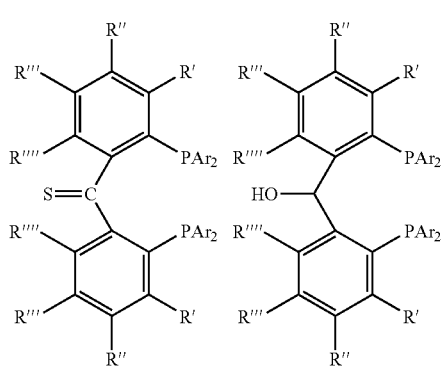

-continued

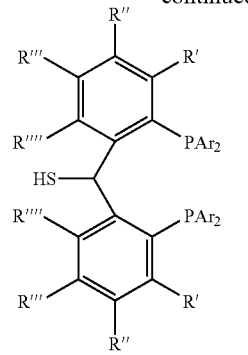

Ar: phenyl group, 4-methylphenyl,
3,5-dimethylphenyl,
4-methoxyphenyl,
1,3,5-trimethylphenyl,
1,3,5-trimethoxyphenyl etc.

R', R'', R''', R'''', R''''': H, $CH_3$, $C_2H_5$, $C_3H_7$,
$OCH_3$, $OC_2H_5$, $OC_3H_7$
etc.

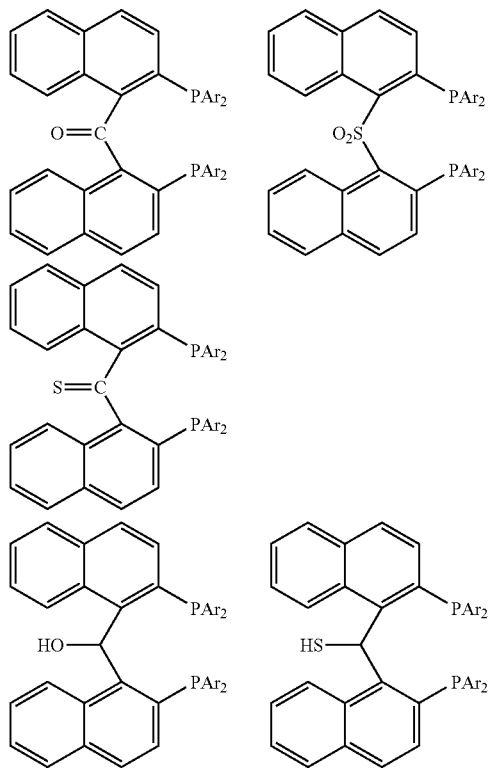

Ar: phenyl group, 4-methylphenyl,
3,5-dimethylphenyl,
4-methoxyphenyl,
1,3,5-trimethylphenyl,
1,3,5-trimethoxyphenyl etc.

R: $CH_3$, $C_2H_5$, $C_3H_7$, $CH(CH_3)_2$ etc.

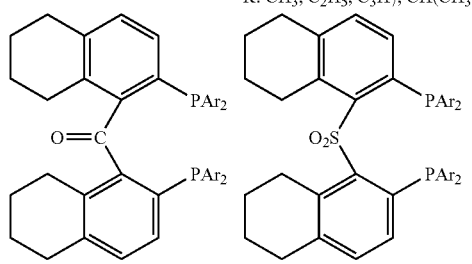

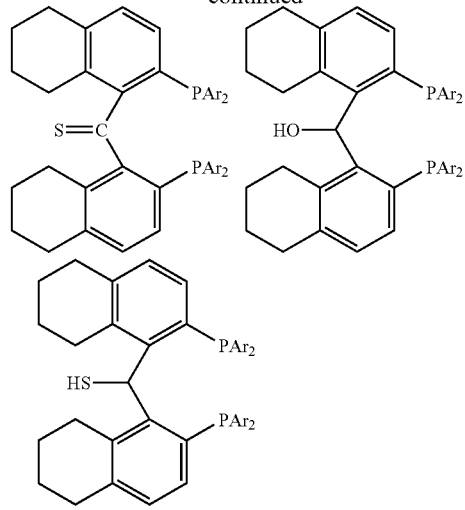

Ar: phenyl group, 4-methylphenyl,
3,5-dimethylphenyl,
4-methoxyphenyl,
1,3,5-trimethylphenyl,
1,3,5-trimethoxyphenyl etc.

R: $CH_3$, $C_2H_5$, $C_3H_7$, $CH(CH_3)_2$ etc.

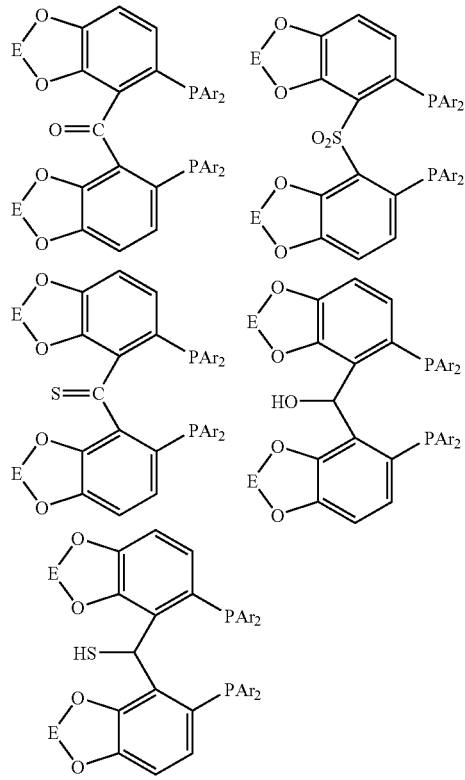

Ar: phenyl group, 4-methylphenyl,
3,5-dimethylphenyl,
4-methoxyphenyl,
1,3,5-trimethylphenyl,
1,3,5-trimethoxyphenyl etc.

E: —$CH_2$—, —$CH_2CH_2$—,
—$CH_2CH_2CH_2$—,
—$CH_2CH(CH_3)$—

R: $CH_3$, $C_2H_5$, $C_3H_7$, $CH(CH_3)_2$ etc.

In the formula [1] and the formula [4], examples of the transition metal represented by M include transition metals in the groups VIII to X in the periodic table of the element (according to classification of groups suggested by the Inorganic Chemistry Division in the American Chemical Society (in 1985); the same matter is correspondingly applied to the following), preferably transition metals in the groups VIII to IX in the periodic table of the element. Specific examples thereof preferably include ruthenium, rhodium, and iridium, and more preferably include ruthenium and rhodium.

In the formulae [1] and [4], the anion represented by X and $(X^3)^-$ may be an anion of a halogen atom such as a fluorine, chlorine, bromine, or iodine atom. The anion is preferably an anion of chlorine, bromine or iodine. Examples other than the halogen atoms include $BF_4$, $ClO_4$, OTf, $PF_6$, $SbF_6$, $BPh_4$, and $B(3,5-(CF_3)_2C_6H_3)_4$.

In the formula [4], the neutral ligand represented by $Z^2$ may be $H_2O$, the above-mentioned neutral aromatic compound, a neutral olefin compound, or some other neutral compound, and is preferably a neutral organic compound having a π electron or some other neutral ligand. Examples of the neutral aromatic compound include benzonitrile, benzene, and alkyl-substituted benzene. Examples of the alkyl-substituted benzene include p-cymene, hexamethylbenzene, and 1,3,5-trimethylbenzene (mesitylene).

Examples of the neutral olefin compound include ethylene, 1,5-cyclooctadiene, cyclopentadiene, pentamethylcyclopentadiene, and norbornadiene.

Examples of some other neutral ligand include N,N-dimethylformamide (DMF), acetonitrile, acetone, and chloroform.

Preferred specific examples of the metal compound represented by the formula [4] include compounds described below. Provided that the metal compound represented by the formula [4] is not limited to these. L in the following formulae is the same as described above.

Rhodium Complexes:

[Rh(L)Cl]$_2$, [Rh(L)Br]$_2$, [Rh(L)I]$_2$, [Rh(cod)(L)]BF$_4$, [Rh(cod)(L)]ClO$_4$, [Rh(cod)(L)]PF$_6$, [Rh(cod)(L)]BPh$_4$, [Rh(cod)(L)]OTf, [Rh(nbd)(L)]BF$_4$, [Rh(nbd)(L)]ClO$_4$, [Rh(nbd)(L)]PF$_6$, [Rh(nbd)(L)]BPh$_4$, [Rh(nbd)(L)]OTf, and [Rh(cod)(L)]SbF$_6$;

Ruthenium Complexes:

Ru(OAc)$_2$(L), Ru$_2$Cl$_4$(L)$_2$NEt$_3$, [RuCl(benzene)(L)]Cl, [RuBr(benzene)(L)]Br, [RuI(benzene)(L)]I, [RuCl(p-cymene)(L)]Cl, [RuBr(p-cymene)(L)]Br, [RuI(p-cymene)(L)]I, [Ru(L)](BF$_4$)$_2$, [Ru(L)](ClO$_4$)$_2$, [Ru(L)](PF$_6$)$_2$, [Ru(L)](BPh$_4$)$_2$, and [Ru(L)](OTf)$_2$;

Iridium Complexes:

Specific examples of the iridium complex include the following complexes:

[Ir(L)Cl]$_2$, [Ir(L)Br]$_2$, [Ir(L)I]$_2$, [Ir(cod)(L)]BF$_4$, [Ir(cod)(L)]ClO$_4$, [Ir(cod)(L)]PF$_6$, [Ir(cod)(L)]BPh$_4$, [Ir(cod)(L)]OTf, [Ir(nbd)(L)]BF$_4$, [Ir(nbd)(L)]ClO$_4$, [Ir(nbd)(L)]PF$_6$, [Ir(nbd)(L)]BPh$_4$, and [Ir(nbd)(L)]OTf.

In the formula [1], $Z^1$ represents a compound represented by the formula [3], and examples thereof include diamines such as aromatic diamines, and aliphatic diamines.

As the phenyl group represented by the ring C or ring D, the phenyl group which may have a substituent include phenyl and substituted phenyl.

The substituted phenyl group may be a phenyl group wherein at least one hydrogen atom, preferably 1 to 3 hydrogen atoms of a phenyl group is substituted with a substituent.

Examples of said substituent(s) include the above-mentioned groups such as alkyl, aryl, alkoxy and aryloxy.

The alicyclic group which may have a substituent include an alicyclic group and a substituted alicyclic group.

Examples of the alicyclic group include the above-mentioned cyclohexyl group and the like.

The substituted alicyclic group may be an alicyclic group wherein at least one hydrogen atom of the above-mentioned alicyclic group is substituted with a substituent. Examples of the substituent(s) include the above-mentioned groups such as alkyl, aryl, alkoxy, and aryloxy.

Alkyl, aryl, alkoxy, and aryloxy groups are the same groups as described above.

Specific examples of the substituted phenyl group include tolyl, xylyl, mesityl, methoxyphenyl, and dimethoxyphenyl.

Specific examples of the substituted alicyclic group include a methylcyclohexyl group and the like.

In the case that the compound represented by the formula [3] is an optically active compound, the compound include, for example, an optically active compound represented by the formula [3a]. A preferred example of the compound [3a] include an optically active compound represented by the following formula [3-1a]:

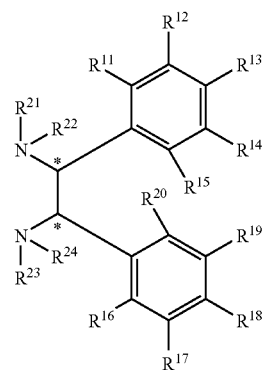

[3-1a]

wherein $R^{11}$, $R^{12}$, $R^{13}$, $R^{14}$, $R^{15}$, $R^{16}$, $R^{17}$, $R^{18}$, $R^{19}$, and $R^{20}$, and $R^{21}$, $R^{22}$, $R^{23}$, and $R^{24}$ each represent the above-mentioned substituent of the ring C and ring D, and * is the same as described above.

In the compound represented by the formula [3], examples of the aromatic diamine include diphenylethylenediamine, and 1,2-bis(4-methoxyphenyl)ethylenediamine. When an optically active aromatic diamine is used as the aromatic diamine, the resultant transition metal complex, for example, ruthenium phosphine diamine complex becomes an optically active transition metal complex, for example, an optically active ruthenium phosphine diamine complex.

Examples of the optically active aromatic diamine include optically active substances of the above-mentioned aromatic diamines, that is, (1R,2R)-diphenylethylenediamine, (1S,2S)-diphenylethylenediamine, (1R,2R)- 1,2-bis(4-methoxyphenyl)ethylenediamine, and (1S,2S)-1,2-bis(4-methoxyphenyl)ethylenediamine.

An example of the alicyclic diamine thereof is dicyclohexylethylenediamine and the like.

Examples of the optically active aliphatic diamine thereof include (1R,2R)-dicyclohexylethylenediamine, and (1S,2S)-dicyclohexylethylenediamine.

In the compounds represented by the formula [3] and [3a], the alkyl group represented by $R^{21}$ to $R^{24}$ may be a lower alkyl group which may be linear, branched or cyclic, for example, an alkyl group having 1 to 6 carbon atoms, preferably 1 to 3 carbon atoms. Specific examples thereof include methyl, ethyl, n-propyl, and 2-propyl.

As the transition metal complex represented by the formula [1], for example, a ruthenium phosphine diamine complex, wherein the transition metal represented by M is ruthenium, is, for example, a ruthenium phosphine diamine complex represented by the following formula [1-1]:

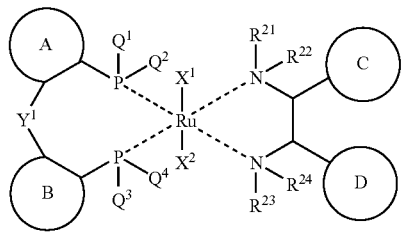

[1-1]

wherein ring A, ring B, ring C, and ring D, $Q^1$, $Q^2$, $Q^3$, and $Q^4$, $R^{21}$, $R^{22}$, $R^{23}$, and $R^{24}$, $X^1$ and $X^2$, and $Y^1$ are the same as described above.

Also, a rhodium phosphine complex wherein the transition metal represented by M is rhodium is, for example, a rhodium phosphine diamine complex represented by the following formula [1-2]:

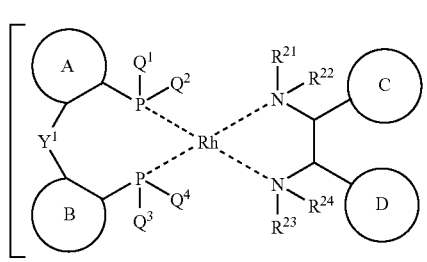

[1-2]

wherein ring A, ring B, ring C, and ring D, $Q^1$, $Q^2$, $Q^3$, and $Q^4$, $R^{21}$, $R^{22}$, $R^{23}$, $R^{24}$, and $(X^3)^-$, and $Y^1$ are the same as described above.

A preferred example of the ruthenium phosphine diamine complex represented by the formula [1-1] is a ruthenium phosphine diamine complex represented by the following formula [1-3]:

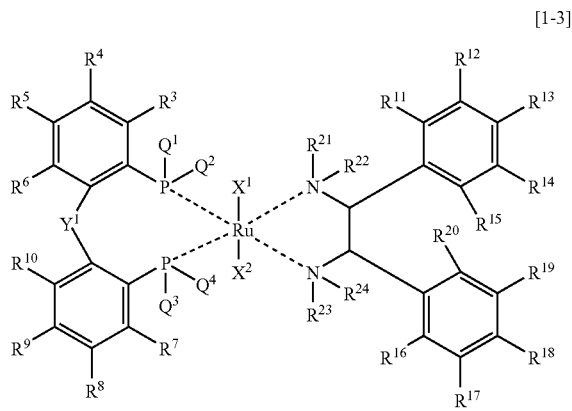

[1-3]

wherein $R^3$, $R^4$, $R^5$, $R^6$, $R^7$, $R^8$, $R^9$ and $R^{10}$ each independently represent hydrogen, hydrocarbon, alkoxy, aryloxy, aralkyloxy, halogen, alkylenedioxy, amino, substituted amino, nitro, hydroxyl, carboxyl, sulfo or halogenated alkyl, $R^{11}$, $R^{12}$, $R^{13}$, $R^{14}$, $R^{15}$, $R^{16}$, $R^{17}$, $R^{18}$, $R^{19}$, and $R^{20}$ each independently represent hydrogen, an alkyl, aryl, alkoxy or aryloxy, $R^3$ and $R^4$, $R^4$ and $R^5$, $R^5$ and $R^6$, $R^7$ and $R^8$, $R^8$ and $R^9$, or $R^9$ and $R^{10}$ may be bonded to each other and combined with a ring to which they are bonded, so as to form a condensed ring, and $Q^1$, $Q^2$, $Q^3$, and $Q^4$, $Y^1$, $X^1$, $X^2$, $R^{21}$, $R^{22}$, $R^{23}$, and $R^{24}$ are the same as described above.

Also, a preferred example of the rhodium phosphine diamine complex represented by the formula [1-2] is a rhodium phosphine diamine complex represented by the following formula [1-4]:

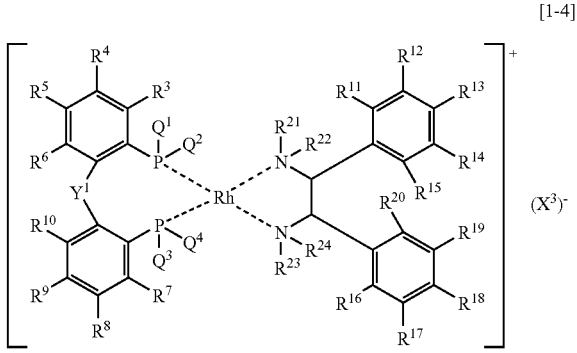

[1-4]

wherein $R^3$, $R^4$, $R^5$, $R^6$, $R^7$, $R^8$, $R^9$ and $R^{10}$, $R^{11}$, $R^{12}$, $R^{13}$, $R^{14}$, $R^{15}$, $R^{16}$, $R^{17}$, $R^{18}$, $R^{19}$ and $R^{20}$, $Q^1$, $Q^2$, $Q^3$, and $Q^4$, $Y^1$, and $R^{21}$, $R^{22}$, $R^{23}$, and $R^{24}$ are the same as described above, and $X^3$ is identical with $X^1$ or $X^2$.

In the above-mentioned formulae [1-3] and [1-4], examples of the hydrocarbon, alkoxy, aryloxy, aralkyloxy, halogen, alkylenedioxy, substituted amino and halogenated alkyl represented by $R^3$, $R^4$, $R^5$, $R^6$, $R^7$, $R^8$, $R^9$, and $R^{10}$ are the same as exemplified as the substituent in the ring A and ring B. Examples of the alkyl, aryl, alkoxy and aryloxy groups represented by $R^{10}$, $R^{11}$, $R^{12}$, $R^{13}$, $R^{14}$, $R^{15}$, $R^{16}$, $R^{17}$, $R^{18}$, $R^{19}$ and $R^{20}$ are the same as exemplified as the substituent in the ring C and ring D. In the case that $R^3$ and $R^4$, $R^4$ and $R^5$, $R^5$ and $R^6$, $R^7$ and $R^8$, $R^8$ and $R^9$, or $R^9$ and $R^{10}$ may be bonded to each other and combined with a ring to which they are bonded so as to form a condensed ring, examples of the condensed ring include the rings exemplified as the aromatic ring in the ring A and ring B, that is, naphthalene, anthracene, and tetrahydronaphthalene.

In a production process of the transition metal complex of the present invention which will be described later, when an optically active diamine is used as the diamine, an optically active transition metal complex can be obtained. For example, in the ruthenium phosphine diamine complex represented by the above-mentioned formula [1-1], an optically active ruthenium phosphine diamine complex represented by the following formula [1-1a] is obtained in the case that an optically active diamine is used as the diamine when this ruthenium phosphine diamine complex is produced:

[1-1a]

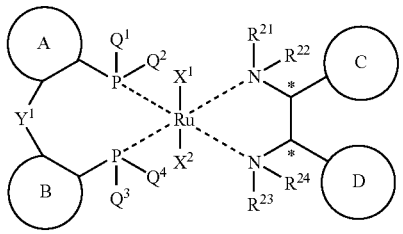

wherein * represents an asymmetric carbon atom, and ring A, ring B, ring C, and ring D, $Q^1$, $Q^2$, $Q^3$, and $Q^4$, $Y^1$, $X^1$, $X^2$, and $R^{21}$, $R^{22}$, $R^{23}$, and $R^{24}$ are the same as described above.

About the rhodium phosphine diamine complex represented by the formula [1-2], an optically active rhodium phosphine diamine complex represented by the following formula [1-2a] is obtained in the case that an optically active diamine is used as the diamine when this rhodium phosphine diamine complex is produced:

[1-2a]

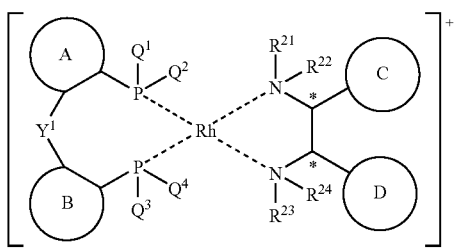

wherein ring A, ring B, ring C and ring D, $Q^1$, $Q^2$, $Q^3$, and $Q^4$, $Y^1$, $(X^3)^-$, $R^{21}$, $R^{22}$, $R^{23}$, and $R^{24}$, and * are the same as described above.

A more preferred example of the optically active ruthenium phosphine diamine complex represented by the above-mentioned formula [1-1a] is, for example, an optically active ruthenium phosphine diamine complex represented by the following formula [1-3a]:

[1-3a]

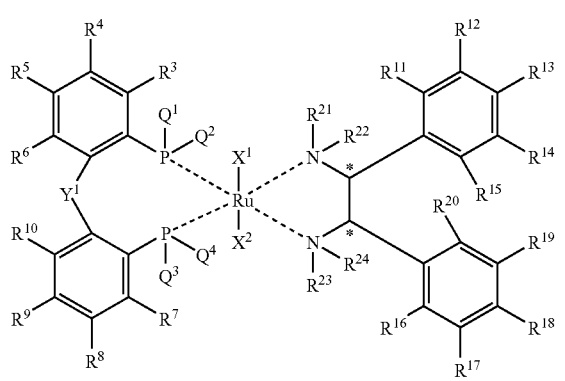

wherein $R^3$, $R^4$, $R^5$, $R^6$, $R^7$, $R^8$, $R^9$, and $R^{10}$, $R^{11}$, $R^{12}$, $R^{13}$, $R^{14}$, $R^{15}$, $R^{16}$, $R^{17}$, $R^{18}$, $R^{19}$, and $R^{20}$, $Q^1$, $Q^2$, $Q^3$, and $Q^4$, $Y^1$, $X^1$, $X^2$, $R^{21}$, $R^{22}$, $R^{23}$, and $R^{24}$, and * are the same as described above.

Also, as a more preferred example of the optically active rhodium phosphine diamine complex represented by the above-mentioned formula [1-2a], for example, an optically active rhodium phosphine diamine complex represented by the following formula [1-4a] is obtained:

[1-4a]

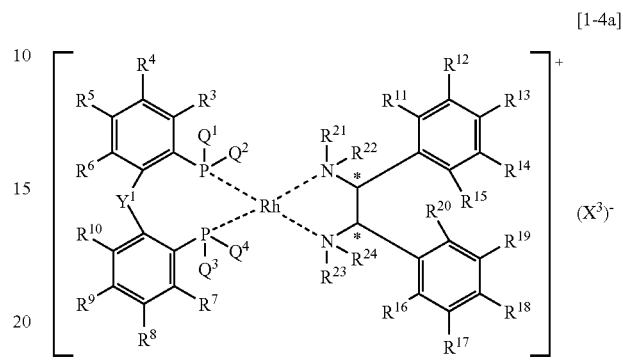

wherein $R^3$, $R^4$, $R^5$, $R^6$, $R^7$, $R^8$, $R^9$, and $R^{10}$, $R^{11}$, $R^{12}$, $R^{13}$, $R^{14}$, $R^{15}$, $R^{16}$, $R^{17}$, $R^{18}$, $R^{19}$, and $R^{20}$, $Q^1$, $Q^2$, $Q^3$, and $Q^4$, $Y^1$, $(X^3)^-$, $R^{21}$, $R^{22}$, $R^{23}$, and $R^{24}$, and * are the same as described above.

Specific examples of the above-mentioned optically active ruthenium phosphine diamine complex represented by the formula [1-3a] include the following compounds:

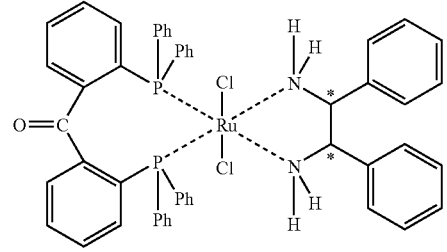

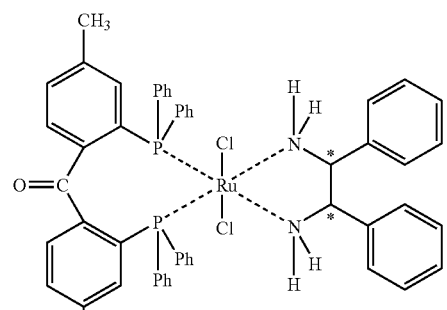

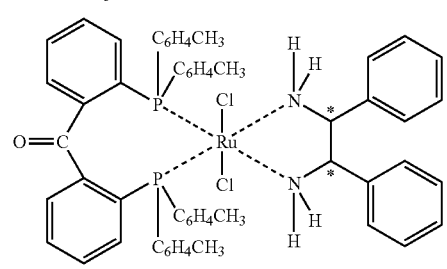

-continued
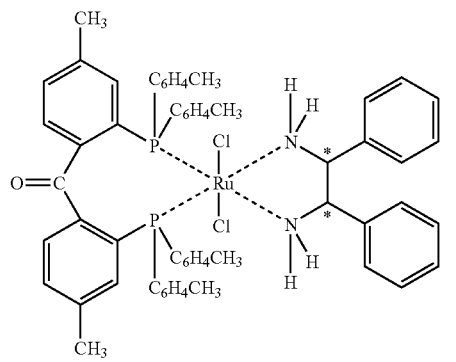
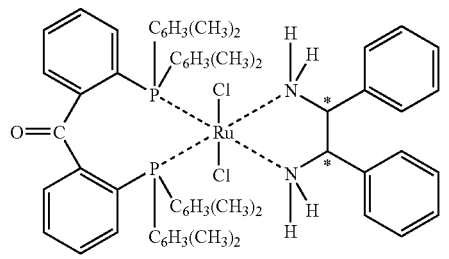
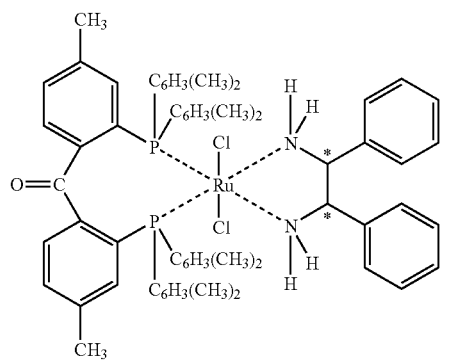
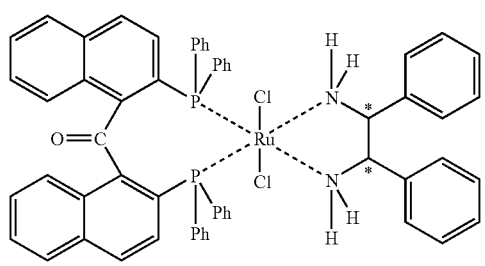
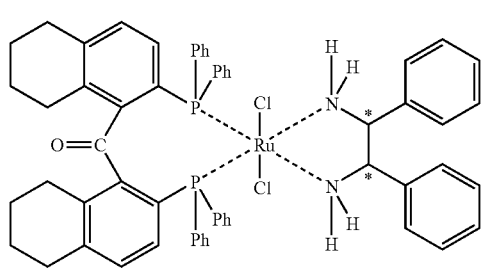
-continued
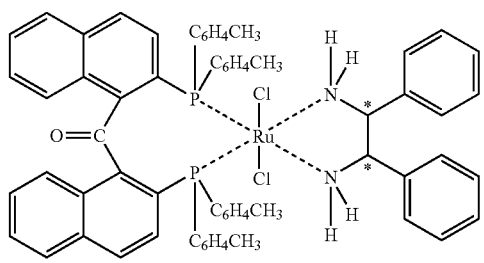
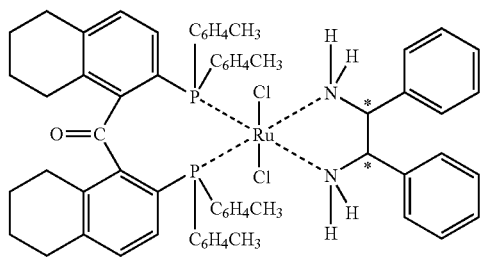
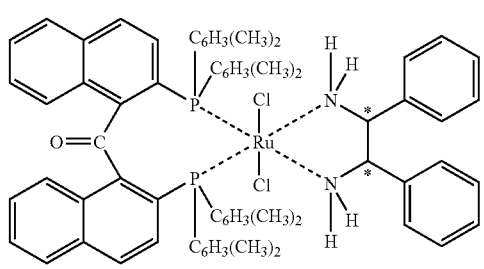
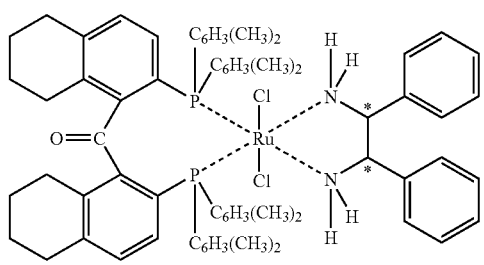
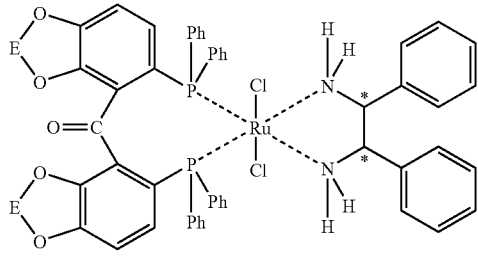
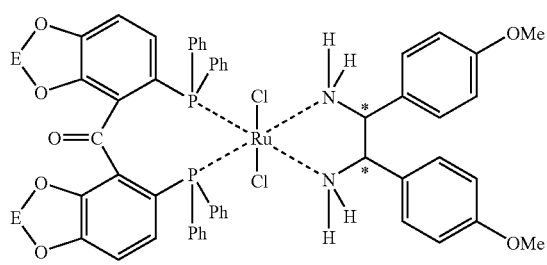

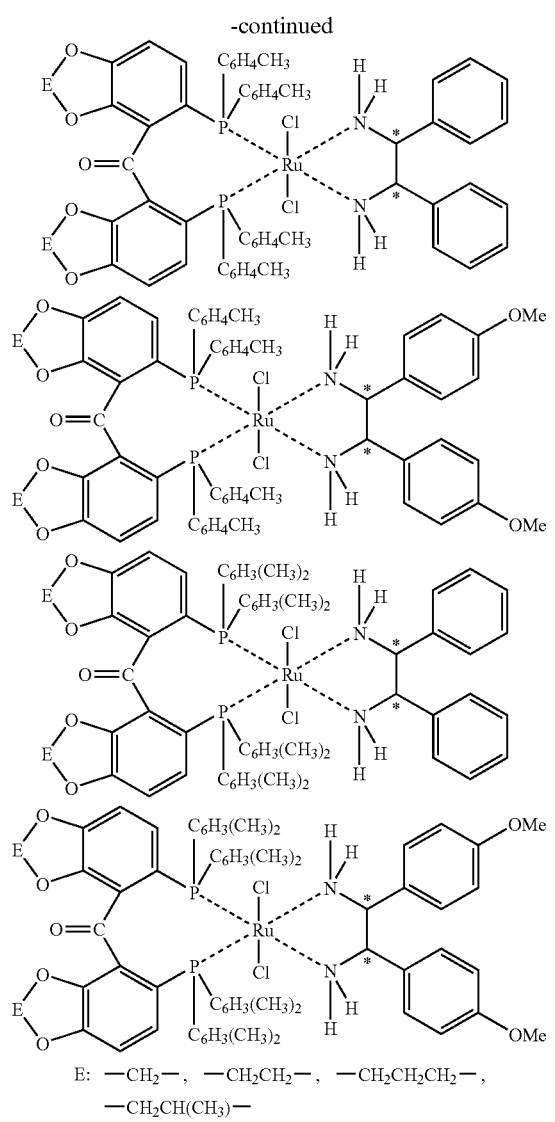
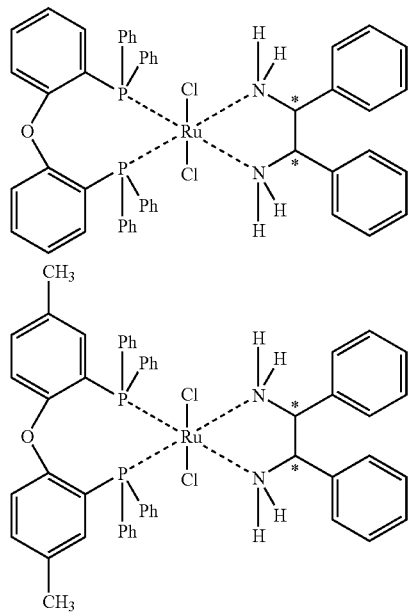
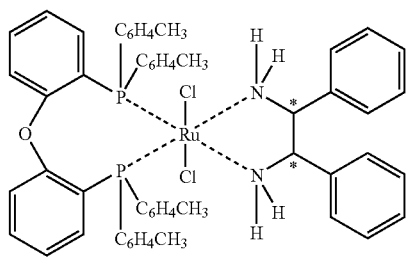
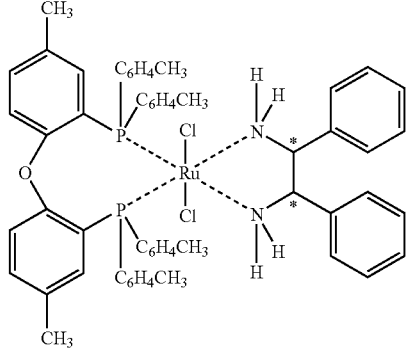
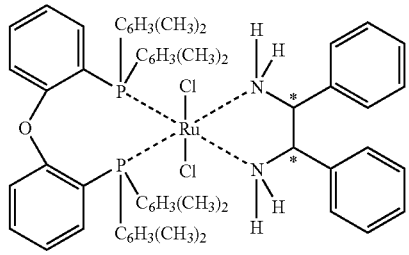
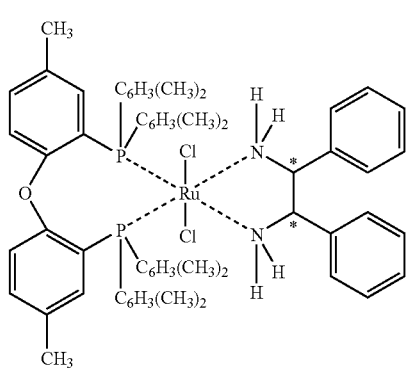
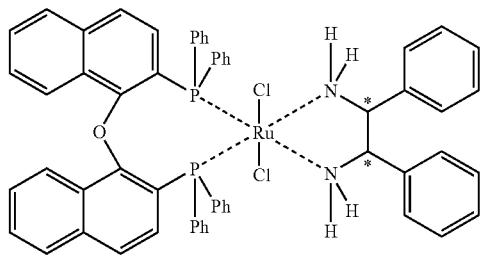
E: —CH₂—, —CH₂CH₂—, —CH₂CH₂CH₂—, —CH₂CH(CH₃)—

-continued
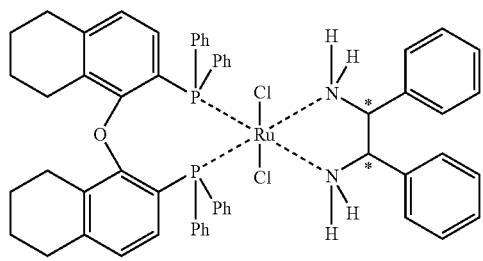
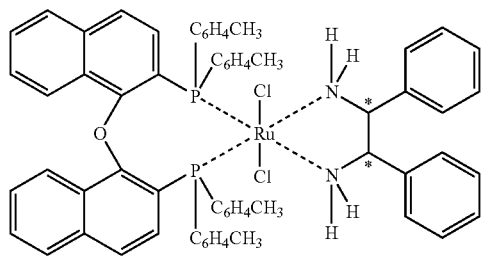
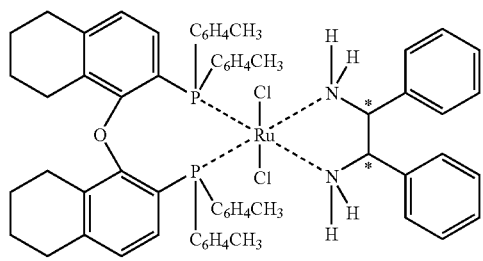
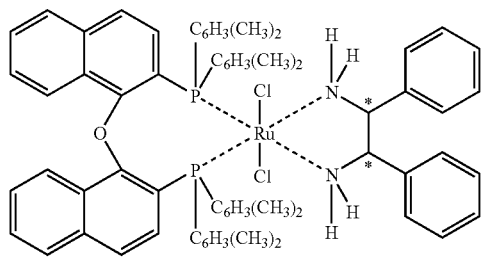
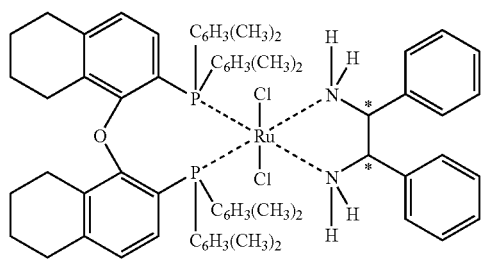
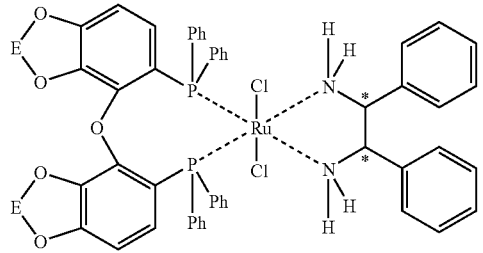
-continued
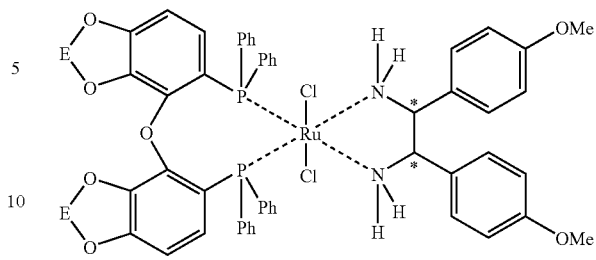
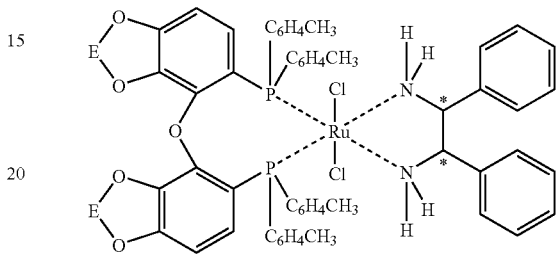
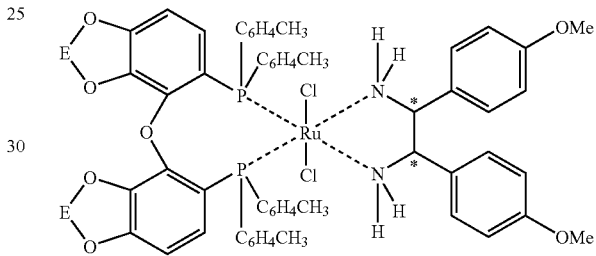
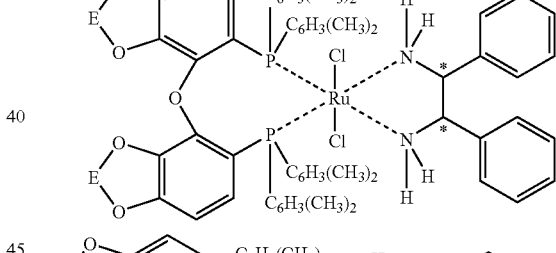
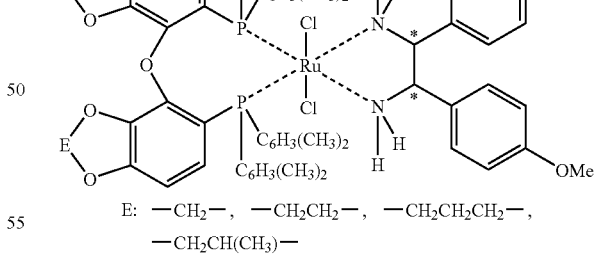
E: —CH$_2$—, —CH$_2$CH$_2$—, —CH$_2$CH$_2$CH$_2$—, —CH$_2$CH(CH$_3$)—
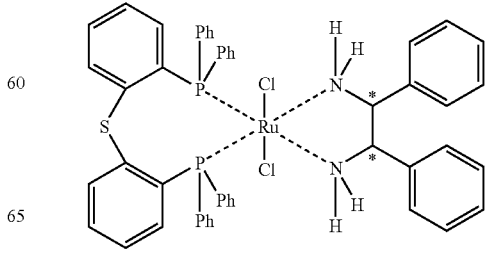

-continued
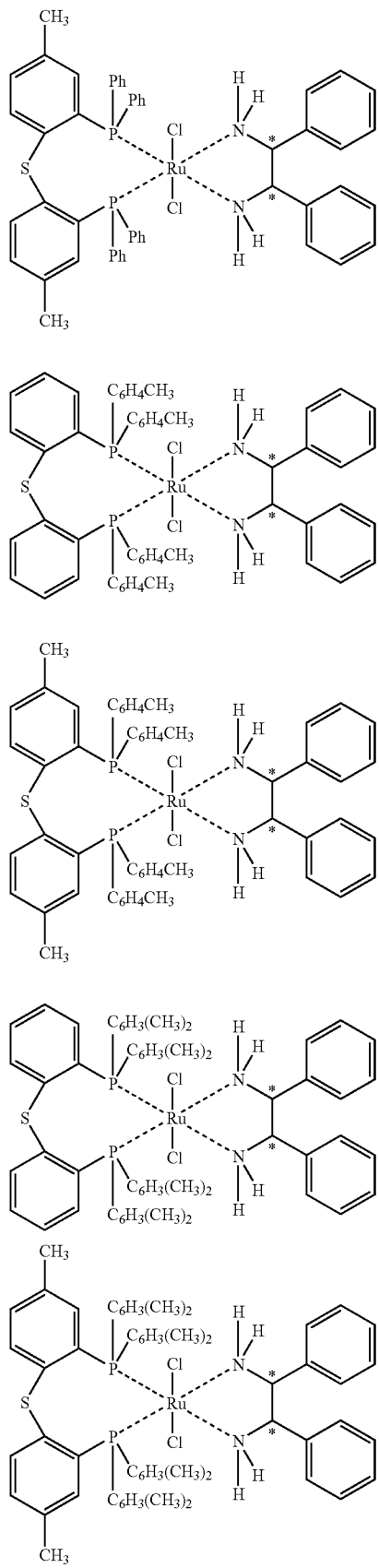
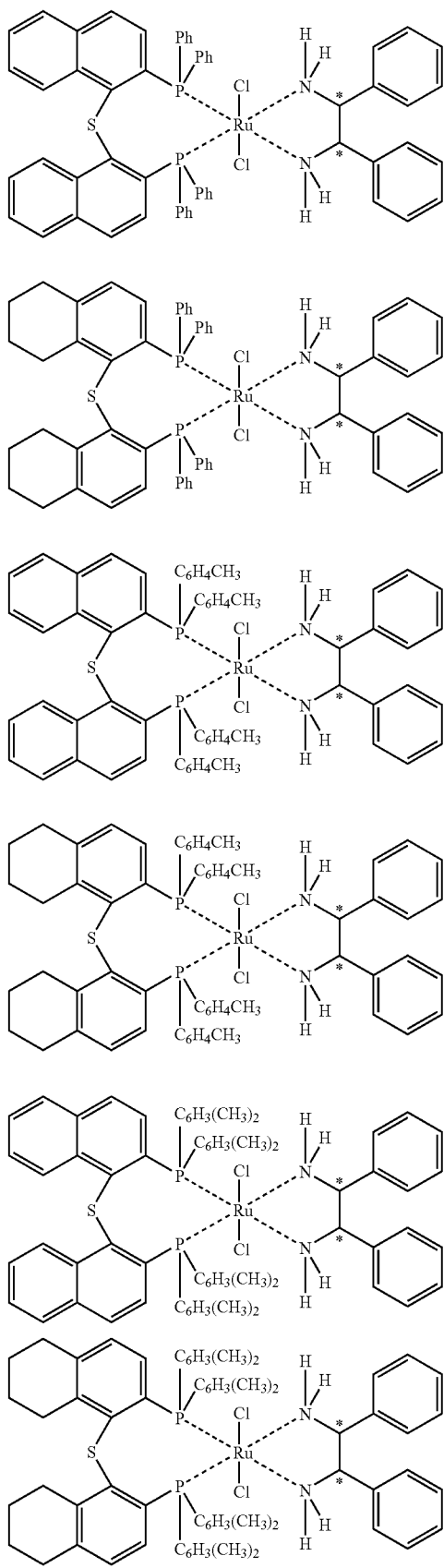

-continued
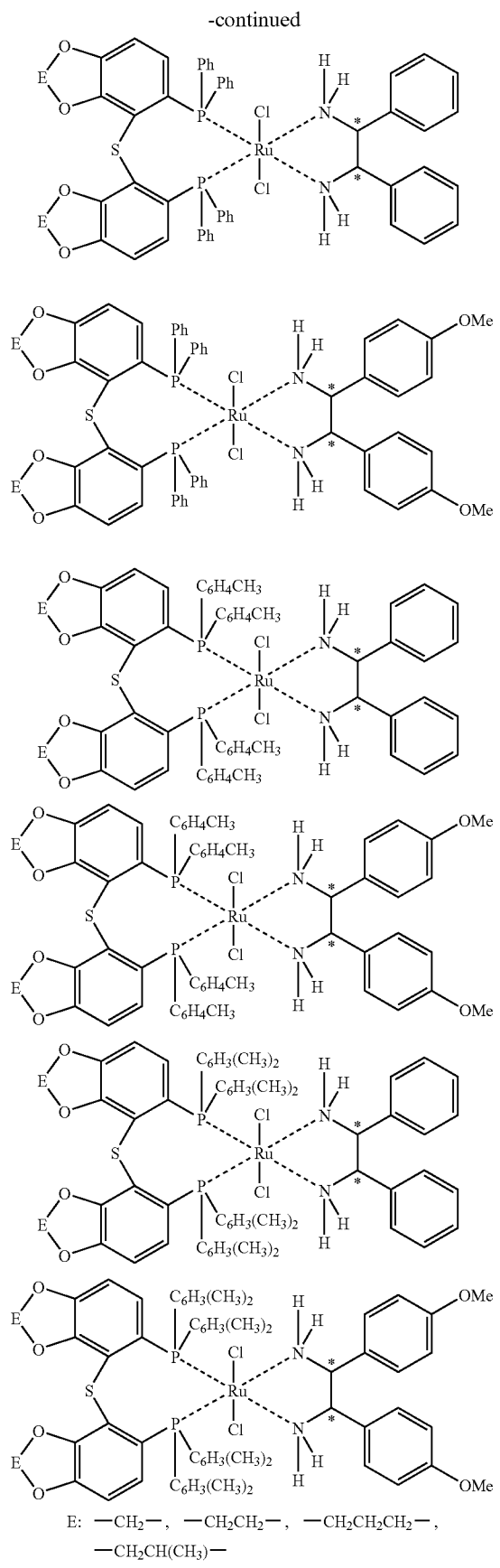
E: —CH₂—, —CH₂CH₂—, —CH₂CH₂CH₂—,
—CH₂CH(CH₃)—
-continued
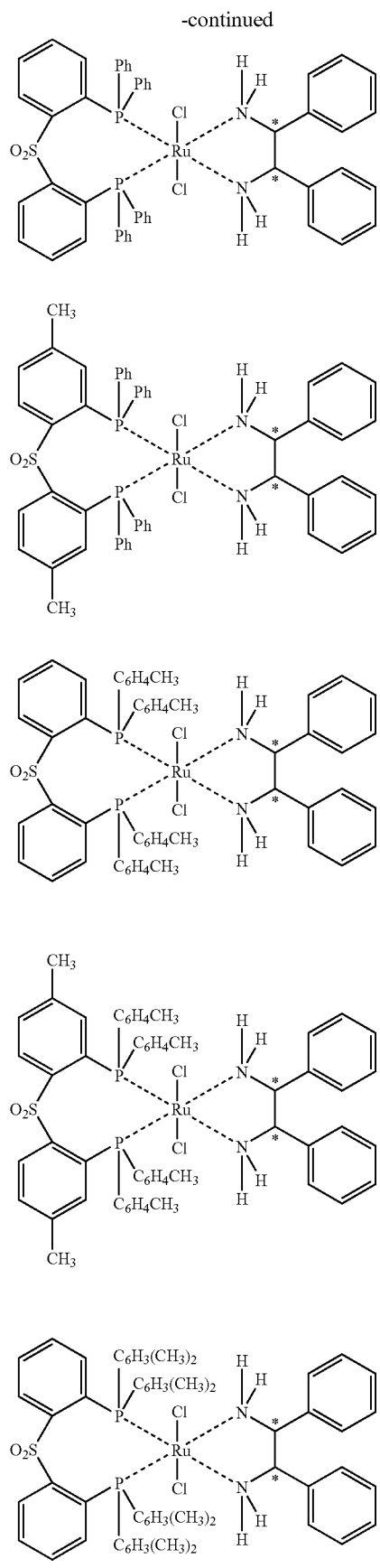

-continued
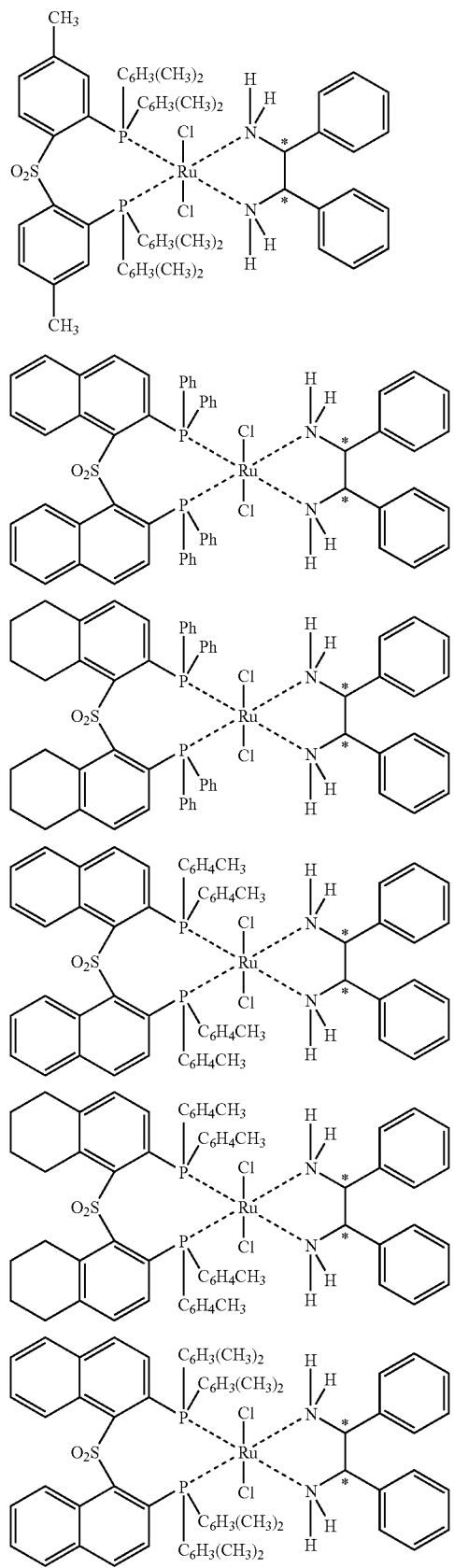
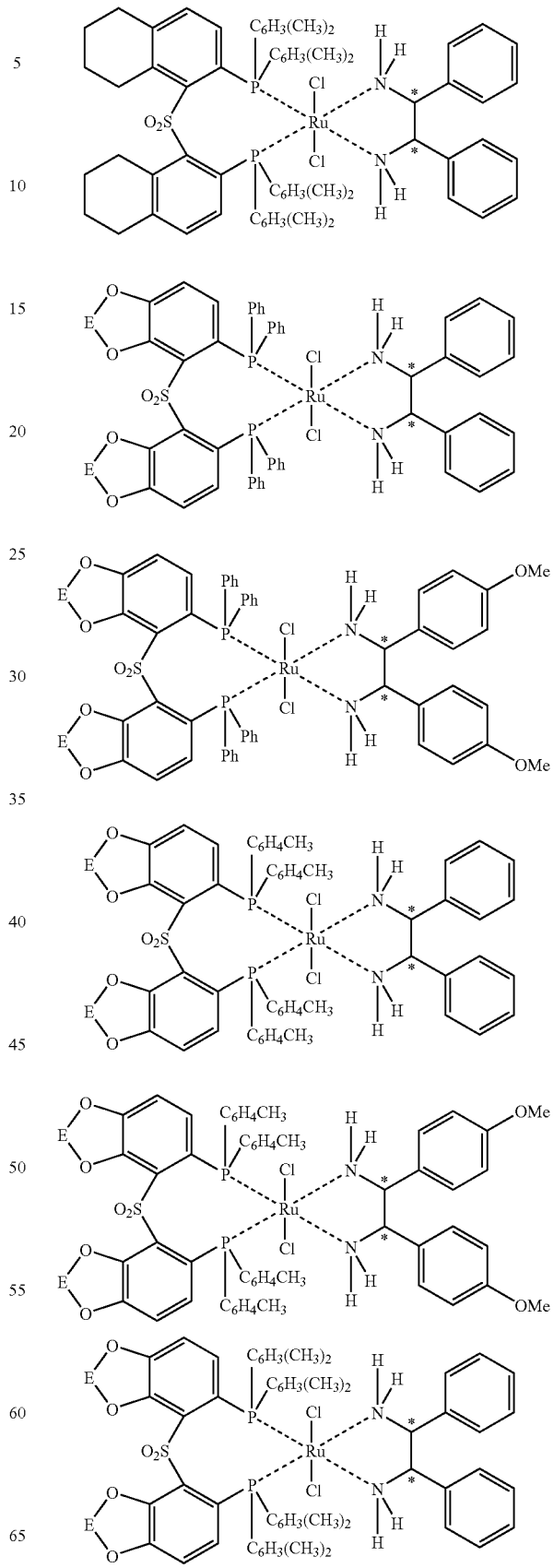

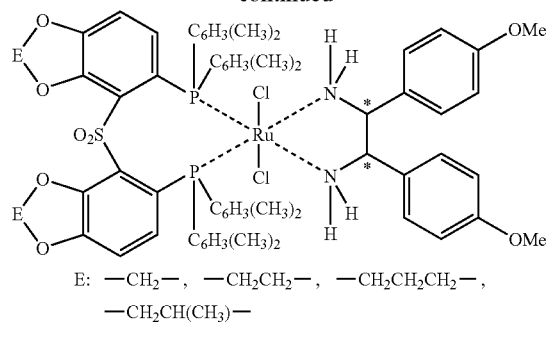
E: —CH₂—, —CH₂CH₂—, —CH₂CH₂CH₂—,
—CH₂CH(CH₃)—
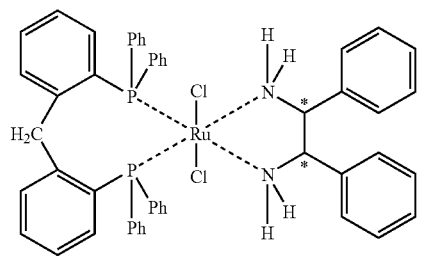
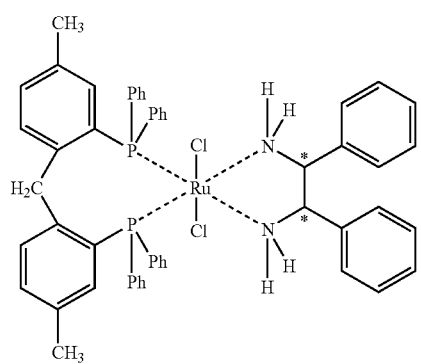
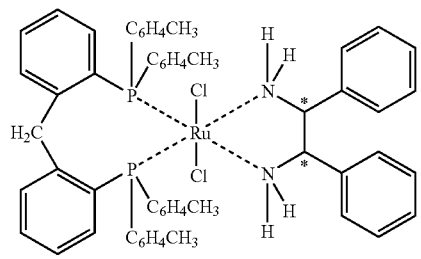
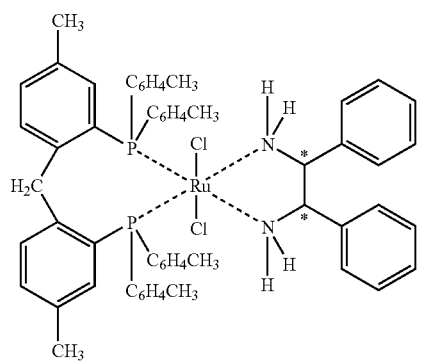
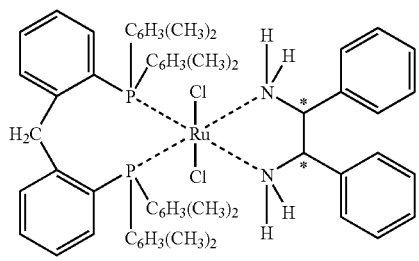
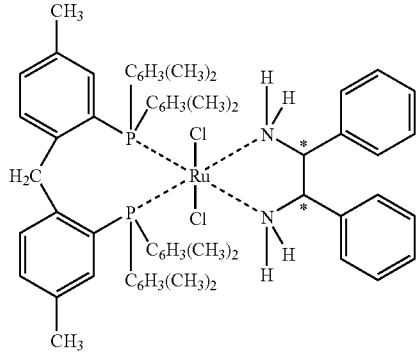
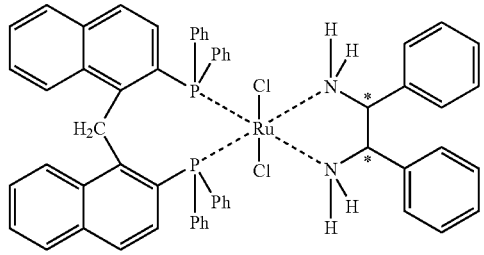
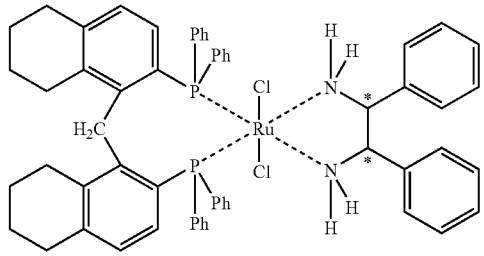
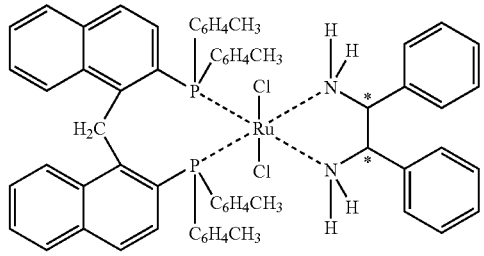
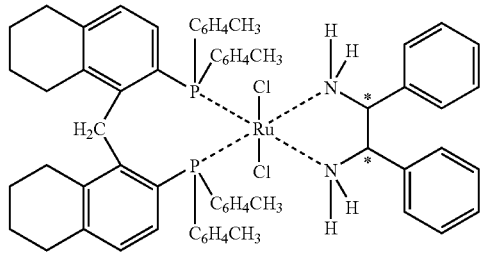

-continued
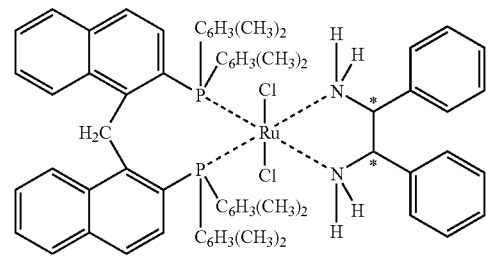
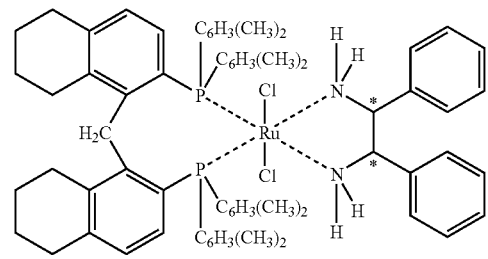
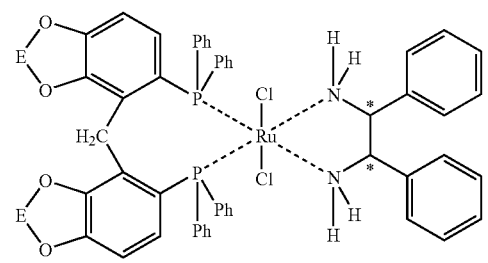
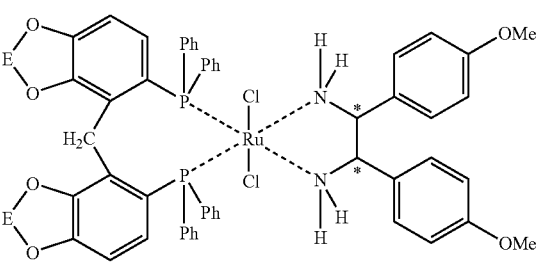
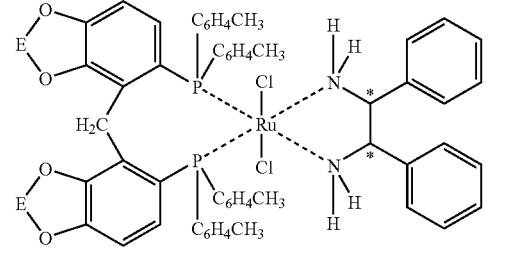
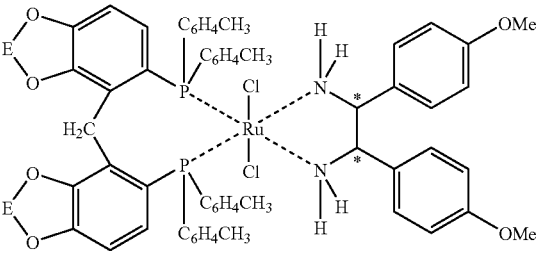
-continued
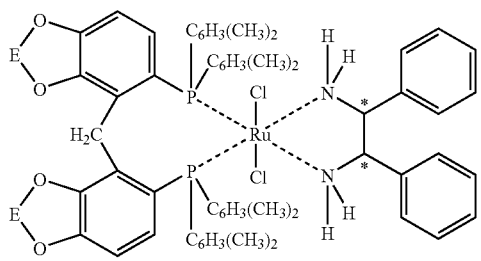
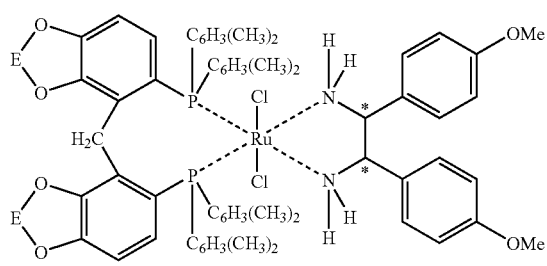
E: —CH$_2$—, —CH$_2$CH$_2$—, —CH$_2$CH$_2$CH$_2$—, —CH$_2$CH(CH$_3$)—
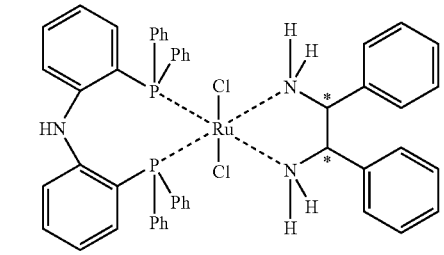
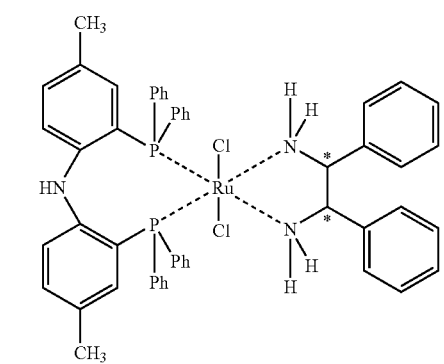
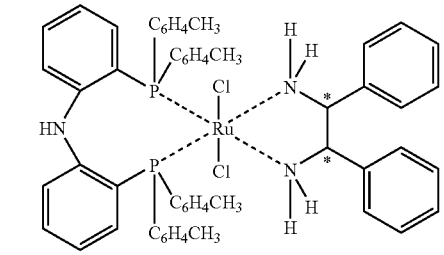

-continued
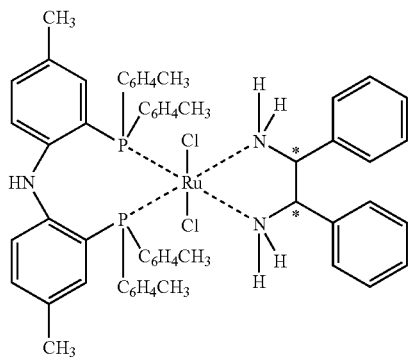
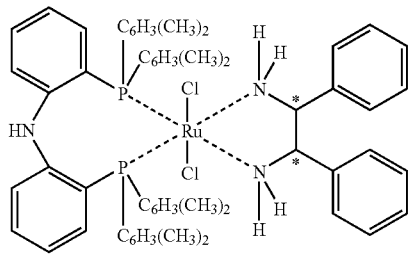
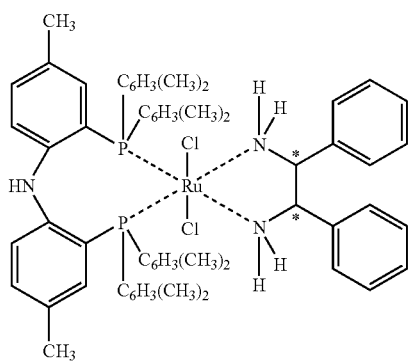
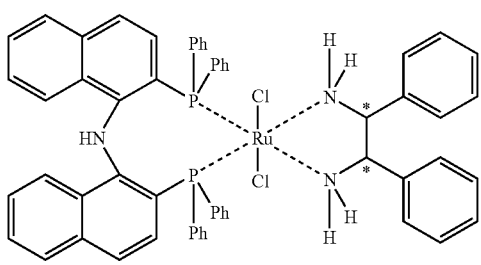
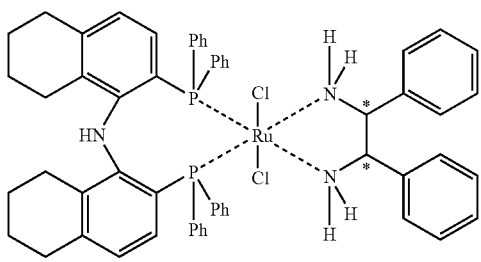
-continued
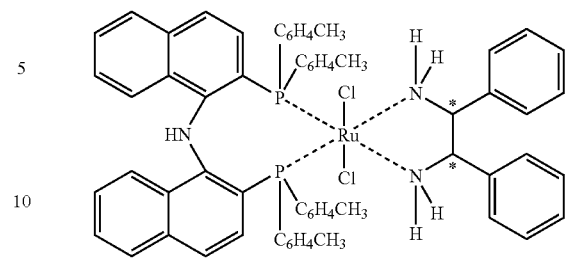
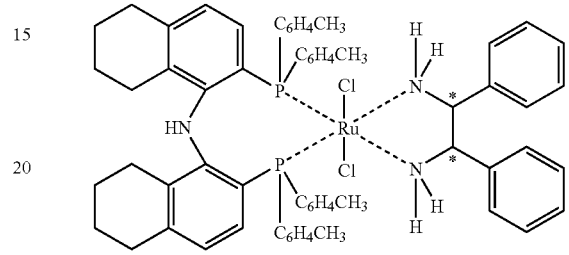
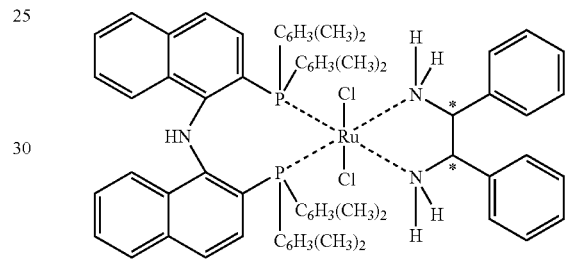
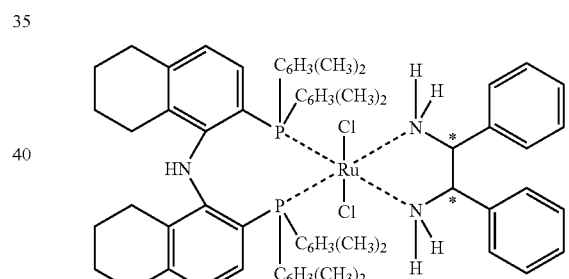
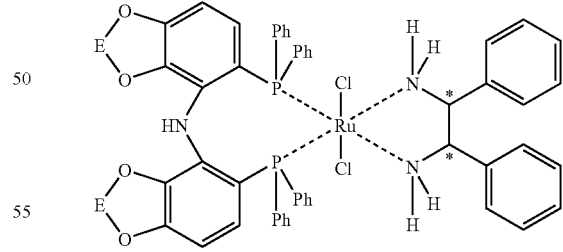
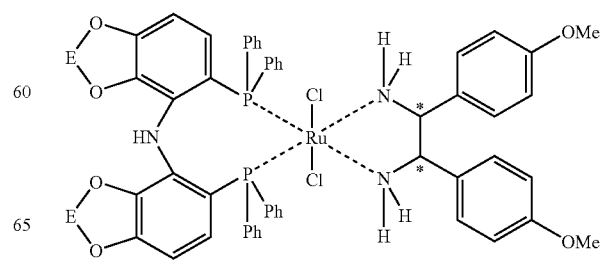

-continued
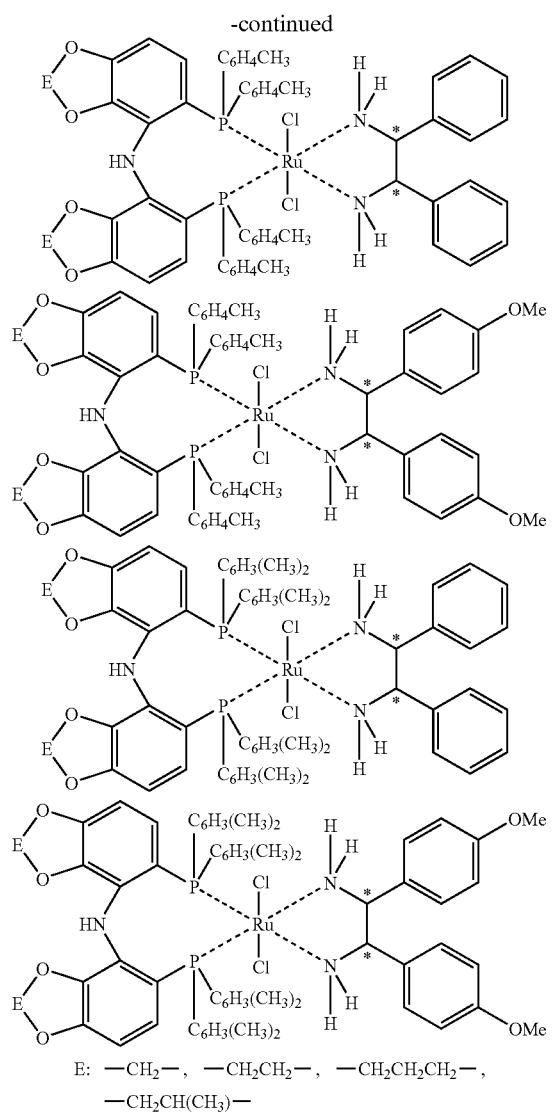
E: —CH$_2$—, —CH$_2$CH$_2$—, —CH$_2$CH$_2$CH$_2$—, —CH$_2$CH(CH$_3$)—
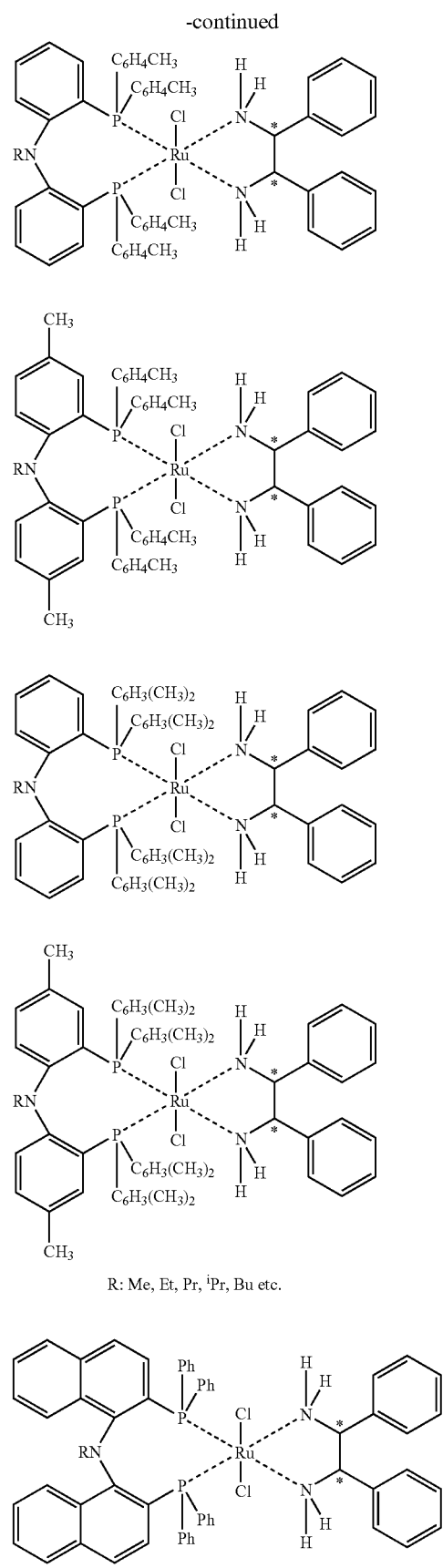
R: Me, Et, Pr, $^i$Pr, Bu etc.

-continued
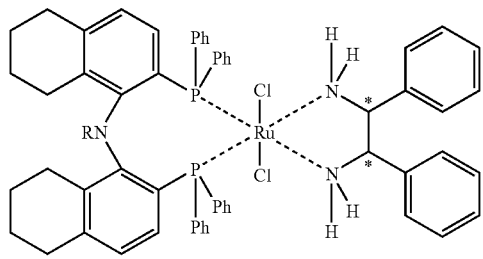
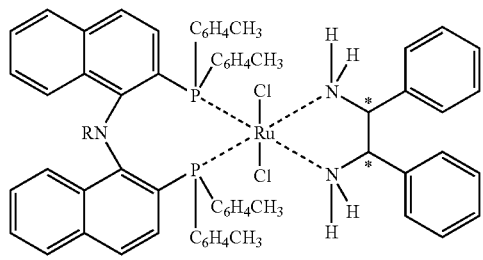
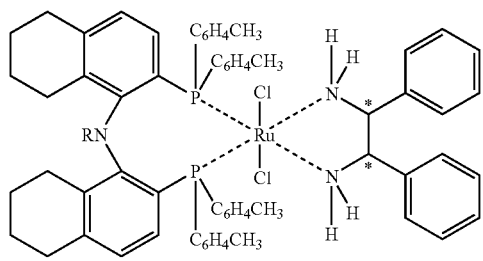
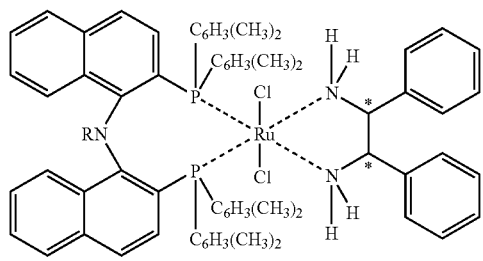
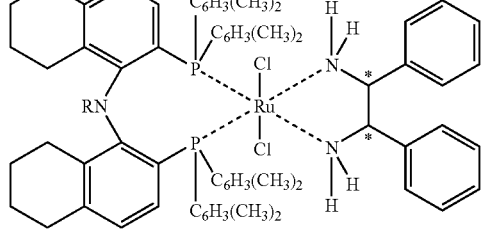
R: Me, Et, Pr, ⁱPr, Bu etc.
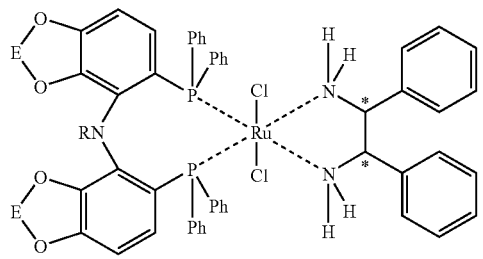
-continued
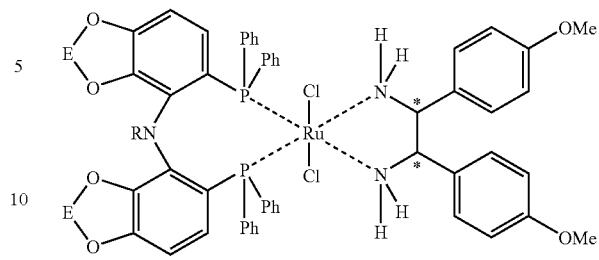
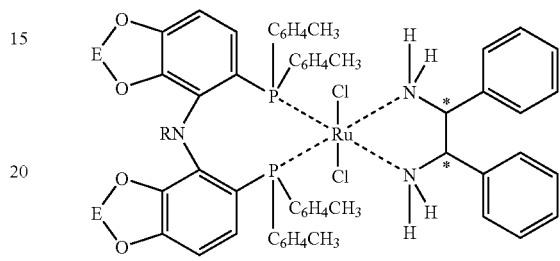
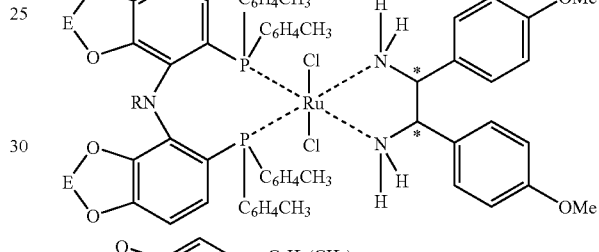
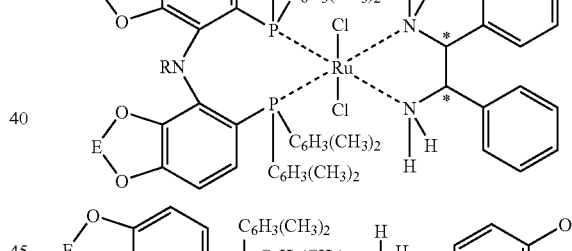
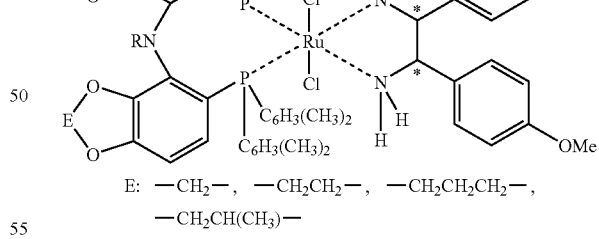
E: —CH$_2$—, —CH$_2$CH$_2$—, —CH$_2$CH$_2$CH$_2$—, —CH$_2$CH(CH$_3$)—
R: Me, Et, Pr, ⁱPr, Bu etc.
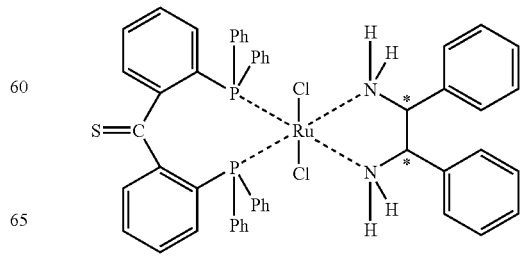

-continued
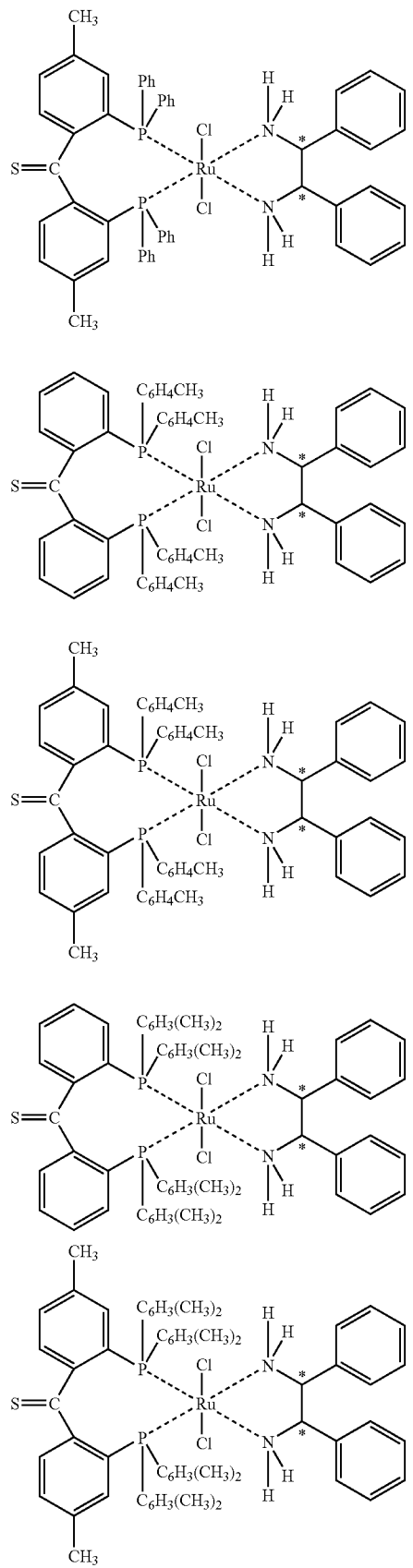
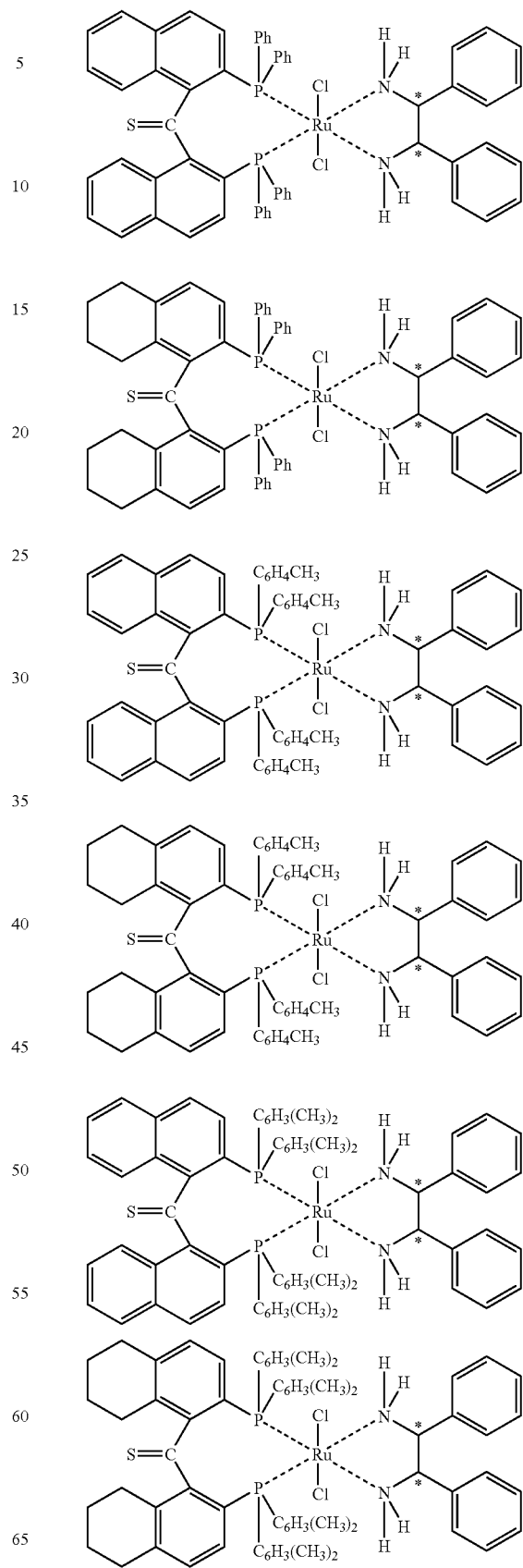

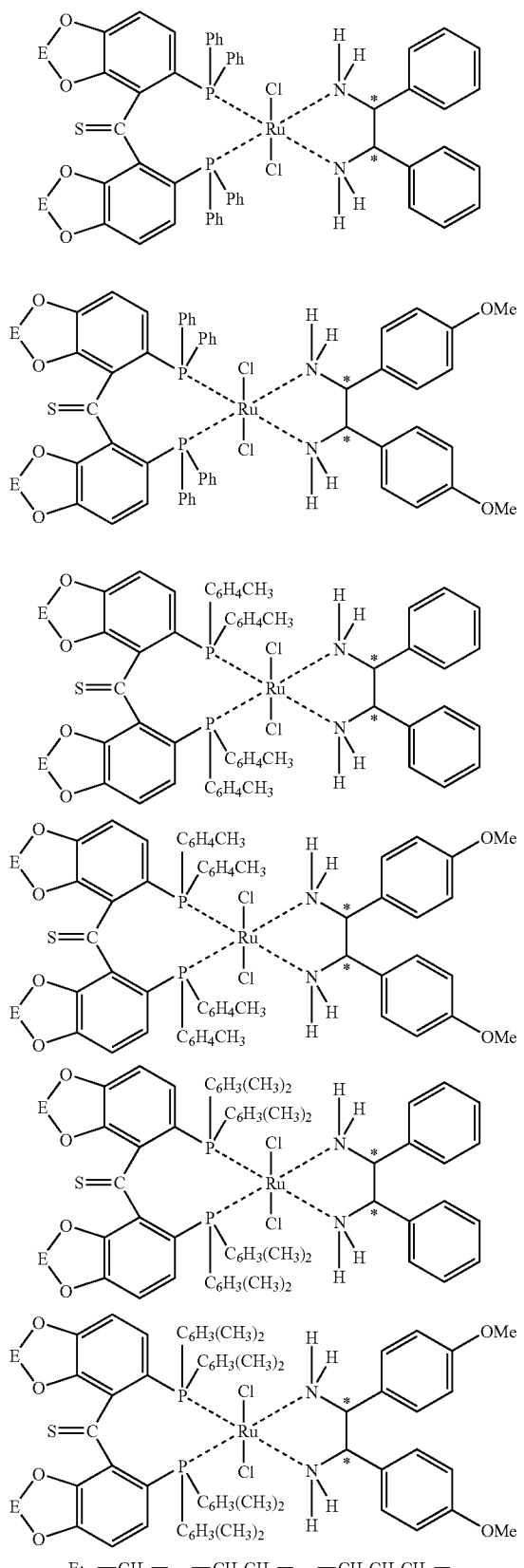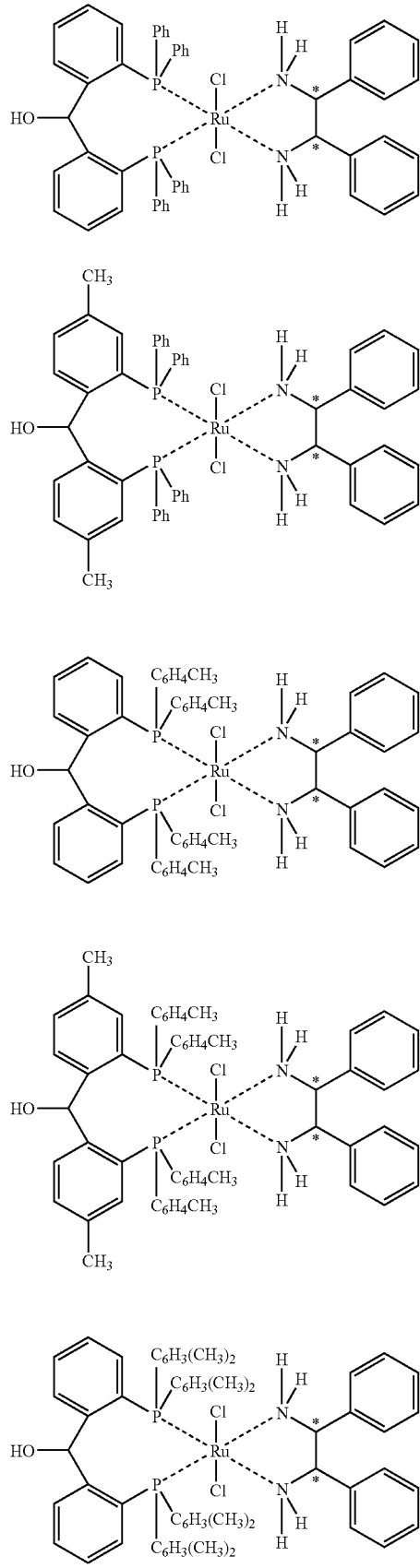
E: —CH$_2$—, —CH$_2$CH$_2$—, —CH$_2$CH$_2$CH$_2$—, —CH$_2$CH(CH$_3$)—

-continued
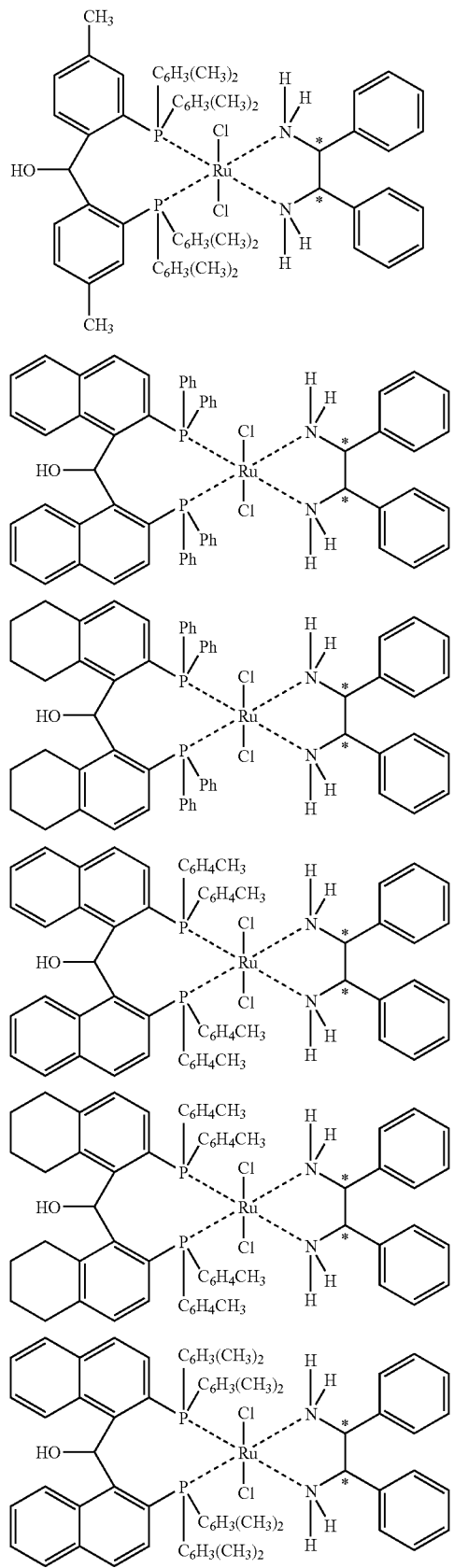
-continued
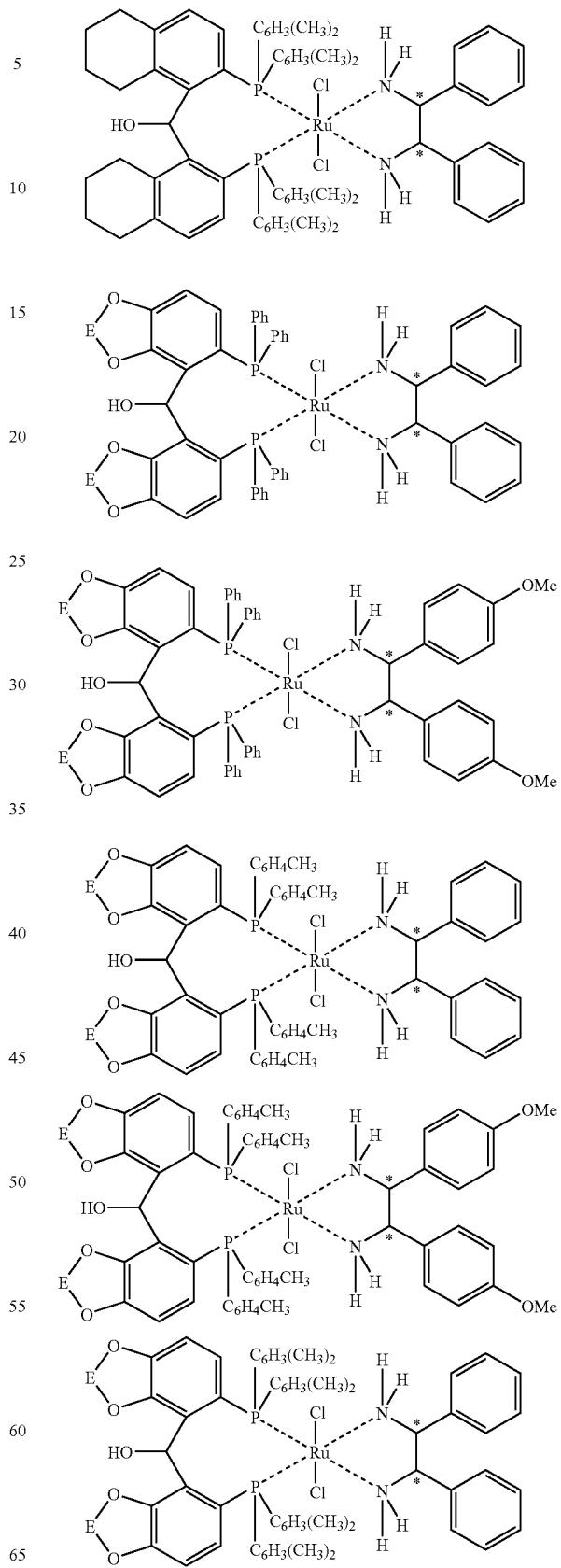

-continued
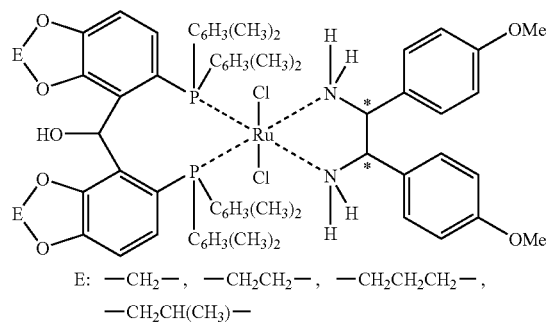
E: —CH₂—, —CH₂CH₂—, —CH₂CH₂CH₂—, —CH₂CH(CH₃)—
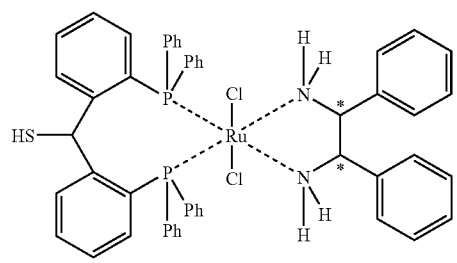
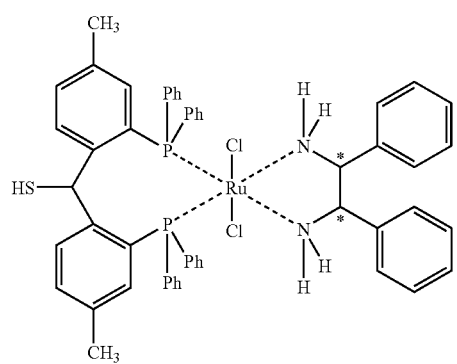
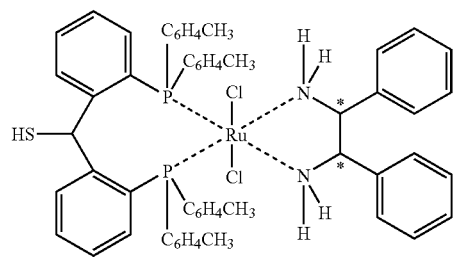
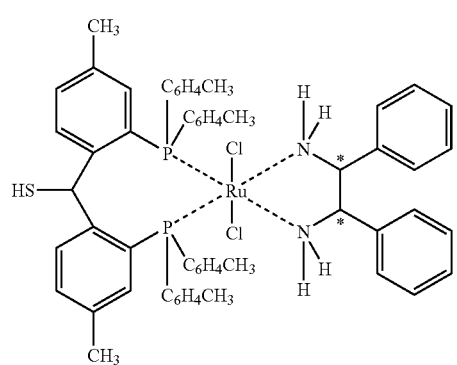
-continued
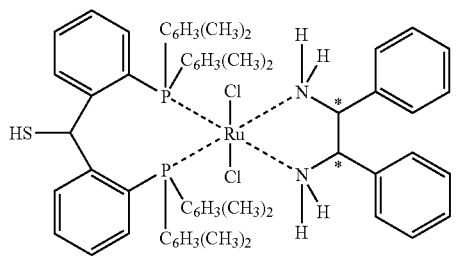
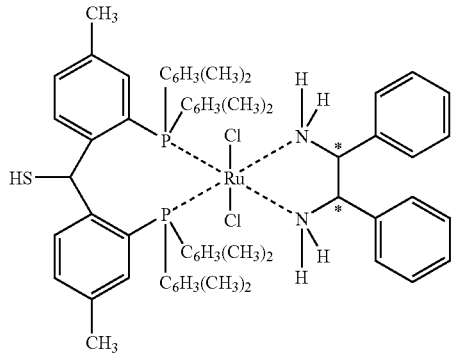
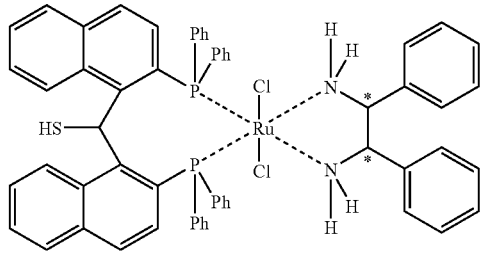
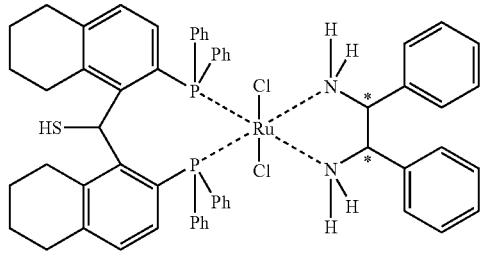
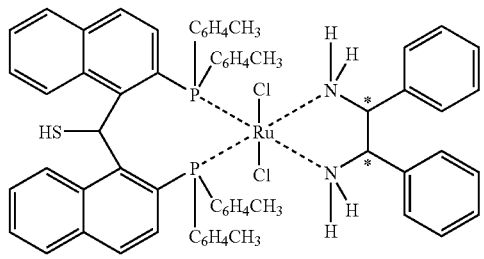
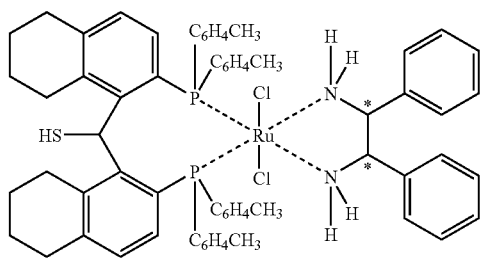

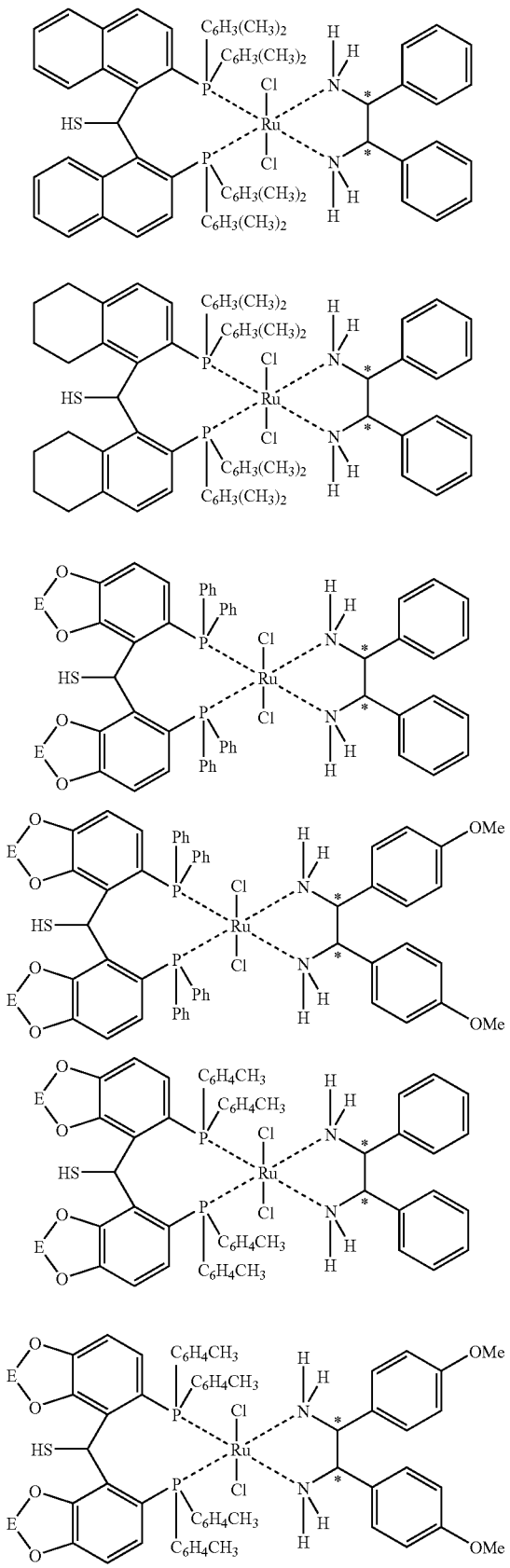

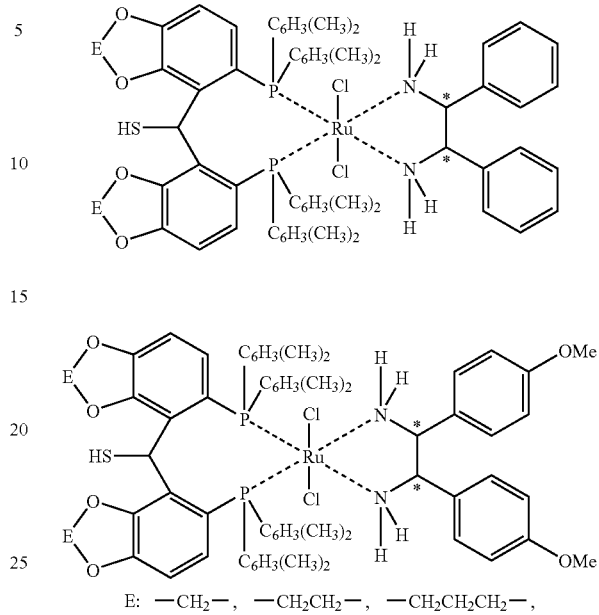

E: —CH$_2$—, —CH$_2$CH$_2$—, —CH$_2$CH$_2$CH$_2$—,
—CH$_2$CH(CH$_3$)—

Specific examples of the optically active rhodium diamine complex represented by the above-mentioned formula [1-4a] include the following compound:

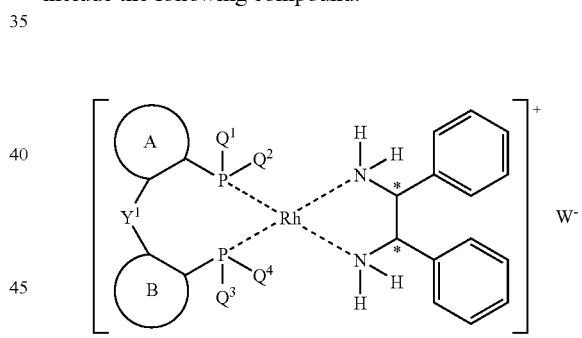

In the present invention, the following more specifically describes a process for producing a transition metal complex represented by the formula [1], which comprises a compound represented by the above-mentioned formula [2] and a compound represented by the above-mentioned formula [3] by taking a ruthenium phosphine diamine complex represented by the above-mentioned formula [1-1] as an example.

For example, the ruthenium phosphine diamine complex represented by the above-mentioned formula [1-1] can be produced by a process described in, e.g., J. Chem. Soc., Chem. Commun., 1208 (1989); J. Chem. Soc., Perkin. Trans., 2309 (1994); and JP-A-H10-120692.

The following describes one example of the process for producing the ruthenium phosphine diamine complex represented by the formula [1-1].

(1) Production of the Compound Represented by the Above-Mentioned Formula [2]

(1-1) First, a Compound Represented by the Formula [6]:

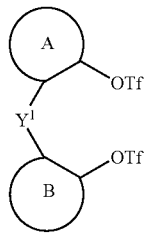

[6]

wherein Tf represents a trifluoromethanesulfonyl group, ring A and ring B, and $Y^1$ are the same as described above, preferably a compound represented by the formula [6-1]:

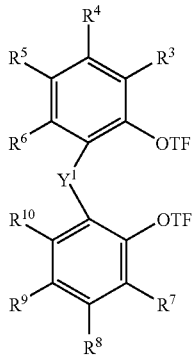

[6-1]

wherein $R^3$, $R^4$, $R^5$, $R^6$, $R^7$, $R^8$, $R^9$, and $R^{10}$, Tf, and $Y^1$ are the same as described above, can be prepared by triflation to react with trifluoromethanesulfonic acid anhydride or trifluoromethanesulfonyl chloride and a dihydroxy compound represented by the formula [5]:

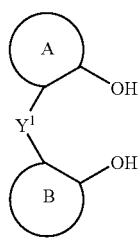

[5]

wherein ring A and ring B, and $Y^1$ are the same as described above, preferably a dihydroxy compound represented by the formula [5-1]:

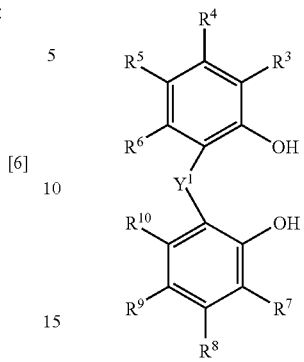

[5-1]

wherein $R^3$, $R^4$, $R^5$, $R^6$, $R^7$, $R^8$, $R^9$ and $R^{10}$, and $Y^1$ are the same as described above, in the presence of a base in an suitable solvent at 0 to 10° C. for 8 to 12 hours.

The base used in the above-mentioned reaction may be an inorganic base or organic base.

Examples of the organic base include organic amines such as triethylamine, diisopropylethylamine, N,N-dimethylaniline, piperidine, pyridine, 4-dimethylaminopyridine, 1,5-diazabicyclo[4.3.0]non-5-ene, 1,8-diazabicyclo[5.4.0]undec-7-ene, tri-n-butylamine, tetramethylethylenediamine, and N-methylmorpholine; alkali or alkaline earth metal salts such as potassium methoxide, sodium methoxide, lithium methoxide, sodium ethoxide, potassium isopropoxide, potassium tert-butoxide, lithium methoxide, and potassium naphthalenide.

Examples of the inorganic base include potassium carbonate, potassium hydroxide, lithium hydroxide, sodium hydrogencarbonate, sodium carbonate, potassium hydrogencarbonate, and sodium hydroxide.

The amount of the base used is appropriately selected usually from the range of 2.3 to 3.5 mols, preferably from the range of 2.5 to 2.7 mols per mole of the dihydroxy compound.

Examples of the solvent used in the reaction include halogenated hydrocarbons such as dichloromethane, 1,2-dichloroethane, chloroform, carbon tetrachloride, and o-dichlorobenzene; aliphatic hydrocarbons such as pentane, hexane, heptane, octane, decane, and cyclohexane; aromatic hydrocarbons such as benzene, toluene, and xylene; ethers such as diethyl ether, diisopropyl ether, tert-butyl methyl ether, dimethoxyethane, ethylene glycol diethyl ether, tetrahydrofuran, 1,4-dioxane, and 1,3-dioxolane; and esters such as methyl acetate, ethyl acetate, n-butyl acetate, and methyl propionate. These solvents may be used alone or in combination of two or more thereof.

The amount of the solvent used is appropriately selected usually from the range of 3 to 10 mL, preferably from the range of 5 to 7 mL per 1 mmol of the dihydroxy compound.

(1-2) Phosphinylation of the compound represented by the formula [6] obtained in the (1-1) is carried out. Said phosphinylation reaction can be carried out by a method described in, for example, "Jikken Kagaku Kohza (Experimental Chemistry Lecture)", 4th edition, vol. 25, Chapter 11 (in particular pp. 389-427), edited by the Japanese Chemical Society, 1991, Maruzen Co. Ltd.

That is, the resultant compound represented by the formula [6] is reacted with a phosphine oxide represented by the formula [7-1]:

$P(O)(Q^1Q^2)$            [7-1]

or the formula [7-2]:

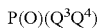

P(O)(Q³Q⁴)  [7-2]

wherein $Q^1$, $Q^2$, $Q^3$, and $Q^4$ are the same as described above, in the presence of a transition metal compound and a tertiary phosphine in an appropriate solvent usually at 90 to 120° C., preferably at 100 to 105° C. usually for 12 to 36 hours, preferably for 15 to 18 hours, to obtain a compound represented by the formula [8]:

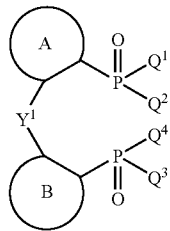

wherein ring A and ring B, $Y^1$, and $Q^1$, $Q^2$, $Q^3$, and $Q^4$ are the same as described above, preferably a compound represented by the formula [8-1]:

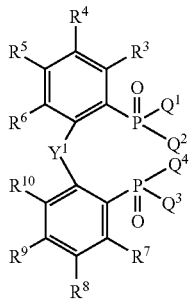

wherein $R^3$, $R^4$, $R^5$, $R^6$, $R^7$, $R^8$, $R^9$ and $R^{10}$, $Y^1$, and $Q^1$, $Q^2$, $Q^3$, and $Q^4$ are the same as described above.

At this point, when the phosphine oxide represented by the above-mentioned formula [7-1] is used as the phosphine oxide, the resultant compound represented by formula [8] is a compound wherein $Q^1=Q^3$ and $Q^2=Q^4$ in the formula [8]. When a phosphine oxide represented by the above-mentioned formula [7-2] is used, a similar compound can be obtained. Furthermore, it is allowable to use a phosphine oxide represented by the above-mentioned formula [7-1] to subject one of the TfO groups to phosfinylation, and subsequently use a phosphine oxide represented by the above-mentioned formula [7-2] to subject the other to phosfinylation.

Examples of the transition metal compound used in the above-mentioned reaction include palladium acetate, palladium chloride, and palladium triphenylphosphine. These transition metal compounds may be used alone or in combination of two or more thereof.

The amount of the transition metal compound used is appropriately selected usually from the range of 0.08 to 0.20 mmol, preferably from the range of 0.10 to 0.12 mmol per 1 mmol of the triflated compound.

The tertiary phosphine, if necessary, may be used in accordance with the kind of the used transition metal compound. Examples of the tertiary phosphine include triphenylphosphine, tri-t-butyl phosphine, 1,4-bis(diphenylphosphino)butane, 1,2-bis(diphenylphosphino)ethane, and 1,1-bis(diphenylphosphino)ferrocene.

The amount of the tertiary phosphine used is appropriately selected usually from the range of 2.5 to 3.5 mmol, preferably from the range of 2.8 to 3.2 mmol per 1 mmol of the triflate compound.

Examples of the used solvent include aliphatic hydrocarbons such as pentane, hexane, heptane, octane, decane, and cyclohexane; aromatic hydrocarbons such as benzene, toluene, and xylene; halogenated hydrocarbons such as dichloromethane, 1,2-dichloroethane, chloroform, carbon tetrachloride, and o-dichlorobenzene; ethers such as diethyl ether, diisopropyl ether, tert-butyl methyl ether, dimethoxyethane, ethylene glycol diethyl ether, tetrahydrofuran, 1,4-dioxane, and 1,3-dioxolane; ketones such as acetone, methyl ethyl ketone, methyl isobutyl ketone, and cyclohexanone; alcohols such as methanol, ethanol, 2-propanol, n-butanol, 2-ethoxyethanol, and benzyl alcohol; polyhydric alcohols such as ethylene glycol, propylene glycol, 1,2-propanediol, and glycerin; esters such as methyl acetate, ethyl acetate, n-butyl acetate, and methyl propionate; amides such as formamide, N,N-dimethylformamide, and N,N-dimethylacetoamide; sulfoxides such as dimethylsulfoxide; cyano-containing organic compounds such as acetonitrile; N-methylpyrrolidone; and water. These solvents may be used alone or in combination of two or more thereof.

The amount of the solvent used is appropriately selected usually from the range of 3 to 10 mL, preferably from the range of 4 to 6 mL per 1 mmol of the triflate compound.

It is usually preferred to conduct the phosphinylation in the presence of a base. Examples of the base are identical with the above-mentioned bases.

The amount of the base used is appropriately selected usually from the range of 3.5 to 4.5 mmol, preferably from the range of 3.8 to 4.2 mmol per 1 mmol of the triflate compound.

(1-3) The compound represented by the formula [8], preferably the compound represented by the formula [8-1], which is obtained in the (1-2), is subjected to reductive reaction by action of a reducing agent, thereby making it possible to obtain the target compound represented by the formula [2], preferably the compound represented by the formula [2-1].

An reducing agent used at this time is, for example, trichlorosilane.

The amount of the reducing agent used is appropriately selected usually from the range of 8 to 15 mmol, preferably from the range of 10 to 12 mmol per 1 mmol of the compound represented by the formula [8] or [8-1]. It is usually preferred to conduct the reductive reaction in the presence of a base. Examples of the base are identical with the above-mentioned bases. The amount of the base used is appropriately selected usually from the range of 35 to 45 mmol, preferably from the range of 40 to 42 mmol per 1 mmol of the compound represented by the formula [8] or [8-1].

The reductive reaction may be conducted in the presence of a solvent if necessary. Examples of the solvent include aliphatic hydrocarbons such as pentane, hexane, heptane, octane, decane, and cyclohexane; aromatic hydrocarbons such as benzene, toluene, and xylene; halogenated hydrocarbons such as dichloromethane, 1,2-dichloroethane, chloroform, carbon tetrachloride, and o-dichlorobenzene; ethers such as diethyl ether, diisopropyl ether, tert-butyl methyl ether, dimethoxyethane, ethylene glycol diethyl ether, tetrahydrofuran, 1,4-dioxane, and 1,3-dioxolane; alcohols such as methanol, ethanol, 2-propanol, n-butanol, 2-ethoxyethanol, and benzyl alcohol; polyhydric alcohols such as ethylene glycol, propylene glycol, 1,2-propanediol, and glycerin;

esters such as methyl acetate, ethyl acetate, n-butyl acetate, and methyl propionate; amides such as formamide, N,N-dimethylformamide, and N,N-dimethylacetoamide; sulfoxides such as dimethylsulfoxide; cyano-containing organic compounds such as acetonitrile; and N-methylpyrrolidone. These solvents may be used alone or in combination of two or more thereof.

The amount of the solvent used is appropriately selected usually from the range of 8 to 15 mL, preferably from the range of 10 to 12 mL per 1 mmol of the compound represented by the formula [8] or [8-1].

Of thus-produced compounds represented by the formula [2] of the present invention, a preferred compound is a compound represented by the following formula [2']:

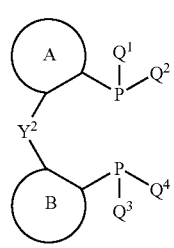

[2']

wherein ring A and ring B each independently represent an aromatic ring which may have a substituent, $Q^1$, $Q^2$, $Q^3$, and $Q^4$ each independently represent an aryl group which may have a substituent or an alicyclic group which may have a substituent, $Y^2$ represents a carbonyl group (C=O), a sulfonyl group ($SO_2$), a thiocarbonyl group (C=S), —CH(OH)— or —CH(SH)—. A more preferred compound thereof is a compound represented by the above-mentioned formula [2'-1] wherein the ring A and ring B in the above-mentioned formula [2'] are each a phenyl group which may have a substituent. Examples of the said substituent in the phenyl group are the above-mentioned substituents.

(2) Production of the Transition Metal Complex Represented by the Formula [1], for Example, the Ruthenium Diphosphine Complex Represented by the Formula [1-1].

The compound represented by the formula [2] or [2-1] and obtained in the above (1), preferably the compound represented by the formula [2'] or [2'-1] may be reacted with a transition metal compound represented by the following formula [9]:

[9]

wherein M, X and $Z^2$ are the same as described above, a represents 2 or 3, b represents 0 or 1, and c represents 1 or 2, to produce the compound represented by the formula [4].

For example, it is caused to react with a ruthenium complex represented by the following formula [10] wherein the transition metal of M is ruthenium in the above-mentioned formula [10]:

[10]

wherein $X^1$ and $X^2$ each represent a halogen atom, which is the same as described above, $Z^2$ and m are the same as described above, optionally in an appropriate solvent, thereby making it possible to obtain a transition metal compound wherein the transition metal M of the transition metal compound represented by the above-mentioned formula [4] is ruthenium.

Next, the resultant transition metal compound represented by the formula [4] is may be reacted with the compound represented by the above-mentioned formula [3], optionally in an appropriate solvent to obtained the transition metal complex of the invention represented by the above-mentioned formula [1].

Preferred specific examples of the transition metal compound represented by the formula [9] wherein the transition metal M is ruthenium, rhodium, iridium or the like include ruthenium complexes such as [$RuCl_2$(benzene)]$_2$, [$RuBr_2$(benzene)]$_2$, [$RuI_2$(benzene)]$_2$, [$RuCl_2$(p-cymene)]$_2$, [$RuBr_2$(p-cymene)]$_2$, [$RuI_2$(p-cymene)]$_2$, [$RuCl_2$(hexamethylbenzene)]$_2$, [$RuBr_2$(hexamethylbenzene)]$_2$, [$RuI_2$(hexamethylbenzene)]$_2$, [$RuCl_2$(mesitylene)]$_2$, [$RuBr_2$(mesitylene)]$_2$, [$RuI_2$(mesitylene)]$_2$, [$RuCl_2$(pentamethylcyclopentadiene)]$_2$, [$RuBr_2$(pentamethylcyclopentadiene)]$_2$, [$RuI_2$(pentamethylcyclopentadiene)]$_2$, [$RuCl_2$(cod)]$_2$, [$RuBr_2$(cod)]$_2$, [$RuI_2$(cod)]$_2$, [$RuCl_2$(nbd)]$_2$, [$RuBr_2$(nbd)]$_2$, [$RuI_2$(nbd)]$_2$, $RuCl_3$ hydrate, $RuBr_3$ hydrate, $RuI_3$ hydrate and [$RhCl_2$(cyclopentadiene)]; rhodium complexes such as [$RhBr_2$(cyclopentadiene)]$_2$, [$RhI_2$(cyclopentadiene)]$_2$, [$RhCl_2$(pentamethylcyclopentadiene)]$_2$, [$RhBr_2$(pentamethylcyclopentadiene)]$_2$, [$RhI_2$(pentamethylcyclopentadiene)]$_2$, [$RhCl_2$(cod)]$_2$, [$RhBr_2$(cod)]$_2$, [$RhI_2$(cod)]$_2$, [$RhCl_2$(nbd)]$_2$, [$RhBr_2$(nbd)]$_2$, [$RhI_2$(nbd)]$_2$, $RhCl_3$ hydrate, $RhBr_3$ hydrate, and $RhI_3$ hydrate; and iridium complexes such as [$IrCl_2$(cyclopentadiene)]$_2$, [$IrBr_2$(cyclopentadiene)]$_2$, [$IrI_2$(cyclopentadiene)]$_2$, [$IrCl_2$(pentamethylcyclopentadiene)]$_2$, [$IrBr_2$(pentamethylcyclopentadiene)]$_2$, [$IrI_2$(pentamethylcyclopentadiene)]$_2$, [$IrCl_2$(cod)]$_2$, [$IrBr_2$(cod)]$_2$, [$IrI_2$(cod)]$_2$, [$IrCl_2$(nbd)]$_2$, [$IrBr_2$(nbd)]$_2$, [$IrI_2$(nbd)]$_2$, $IrCl_3$ hydrate $IrBr_3$ hydrate, and $IrI_3$ hydrate. In the formulae, cod represents 1,5-cyclooctadiene, and nbd represents norbornadiene.

In the case that an aromatic diamine is used as the compound represented by the above-mentioned formula [3] for producing the transition metal complex represented by the formula [1] of the present invention, the ruthenium phosphine diamine complex represented by the above-mentioned formula [1-1], the rhodium phosphine diamine complex represented by the above-mentioned formula [1-2], or the like is obtained.

Also, when an optically active aromatic diamine is used as the aromatic diamine, an optically active transition metal complex corresponding to the transition metal complex of the above-mentioned formula [1], for example, an optically active ruthenium phosphine diamine complex represented by the above-mentioned formula [1-1a] or an optically active rhodium phosphine diamine complex represented by the above-mentioned formula [1-2a] is obtained.

The amounts of the compound represented by the formula [2] and the metal compound represented by the formula [4] used are appropriately selected from such a range that the amount of the metal compound represented by the formula [4] is usually from 1.0 to 1.1 mmol, preferably from 1.0 to 1.05 mmol per 1 mmol of the compound represented by the formula [2].

The amount of the compound represented by the above-mentioned formula [3] used is appropriately selected usually from the range of 1.0 to 1.1 mmol, preferably from the range of 1.0 to 1.05 mmol per 1 mmol of the transition metal compound represented by the formula [4].

Also, when the ligand is the aromatic diamine, the amount of the aromatic diamine used is appropriately selected usually from the range of 1.0 to 1.1 mmol, preferably from the range of 1.0 to 1.5 mmol per 1 mmol of the transition metal compound represented by the formula [4].

The present reaction is preferably conducted in the presence of a solvent. Examples of the used solvent include aromatic hydrocarbons such as benzene, toluene, and xylene; halogenated hydrocarbons such as dichloromethane, 1,2-dichloroethane, chloroform, carbon tetrachloride, and o-dichlorobenzene; and alcohols such as methanol, ethanol, 2-propanol, n-butanol, 2-ethoxyethanol, and benzyl alcohol. These solvents may be used alone or in combination of two or more thereof.

The amount of the solvent used is appropriately selected usually from the range of 0.8 to 1.5 mmol, preferably from the range of 1.0 to 1.1 mmol for 0.1 mmol of the compound represented by the formula [2].

The reaction temperature is not particularly limited since the temperature is varied in accordance with the kind of the compound represented by the formula [2] or the transition metal compound represented by the formula [4], or others. The temperature is appropriately selected usually from 90 to 105° C., preferably from 95 to 100° C.

The reaction time is not particularly limited since the time is varied in accordance with the kind of the compound represented by the formula [2] or the transition metal compound represented by the formula [4], or others. The time is appropriately selected usually from 15 to 60 minutes, preferably from 30 to 40 minutes.

When the ligand is the aromatic diamine, the reaction which is conducted in an inert gas atmosphere is also a preferred embodiment. Examples of the inert gas include nitrogen gas, and argon gas.

The reaction temperature in the case that the ligand is the aromatic diamine is not particularly limited since the temperature is varied in accordance with the kind of the used ruthenium complex or aromatic diamine, or others. The temperature is appropriately selected usually from 90 to 110° C., preferably from 95 to 105° C.

The reaction time is not particularly limited since the time is varied in accordance with the kind of the used ruthenium complex or aromatic diamine, or others. The time is appropriately selected usually from 15 to 60 minutes, preferably from 30 to 40 minutes.

Thus obtained transition metal complex represented by the formula [1] of the present invention is useful as a catalyst, for example, hydrogenation, or the like. Among the transition metal complexes represented by the formula [1] of the present invention, the optically active transition metal complex produced by use of the optical active diamine is useful as a catalyst for asymmetric synthesis, for example, asymmetric hydrogenation. For example, the optically active ruthenium phosphine diamine complex represented by the above-mentioned formula [1-1a] or the optically active rhodium phosphine diamine complex represented by the above-mentioned formula [1-2a] is, in particular, useful as an asymmetric catalyst such as an asymmetric hydrogenation catalyst and the like.

Also, in the transition metal compound represented by the formula [4], for example, the ruthenium phosphine compound wherein the transition metal M is ruthenium, the ligand represented by $Z^2$ is a neutral ligand. Such compound is used in combination with the aromatic diamine, preferably the optically active aromatic diamine, whereby the combination can be effectively used as an asymmetric catalyst composition such as an asymmetric hydrogenation catalyst composition and the like. This would be because the transition metal complex of the invention represented by the formula [1] is produced in situ in a reaction system where both of the transition metal compound of the formula [4] and the diamine compound of the formula [3] are present.

Similarly, in the case of the transition metal compound represented by the formula [4], for example, the ruthenium phosphine compound represented thereby, which is obtained by reacting the compound represented by the above-mentioned formula [2] with the transition metal compound represented by the formula [9], for example, the ruthenium complex represented by the formula [10] wherein transition metal M is ruthenium, and a compound which can become a ligand of the transition metal such as ruthenium and the like, the present compound which is used in combination with the aromatic diamine, preferably the optically active aromatic diamine, can be effectively used as a hydrogenation catalyst, preferably an asymmetric catalyst composition such as an asymmetric hydrogenation catalyst composition and the like.

The process for producing the metal complex of the present invention has been described about ruthenium complexes. However, metal complexes of metals other than ruthenium can also be produced in conformity with the case of ruthenium.

For example, in the case of rhodium complexes, an appropriate rhodium or iridium as described above is used instead of the above-mentioned ruthenium as the metal complex of the above-mentioned formula [4], whereby a corresponding rhodium phosphine diamine complex or iridium phosphine diamine complex can be produced in the same way.

The following describes a process for producing an optically active alcohol according to the present invention.

In the formula [11], the hydrocarbon group of the hydrocarbon group which may have a substituent and is represented by $R^1$ and $R^2$ include, for example, alkyl, alkenyl, alkynyl, aryl or aralkyl.

The alkyl group may be linear, branched or cyclic and examples thereof include, for example, an alkyl group having 1 to 15 carbon atoms, preferably 1 to 10 carbon atoms, or a cycloalkyl group having 3 to 15 carbon atoms, preferably 3 to 10 carbon atoms. Specific examples thereof include methyl, ethyl, n-propyl, isopropyl, n-butyl, 1-methylpropyl, isobutyl, tert-butyl, n-pentyl, 1-methylbutyl, tert-pentyl, 2-methylbutyl, 3-methylbutyl, 2,2-dimethylpropyl, n-hexyl, 1-methylpentyl, 1-ethylbutyl, tert-hexyl, 2-methylpentyl, 3-methylpentyl, 4-methylpentyl, 2-methylpentane-3-yl, heptyl, octyl, nonyl, decyl, cyclopropyl, cyclobutyl, cyclopentyl, and cyclohexyl.

The alkenyl group is, for example, a group wherein the above-mentioned alkyl group having 2 or more carbon atoms has one or more double bonds. More specific examples thereof include ethenyl, 1-propenyl, 2-propenyl, isopropenyl, 1-butenyl, 2-butenyl, 1,3-butadienyl, 2-pentenyl, and 2-hexenyl.

The alkynyl group is, for example, a group wherein the above-mentioned alkyl group having 2 or more carbon atoms has one or more triple bonds. More specific examples thereof include ethynyl, 1-propynyl, and 2-propynyl.

The aryl group includes, for example, 5- to 7-membered monocyclic, polycyclic, or condensed cyclic aryl groups having 6 to 14 carbon atoms. Specific examples thereof include phenyl, naphthyl, anthryl, and biphenyl.

The aralkyl group may be a group wherein at least one hydrogen atom of the above-mentioned alkyl group is substituted with the above-mentioned aryl group, for example, an aralkyl group having 7 to 12 carbon atoms. Specific examples thereof include benzyl, 2-phenylethyl, 1-phenylpropyl, and 3-naphthylpropyl.

The aliphatic heterocyclic group of the aliphatic heterocyclic group which may have a substituent is, for example, a 5- to 8-membered, preferably 5- or 6-membered, monocyclic aliphatic heterocyclic group, or polycyclic or condensed-ring aliphatic heterocyclic group which has 2 to 14 carbon atoms and contains at least one heteroatom, preferably 1 to 3 heteroatoms, such as nitrogen, oxygen or sulfur atoms, as heteroatoms. Specific examples of the aliphatic heterocyclic group include pyrrolidyl-2-one, piperidino, piperazinyl, morpholino, tetrahydrofuryl, and tetrahydropyranyl.

The aromatic heterocyclic group of the aromatic heterocyclic group which may have a substituent is, for example, a 5- to 8-membered, preferably 5- or 6-membered, monocyclic heteroaryl group, or polycyclic or condensed-ring heteroaryl group which has 2 to 15 carbon atoms and contains at least one heteroatom, preferably 1 to 3 heteroatoms, such as nitrogen, oxygen or sulfur atoms, as heteroatoms. Specific examples thereof include furyl, thienyl, pyridyl, pyrimidyl, pyrazyl, pyridazyl, pyrazolyl, imidazolyl, oxazolyl, thiazolyl, benzofuryl, benzothienyl, quinolyl, isoquinolyl, quinoxalyl, phthalazyl, quinazolyl, naphthyrizyl, cinnolyl, benzoimidazolyl, benzooxazolyl, and benzothiazolyl.

The substituent in the hydrocarbon group, the aliphatic heterocyclic group and the aromatic heterocyclic group include, for example, alkyl, aryl, alkoxy, aryloxy, aralkyloxy, alkoxycarbonyl, aryloxycarbonyl, aralkyloxycarbonyl, acyloxy, alkylthio, arylthio, aralkylthio, halogen, amino, substituted amino, cyano, nitro, hydroxyl, carboxyl, sulfo and alkylenedioxy.

Definitions of alkyl and aryl, and specific examples thereof are the same as described above.

The alkoxy group may be linear, branched or cyclic, and is, for example, an alkoxy group having 1 to 6 carbon atoms or a cycloalkyl group having 3 to 6 carbon atoms. Specific examples thereof include methoxy, ethoxy, n-propoxy, 2-propoxy, n-butoxy, 1-methylpropoxy, isobutoxy, tert-butoxy, n-pentyloxy, 2-methylbutoxy, 3-methylbutoxy, 2,2-dimethylpropyloxy, n-hexyloxy, 2-methylpentyloxy, 3-methylpentyloxy, 4-methylpentyloxy, 5-methylpentyloxy, and cyclohexyloxy.

The aryloxy group is, for example, an aryloxy group having 6 to 14 carbon atoms. Specific examples thereof include phenoxy, naphthyloxy, and anthryloxy.

The aralkyloxy group is, for example, an aralkyloxy group having 7 to 12 carbon atoms. Specific examples thereof include benzyloxy, 2-phenylethoxy, 1-phenylpropoxy, 2-phenylpropoxy, 3-phenylpropoxy, 1-phenylbutoxy, 2-phenylbutoxy, 3-phenylbutoxy, 4-phenylbutoxy, 1-phenylpentyloxy, 2-phenylpentyloxy, 3-phenylpentyloxy, 4-phenylpentyloxy, 5-phenylpentyloxy, 1-phenylhexyloxy, 2-phenylhexyloxy, 3-phenylhexyloxy, 4-phenylhexyloxy, 5-phenylhexyloxy, and 6-phenylhexyloxy.

The alkoxycarbonyl group may be linear, branched or cyclic, and is, for example, an alkoxycarbonyl group having 2 to 19 carbon atoms, or a cycloalkoxycarbonyl group having 3 to 19 carbon atoms, preferably 3 to 10 carbon atoms. Specific examples thereof include methoxycarbonyl, ethoxycarbonyl, n-propoxycarbonyl, 2-propoxycarbonyl, n-butoxycarbonyl, tert-butoxycarbonyl, pentyloxycarbonyl, hexyloxycarbonyl, 2-ethylhexyloxycarbonyl, lauroyloxycarbonyl, stearoyloxycarbonyl, and cyclohexyloxycarbonyl.

The aryloxycarbonyl group is, for example, an aryloxycarbonyl group having 7 to 20 carbon atoms. Specific examples thereof include phenoxycarbonyl, and naphthyloxycarbonyl.

The aralkyloxycarbonyl group is, for example, an aralkyloxycarbonyl group having 8 to 15 carbon atoms. Specific examples thereof include benzyloxycarbonyl, phenylethoxycarbonyl, and 9-fluorenylmethyloxycarbonyl.

The acyloxy group is, for example, an aliphatic or aromatic acyloxy group which is derived from a carboxylic acid and has 2 to 18 carbon atoms. Specific examples thereof include acetoxy, propionyloxy, butyryloxy, pivaroyloxy, pentanoyloxy, hexanoyloxy, lauroyloxy, stearoyloxy, and benzoyloxy.

The alkylthio group may be linear, branched or cyclic, and is, for example, an alkylthio group having 1 to 6 carbon atoms or a cycloalkylthio group having 3 to 6 carbon atoms. Specific examples thereof include methylthio, ethylthio, n-propylthio, 2-propylthio, n-butylthio, 1-methylpropyl, isobutylthio, tert-butylthio, pentylthio, hexylthio, and cyclohexylthio.

The arylthio group is, for example, an arylthio group having 6 to 14 carbon atoms. Specific examples thereof include phenylthio and naphthylthio.

The aralkylthio group is, for example, an aralkylthio group having 7 to 12 carbon atoms. Specific examples thereof include benzylthio, and 2-phenethylthio.

The halogen atoms include fluorine, chlorine, bromine, and iodine.

When the substituent is an alkylenedioxy group, adjacent two hydrogen atoms in the above-mentioned aryl group moiety are substituted with the alkylenedioxy. The alkylenedioxy group is, for example, a linear or branched alkylenedioxy group having 1 to 3 carbon atoms. Specific examples thereof include methylenedioxy, ethylenedioxy, and trimethylenedioxy.

The substituted amino group may be an amino group wherein one or two hydrogen atoms of the amino group is/are substituted with substituents such as a protective group. The protective group is not particularly limited if the group is used as the amino-protective group, and examples thereof include groups described as amino-protective groups in "PROTECTIVE GROUPS IN ORGANIC SYNTHESIS Second Edition (JOHN WILEY & SONS, INC.)". Specific examples of the amino-protective group include, for example, alkyl, aryl, aralkyl, acyl, alkoxycarbonyl, aryloxycarbonyl, and aralkyloxycarbonyl.

Definitions of alkyl, aryl, aralkyl, alkoxycarbonyl, aryloxycarbonyl, and aralkyloxycarbonyl, and specific examples thereof are the same as described above.

The acyl group may be linear or branched, and is, for example, an acyl group which is derived from a carboxylic acid such as an aliphatic carboxylic acid and aromatic carboxylic acid and has 1 to 18 carbon atoms. Specific examples thereof include formyl, acetyl, propionyl, butyryl, pivaroyl, pentanoyl, hexanoyl, lauroyl, stearoyl, and benzoyl.

Specific examples of the amino group substituted with the alkyl group, that is, the alkyl-substituted amino group include mono- or di-alkylamino groups such as N-methylamino, N,N-dimethylamino, N,N-diethylamino, N,N-diisopropylamino, and N-cyclohexylamino.

Specific examples of the amino group substituted with the aryl group, that is, the aryl-substituted amino group include mono- or di-arylamino groups such as N-phenylamino, N,N-diphenylamino, N-naphthylamino, and N-naphthyl-N-phenylamino.

Specific examples of the amino group substituted with the aralkyl group, that is, the aralkyl-substituted amino group include mono- or di-aralkyl substituted amino groups such as N-benzylamino, and N,N-dibenzylamino.

Specific examples of the amino group substituted with the acyl group, that is, the acylamino group include formylamino, acetylamino, propionylamino, pivaroylamino, pentanoylamino, hexanoylamino, and benzoylamino.

Specific examples of the amino group substituted with the alkoxycarbonyl group, that is, the alkoxycarbonylamino group include methoxycarbonylamino, ethoxycarbonylamino, n-propoxycarbonylamino, n-butoxycarbonylamino, tert-butoxycarbonylamino, pentyloxycarbonylamino, and hexyloxycarbonylamino.

The amino group substituted with the aryloxycarbonyl group, that is, the aryloxycarbonylamino group may be specifically the amino group wherein one hydrogen atom of an amino group is substituted with the above-mentioned aryloxycarbonyl group. Specific examples thereof include phenoxycarbonylamino, and naphthyloxycarbonylamino.

Specific examples of the amino group substituted with the aralkyloxycarbonyl group, that is, the aralkyloxycarbonylamino group include a benzyloxycarbonylamino.

The alkyl group substituted with the halogen atom, that is, the halogenated alkyl group may be a halogenated alkyl group having 1 to 15 carbon atoms, preferably 1 to 10 carbon atoms, more preferably 1 to 6 carbon atoms, wherein at least one hydrogen atom, preferably 1 to 3 hydrogen atoms of the above-mentioned alkyl group is halogenated (such as fluorinated, chlorinated, brominated and iodinated) with the halogen atom. Specific examples thereof include chloromethyl, bromomethyl, trifluoromethyl, 2-chloroethyl, 3-bromopropyl, and 3,3,3-trifluoropropyl.

The substituted aryl group may be an aryl group wherein at least one hydrogen atom of the above-mentioned aryl group is substituted with the above-mentioned substituent(s).

Specific examples of the aryl group substituted with the alkyl group include tolyl, and xylyl.

The substituted aralkyl group may be an aralkyl group wherein at least one hydrogen atom of the above-mentioned aralkyl group is substituted with the above-mentioned substituent(s).

The α,β-unsaturated alkyl group represented by $R^1$ include alkenyl or alkynyl.

The alkenyl group may be linear or branched, and is, for example, an alkenyl group having 2 to 15 carbon atoms, preferably 2 to 10 carbon atoms, more preferably 2 to 6 carbon atoms. Specific examples thereof include, for example, ethenyl, 1-propenyl, 2-propenyl, isopropenyl, 1-butenyl, 2-butenyl, 1,3-butadienyl, 2-pentenyl, and 2-hexenyl.

The alkynyl group may be linear or branched, and is, for example, an alkynyl group having 2 to 15 carbon atoms, preferably 2 to 10 carbon atoms, more preferably 2 to 6 carbon atoms. Specific examples thereof include, for example, ethynyl, 1-propynyl, 1-butynyl, 1-pentynyl, and 1-hexynyl.

Specific examples of the ketone represented by the formula [11] include, for example, methyl ethyl ketone, acetophenone, benzalacetone, 1-indanone, 3,4-dihydro-(2H)-naphthalenone ferrocenyl methyl ketone, and compounds represented by the following:

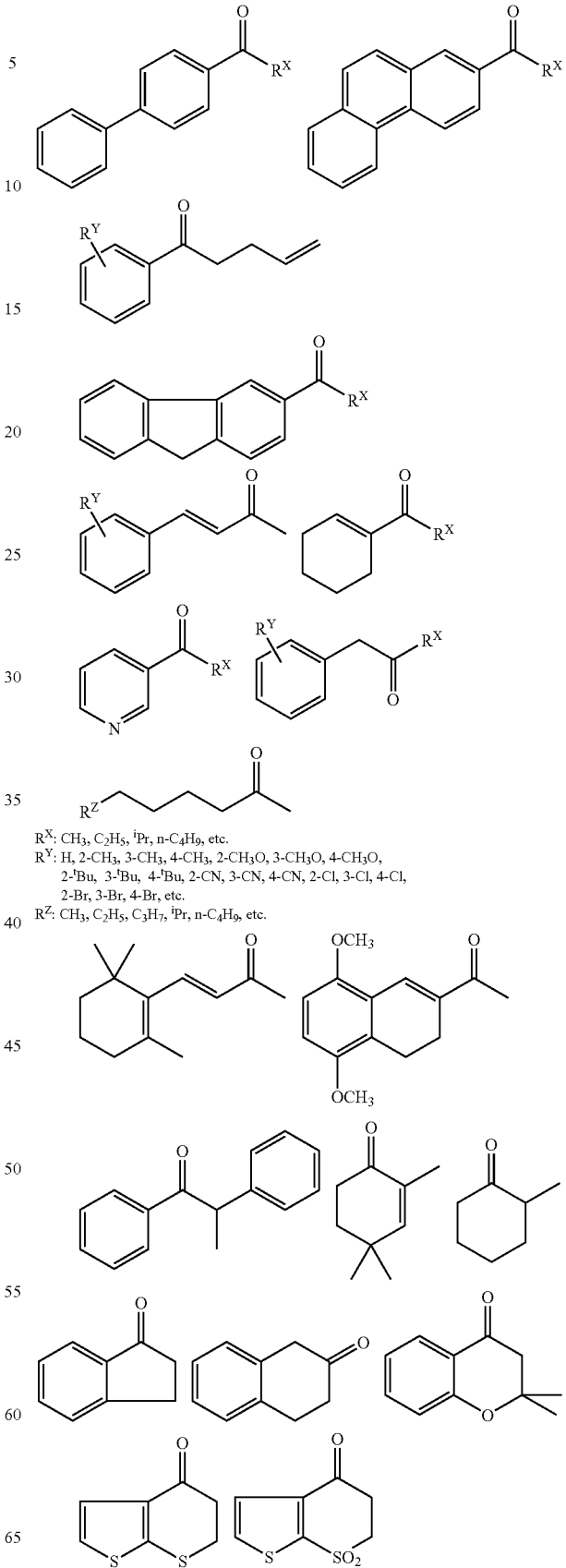

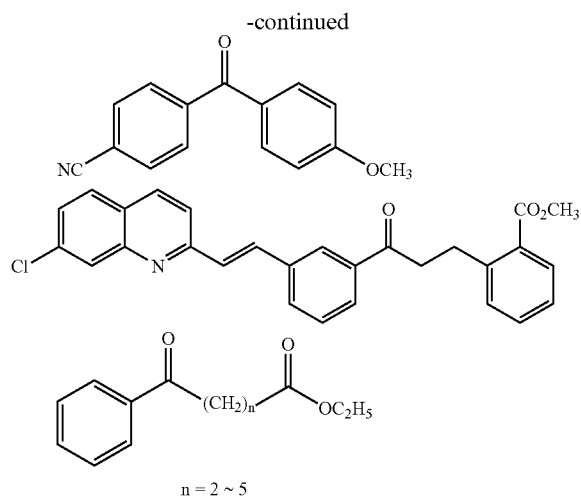

n = 2 ~ 5

The optically active alcohol represented by the above-mentioned formula [12] which is obtained by the production process of the present invention is an optically active secondary alcohol, and specific examples thereof include optically active alcohols derived from the compounds exemplified as the specific examples of the ketone represented by the above-mentioned formula [11], 2-butanol, and phenethyl alcohol.

In the process for producing the optically active alcohol of the present invention as described above, the transition metal complex represented by the formula [1], preferably the optically active transition metal complex represented by the formula [1] is used as a catalyst. Also, the asymmetric catalyst composition containing such as the transition metal compound represented by the above-mentioned formula [4] and the optically active compound represented by the formula [3] as described above can be used as a catalyst. The asymmetric hydrogenation using the latter asymmetric catalyst composition is a reaction which is performed in the reaction system therefor (in situ).

The process for producing the optically active alcohol of the present invention may be performed in a solvent, if necessary. The solvent wherein the ketone compound represented by the above-mentioned formula [11] and the asymmetric hydrogenation catalyst are dissolved is preferred.

Examples of the solvent include, for example, aliphatic hydrocarbons such as pentane, hexane, heptane, octane, decane, and cyclohexane; aromatic hydrocarbons such as benzene, toluene, and xylene; halogenated hydrocarbons such as dichloromethane, 1,2-dichloroethane, chloroform, carbon tetrachloride, and o-dichlorobenzene; ethers such as diethyl ether, diisopropyl ether, tert-butyl methyl ether, dimethoxyethane, ethylene glycol diethyl ether, tetrahydrofuran, 1,4-dioxane, and 1,3-dioxolane; alcohols such as methanol, ethanol, 2-propanol, n-butanol, 2-ethoxyethanol, and benzyl alcohol; polyhydric alcohols such as ethylene glycol, propylene glycol, 1,2-propanediol, and glycerin; amides such as N,N-dimethylformamide, and N,N-dimethylacetoamide; sulfoxides such as dimethylsulfoxide; cyano-containing organic compounds such as acetonitrile; and N-methylpyrrolidone. These solvents may be used alone or in combination of two or more thereof.

The amount of the solvent used is decided in accordance with the solubility of the ketone compound represented by the formula [11], which is a used reaction substrate, or economical efficiency. The amount of the solvent used is appropriately selected usually from the range of 5 to 50 weight %, preferably from the range of 10 to 40 weight %.

The process for producing the optically active alcohol of the present invention is preferably performed in the presence of a base. The base include an inorganic base and an organic base. Examples of the organic base include, for example, organic amines such as triethylamine, diisopropylethylamine, N,N-dimethylaniline, piperidine, pyridine, 4-dimethylaminopyridine, 1,5-diazabicyclo[4.3.0]non-5-ene, 1,8-diazabicyclo[5.4.0]undec-7-ene, tri-n-butylamine, tetramethylethylenediamine, and N-methylmorpholino; and alkali or alkaline earth metal salts such as potassium methoxide, sodium methoxide, lithium methoxide, sodium ethoxide, potassium isopropoxide, potassium tert-butoxide, lithium methoxide, and potassium naphthalenide. Examples of the inorganic base include, for example, potassium carbonate, potassium hydroxide, lithium hydroxide, sodium hydrogencarbonate, sodium carbonate, potassium hydrogencarbonate, and sodium hydroxide.

The amount of the base used is appropriately selected usually from the range of 2 to 5 mmol, preferably from the range of 2 to 3 mmol per 1 mmol of the ruthenium complex.

The pressure of hydrogen used in the process for producing the optically active alcohol of the present invention is desirably at least 0.1 MPa, and is appropriately selected usually from the range of 0.5 to 10 MPa, preferably from the range of 1 to 5 MPa, considering economical efficiency or the like.

The reaction temperature is appropriately selected usually from the range of 15 to 100° C., preferably from the range of 20 to 80° C., considering economical efficiency or the like. The reaction can be conducted even if the reaction temperature is a low temperature of −30 to 0° C. or a high temperature of 100 to 250° C.

The reaction time is varied in accordance with the kind and the amount of the used asymmetric hydrogenation catalyst, the kind and the concentration of the used ketone compound, reaction conditions such as the reaction temperature and the pressure of hydrogen, and others. Usually, the reaction is completed usually in a time from several minutes to several tens of hours. The time is selected usually from the range of 1 minute to 48 hours, preferably from the range of 10 minutes to 24 hours.

A preferred example of the process for producing the optically active alcohol of the present invention is a process based on transfer hydrogenation.

It is preferred that a hydrogen donating material is present in situ. for an asymmetric hydrogenation by transfer hydrogenation. The hydrogen donating material is an organic compound and/or an inorganic compound and can be used any compound which is capable of donating hydrogen by, for example, thermal action or catalytic action in situ.

Examples of the hydrogen donating material include, for example, formic acid or salts thereof, a combination of formic acid with a base, hydroquinone, phosphorous acid, and alcohols. Of these, formic acid or salts thereof, a combination of formic acid with a base, and alcohols are particularly preferred.

Example of the salts of formic acid in formic acid or the salt thereof include metal salts of formic acid such as alkali metal salts and alkaline earth metal salts of formic acid, ammonium salts thereof, and substituted amine salts thereof.

Also, the combination of formic acid with the base may be a combination which turns into the form of a formic acid salt in situ, or a combination which substantially turns into the form of a formic acid salt.

The alkali metal, which forms a salt with formic acid include lithium, sodium, potassium, rubidium, and caesium. Also, the alkaline earth metal include magnesium, calcium, strontium, and barium.

The base which forms the metal salts of formic acid, such as the alkali metal salts of formic acid and the alkaline earth metal salts thereof, or which forms ammonium salts, substituted amine salts or the like, and the base in the combination of formic acid with the base include ammonia, an inorganic base, and an organic base.

The inorganic base include, for example, alkali or alkaline earth metal salts such as potassium carbonate, potassium hydroxide, lithium hydroxide, sodium hydrogencarbonate, sodium carbonate, potassium hydrogencarbonate, sodium hydroxide, magnesium carbonate, and calcium carbonate; and metal hydrides such as sodium hydride, sodium borohydride, and lithium aluminum hydride.

The organic base include, for example, alkali metal alkoxides such as potassium methoxide, sodium methoxide, lithium methoxide, sodium ethoxide, potassium isopropoxide, potassium tert-butoxide, and potassium naphthalenide; acetic acid salts of an alkali or alkaline earth metal such as sodium acetate, potassium acetate, magnesium acetate, and calcium acetate; organic amines such as triethylamine, diisopropylethylamine, N,N-dimethylaniline, piperidine, pyridine, 4-dimethylaminopyridine, 1,5-diazabicyclo[4.3.0]non-5-ene, 1,8-diazabicyclo[5.4.0]undec-7-ene, tri-n-butylamine, and N-methylmorpholine; organic metal compounds such as magnesium methylbromide, magnesium ethylbromide, magnesium propylbromide, methyllithium, ethyllithium, propyllithium, n-butyllithium, and tert-butyllithium; and quaternary ammonium salts.

The alcohol as the hydrogen donating material is preferably a lower alcohol having a hydrogen atom at its α-position. Specific examples thereof include, for example, methanol, ethanol, n-propanol, isopropanol, n-butanol, and sec-butanol. Of these, isopropanol is preferred.

The amount of the hydrogen donating material used is appropriately selected usually from the range of 2 to 20 equivalents, preferably from the range of 4 to 10 equivalents of the ketone compound.

These processes for producing the optically active alcohol of the present invention can be carried out whether the reaction system therefor is of a batch type or of a continuous type.

EFFECTS OF THE INVENTION

The present invention provides a novel transition metal complex which can be effectively used for various asymmetric synthesis and in particular which can be more effectively used for asymmetric hydrogenation of various ketones; and a novel process for producing an optically active alcohol by using thereof. When the ruthenium phosphine complex of the present invention, in particular, the optically active ruthenium phosphine diamine complex thereof or the optically active rhodium phosphine diamine complex thereof is used to conduct hydrogenation of a ketone compound, an optically active alcohol can be obtained in a high optical purity and a high yield. Thus, the present invention is attained to a high asymmetric yield in the same manner as when an optically pure catalyst is used.

Furthermore, the transition metal complex which is useful as an asymmetric catalyst of the present invention can be produced by using an achiral phosphine, and the present invention provides a process which is very profitable for industry.

BEST MODE FOR CARRYING OUT THE INVENTION

The present invention will be more specifically described by way of the following examples. However, the invention is not limited to these examples at all.

In Examples and Reference Examples which will be described below, devices used to measure physical properties or the like are as follows:

$^1$H nuclear magnetic resonance spectra (hereinafter abbreviated to $^1$H-NMR): GEMINI 300 model (300 MHz) (manufactured by Varian Co.)

$^{13}$C nuclear magnetic resonance spectra (hereinafter abbreviated to $^{13}$C-NMR): GEMINI 300 model (75 MHz) (manufactured by Varian Co.)

Infrared absorption spectra (hereinafter abbreviated to IR): FT/IR-5000 (manufactured by JASCO Corp.)

Optical rotation meter: DIP-140 model (manufactured by JASCO Corp.)

High-performance liquid chromatography (hereinafter abbreviated to HPLC): LC-6A, and SPD-6A (manufactured by Shimadzu Corp.)

Symbols and abbreviations used in Examples and Reference Examples are as follows:

DMF: dimethylformamide

Ph: phenyl group

Ar: 3,5-dimethylphenyl group

DPEN (dpen): diphenylethylenediamine

DPBP:

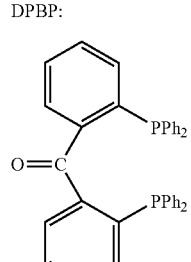

DPEphos:

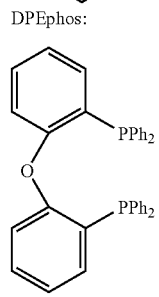

DPBOL:

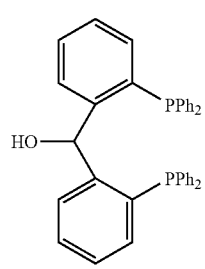

-continued

DM-BIPHEP:

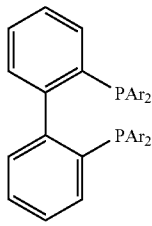

DM-BINAP:

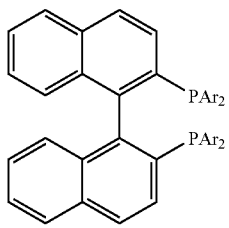

(S)-BINAP:

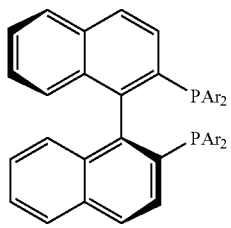

EXAMPLE 1

Synthesis of RuCl$_2${2,2'-bis(diphenylphosphinyl)benzophenone}{(S,S)-DPEN}

(1) Synthesis of 2,2'-bisfluorobenzhydrol

A mixed solution of 455 µl (4.2 mmol) of 2-bromofluorobenzene and 15 ml of tetrahydrofuran was cooled to −70° C. Thereto was added 2.8 ml (4.4 mmol) of n-butyllithium, and the resultant was stirred for 30 minutes while the temperature thereof was kept at −70° C. Thereafter, thereto was added 165 µL (2.0 mmol) of ethyl formate and the resultant was stirred at room temperature for 15 hours. To the reaction mixture was added 10 mL of water, and then the resultant mixture was extracted with methylene chloride 3 times. The organic phases were collected and washed with water, and then dried over magnesium sulfate. The resultant was concentrated to collect the solvent, and then the concentrate was purified by column chromatography on silica gel (ethyl acetate:hexane=1:5) to give 375 mg (yield: 85%) of the title compound in the form of a yellow solution.

$^1$H NMR (CDCl$_3$) δ ppm; 7.00-7.48 (8H, m), 6.42 (1H, s).

(2) Synthesis of 2,2'-bisfluorobenzophenone

To a mixture of 440.4 mg (2.0 mmol) of 2,2'-bisfluorobenzhydrol and 1.04 g (12.0 mmol) of activated manganese oxide was added 10 ml of benzene. The resultant was refluxed for 2 hours. The reaction mixture was cooled to room temperature, and filtrated with celite. The filtrate was concentrated and purified by column chromatography on silica gel (ethyl acetate:hexane=1:5) to give 360 mg (yield: 82%) of the title compound in the form of a yellow solution.

$^1$H NMR (CDCl$_3$) δ ppm; 7.07-7.37 (8H, m).
$^{19}$F NMR (CDCl$_3$) δ ppm; −112.70 (s).

(3) Synthesis of 2,2'-bis(diphenylphosphinyl)benzophenone

A mixed solution of 98.2 mg (0.45 mmol) of 2,2'-bisfluorobenzophenone and 5 ml of tetrahydrofuran was heated to 70° C. Thereafter, thereto was added 2.8 ml (1.4 mmol) of potassium diphenylphosphine, and the resultant was refluxed for 2.5 hours. Thereafter, the reaction mixed solution was cooled to 0° C., and several drops of 1N hydrochloric acid were added to the mixture. After the resultant solution was stirred for 1 to 2 minutes, magnesium sulfate was added thereto. The resultant was filtrated with celite. The filtrate was concentrated and then purified by column chromatography on silica gel (ethyl acetate:hexane=1:6) and column chromatography on alumina (ethyl acetate:hexane=1:6) to give 34 mg (yield: 13%) of the title compound in the form of a white solid.

$^1$H NMR (CDCl$_3$) δ ppm; 6.99-7.30 (28H, m).
$^{31}$P NMR (CDCl$_3$) δ ppm; −17.31 (s).

(4) Synthesis of RuCl$_2${2,2'-bis(diphenylphosphinyl)benzophenone}(DMF)$_n$

After 6.6 mg (0.012 mmol) of 2,2'-bis(diphenylphosphinyl)benzophenone, 3.0 mg (0.006 mmol) of benzene ruthenium chloride dimer, and 1 ml of DMF were stirred at 100° C. for 45 minutes, the solvent therein was distilled off under reduced pressure to give the title compound.

(5) Synthesis of RuCl$_2${2,2'-bis(diphenylphosphinyl)benzophenone}{(S,S)-DPEN}}

Into RuCl$_2${2,2'-bis(diphenylphosphinyl)benzophenone}(DMF)$_n$ obtained in the (4) after the distillation under reduced pressure were added 2.6 mg (0.012 mmol) of (S,S)-DPEN and 0.8 ml of methylene chloride. The resultant was stirred for 30 minutes. The solvent therein was distilled off under reduced pressure and then the residue was dried to give 11.2 mg (yield: >99%) of the title compound which was brownish-red.

$^{31}$P NMR (CDCl$_3$) δ ppm; −48.79 (d, 0.036 Hz), −49.45 (d, 0.036 Hz)

EXAMPLE 2

Synthesis of RuCl$_2${2-diphenylphosphinobenzhydrol}{(S,S)-DPEN}

(1) Synthesis of 2,2'-bis(trifluoromethanesulfonyloxy)benzophenone

Into 15 ml of methylene chloride were dissolved 856.9 mg (4.0 mmol) of 2,2'-dihydroxybenzophenone and 97.7 mg (0.8 mmol) of dimethylaminopyridine, and the solution was cooled to 0° C. Thereto was added 1.2 ml (10 mmol) of 2,6-lutidine, and then 1.7 mL (10 mmol) of trifluoromethanesulfonic acid anhydride was added dropwise thereto. Thereafter, the solution was stirred at room temperature for 18 hours. The reaction mixture was washed with water and brine, and then dried over magnesium sulfate. The solvent was distilled off under reduced pressure, and then the resultant was purified by column chromatography on alumina (ethyl acetate:hexane=1:4) to give 1.42 g (yield: 75%) of the title compound in the form of an orange liquid.

$^1$H NMR (CDCl$_3$) δ ppm; 7.39-7.70 (8H, m).
$^{19}$F NMR (CDCl$_3$) δ ppm; −73.75 (s).

(2) Synthesis of 2,2'-bis{diphenylphosphinyl}benzophenone

Into 5 ml of dimethylsulfoxide were dissolved 191.3 mg (0.4 mmol) of 2,2'-bis(trifluoromethanesulfonyloxy)benzophenone, 9.0 mg (0.04 mmol) of palladium acetate, 17.0 mg (0.04 mmol) of 1,4-bis(diphenylphosphino)butane, and 310 mg (1.2 mmol) of diphenylphosphine oxide, and further thereto was added 191.3 mg (0.4 mmol) of N,N-diisopropylethylamine. The resultant solution was stirred at 100° C. for 18 hours. The reaction mixture was cooled to room temperature, and 10 ml of methylene chloride was added thereto. This solution was washed with 1 N hydrochloric acid, water and brine in sequence, and then dried over magnesium sulfate. The solvent was distilled off under reduced pressure, and then the resultant was purified by column chromatography on silica gel (ethyl acetate-methylene chloride:methanol=10:1 to give 252 mg (yield: 90%) of the title compound in the form of a brownish-red solid.

$^1$H NMR (CDCl$_3$) δ ppm; 7.06-7.70 (28H, m).
$^{31}$P NMR (CDCl$_3$) δ ppm; 32.07 (s).

(3) Synthesis of 2-diphenylphosphinobenzhydrol

Into 10 ml of toluene was dissolved 252 mg (0.36 mmol) of 2,2'-bis{diphenylphosphinyl}benzophenone, and further 2.0 ml (14.4 mmol) of triethylamine was added thereto. The resultant solution was cooled to 0° C. Thereto was added 360 μl (3.6 mmol) of trichlorosilane, and then the resultant solution was stirred for 30 minutes while the temperature thereof was kept at 0° C. Thereafter, the temperature thereof was slowly raised to a temperature at which the solution was allowed to be refluxed. The solution was then refluxed for 4 hours. The reaction mixture was cooled, and thereto was added dropwise 10 ml of 25% aqueous sodium hydroxide slowly. The aqueous phase was extracted with 10 ml of methylene chloride. The organic phases were combined, and the resultant was washed with 1N hydrochloric acid two times and then dried over magnesium sulfate. The resultant was concentrated under reduced pressure to distill off the solvent, and then purified by column chromatography on silica gel (ethyl acetate:hexane=1:6 to give 47.7 mg (yield: 20%) of the title compound in the form of a yellow solid.

$^1$H NMR (CDCl$_3$) δ ppm; 6.91-7.39 (28H, m).
$^{31}$P NMR (CDCl$_3$) δ ppm; −17.41 (s).

(4) Synthesis of RuCl$_2${2-diphenylphosphinobenzhydrol}(DMF)$_n$

At 100° C., 6.6 mg (0.012 mmol) of 2-diphenylphosphinobenzhydrol, 3.0 mg (0.006 mmol) of benzene ruthenium chloride dimer, and 1 ml of DMF were stirred for 45 minutes, and then the solvent was distilled off under reduced pressure to give the title compound.

(5) Synthesis of RuCl$_2${2-diphenylphosphinobenzhydrol}{(S,S)-DPEN}

Into RuCl$_2${2-diphenylphosphinobenzhydrol}(DMF)$_n$ obtained in the (4) after the distillation under reduced pressure were added 2.6 mg (0.012 mmol) of (S,S)-DPEN and 0.8 ml of methylene chloride, and then the resultant was stirred for 30 minutes. The solvent was distilled off under reduced pressure and then the residue was dried to give 11.2 mg (yield: >99%) of the title compound.
$^{31}$P NMR (CDCl$_3$) δ ppm; 48.62, 49.25 (2d, J$_{P-P}$=32.07 Hz).

EXAMPLE 3

Synthesis of 2,2'-bis{di-(3,5-xylyl)phosphino}benzophenone (1) Synthesis of 2,2'-bis(trifluoromethanesulfonyloxy)benzophenone Into 15 ml of methylene chloride were dissolved 856.9 mg (4.0 mmol) of 2,2'-dihydroxybenzophenone and 97.7 mg (0.8 mmol) of dimethylaminopyridine, and the solution was cooled to 0° C. After thereto was added 1.2 ml (10 mmol) of 2,6-lutidine, 1.7 ml (10 mmol) of trifluoromethanesulfonic acid anhydride was added dropwise thereto. Thereafter, the solution was stirred at room temperature for 18 hours. The reaction mixture was washed with water and brine, and then dried over magnesium sulfate. The solvent was distilled off under reduced pressure, and then the resultant was purified by column chromatography on alumina (ethyl acetate:hexane=1:4) to give 1.42 g (yield: 75%) of the title compound in the form of an orange liquid.

$^1$H NMR (CDCl$_3$) δ ppm; 7.39-7.70 (8H, m).
$^{19}$F NMR (CDCl$_3$) δ ppm; −73.75 (s).

(2) Synthesis of 2,2'-bis{di-(3,5-xylyl)phosphino}benzophenone

Into 5 ml of dimethylsulfoxide were dissolved 191.3 mg (0.4 mmol) of 2,2'-bis(trifluoromethanesulfonyloxy)benzophenone, 9.0 mg (0.04 mmol) of palladium acetate, 17.0 mg (0.04 mmol) of 1,4-bis(diphenylphosphino)butane, and 310 mg (1.2 mmol) of di-(3,5-xylyl)phosphine oxide, and further thereto was added 191.3 mg (0.4 mmol) of N,N-diisopropylethylamine. The resultant solution was stirred at 100° C. for 18 hours. The reaction mixture was cooled to room temperature, and 10 ml of methylene chloride was added thereto. This solution was washed with 1N hydrochloric acid, water and brine in sequence, and then dried over magnesium sulfate. The solvent was distilled off under reduced pressure, and then the resultant was purified by column chromatography on silica gel (ethyl acetate-methylene chloride:methanol=10:1 to give 252 mg (yield: 90%) of the title compound in the form of a brownish-red solid.

$^1$H NMR (CDCl$_3$) δ ppm; 2.22 (24H, s), 7.03-7.78 (20H, m).
$^{31}$P NMR (CDCl$_3$) δ ppm; 32.08 (s).

(3) Synthesis of 2,2'-bis{di-(3,5-xylyl)phosphino}benzophenone

Into 10 ml of toluene was dissolved 252 mg (0.36 mmol) of 2,2'-bis{di-(3,5-xylyl)phosphinyl}benzophenone, and further 2.0 ml (14.4 mmol) of triethylamine was added thereto, and the resultant solution was cooled to 0° C. Thereto was added 360 μl (3.6 mmol) of trichlorosilane, and then the resultant solution was stirred for 30 minutes while the temperature thereof was kept at 0° C. Thereafter, the temperature thereof was slowly raised to a temperature at which the solution was allowed to be refluxed. The solution was then refluxed for 4 hours. The reaction mixture was cooled, and thereto was dropwise added 10 ml of 25% aqueous sodium hydroxide slowly. The aqueous phase was extracted with 10 ml of methylene chloride. The organic phases were combined, washed with 1N hydrochloric acid two times and then dried over magnesium sulfate. The resultant was concentrated under reduced pressure to distill off the solvent, and then purified by column chromatography on silica gel (ethyl acetate:hexane=1:6) to give 47.7 mg (yield: 20%) of the title compound in the form of a yellow solid.

$^1$H NMR (CDCl$_3$) δ ppm; 2.15 (12H, s), 2.23 (12H, s), 6.73-7.41 (20H, m).

$^{31}$P NMR (CDCl$_3$) δ ppm; −18.02 (s).

EXAMPLE 4

Synthesis of RuCl$_2$ {bis(2-diphenylphosphinophenyl) ether}{(S,S)-DPEN}

(1) Synthesis of RuCl$_2$ {bis(2-diphenylphosphinophenyl)ether}(DMF)$_n$

At 100° C., 6.4 mg (0.012 mmol) of bis(2-diphenylphosphinophenyl)ether, 3.0 mg (0.006 mmol) of benzene ruthenium chloride dimer, and 1 ml of DMF were stirred for 30 minutes, and then the solvent was distilled off under reduced pressure to give the title compound.

(2) Synthesis of RuCl$_2$ {bis(2-diphenylphosphinophenyl)ether}{(S,S)-DPEN}

Into RuCl$_2$ {bis(2-diphenylphosphinophenyl)ether}(DMF)$_n$ obtained in the (1) after the distillation under reduced pressure were added 2.6 mg (0.012 mmol) of (S,S)-DPEN and 0.8 ml of methylene chloride, and then the resultant was stirred for 30 minutes. The solvent was distilled off under reduced pressure and then the residue was dried to give 11.1 mg (yield: >99%) of the title compound which was brownish-red.

$^{31}$P NMR (CDCl$_3$) δ ppm; 43.09 (s).

Meanwhile, the bis(2-diphenylphosphinophenyl)ether as the starting material was purchased from STREM CHEMICALS Co. and used.

EXAMPLE 5

Asymmetric Hydrogenation of 2'-Methylacetophenone

Under a nitrogen atmosphere, RuCl$_2$(DPBOL)(DMF)n (0.4% by mol) obtained in the (4) of Example 2, (S,S)-DPEN (0.4% by mol), 402.5 g (3.0 mmol) of 2'-methylacetophenone, 1.3 mg (0.8% by mol) of potassium hydroxide, and 3.3 mL of 2-propanol were placed in an autoclave made of stainless steel, and the mixture were caused to react by stirring at room temperature under hydrogen pressure of 0.8 MPa (8 atm) for 4 hours to give (1R)-1-(2-methylphenyl)-ethanol. GC yield: not less than 99%. Optical purity: 96% ee.

EXAMPLE 6

Asymmetric Hydrogenation of 2'-Methylacetophenone

The reaction was carried out in the same way as in Example 5 except that RuCl$_2$(DM-BIPHEP)(DMF)$_n$ was used instead of RuCl$_2$(DPBOL)(DMF)$_n$ and the reaction temperature was set to 0° C. in Example 5 to give (1R)-1-(2-methylphenyl)-ethanol. GC yield: not less than 99%. Optical purity: 88% ee.

EXAMPLE 7

Asymmetric Hydrogenation of 2'-Methylacetophenone

The reaction was carried out in the same way as in Example 5 except that RuCl$_2$(DM-BINAP)(DMF)n was used instead of RuCl$_2$(DPBOL)(DMF)n and the reaction temperature was set to 0° C. in Example 5 to give (1R)-1-(2-methylphenyl)-ethanol. GC yield: not less than 99%. Optical purity: 86% ee.

EXAMPLE 8

Asymmetric Hydrogenation of Acetophenone

The reaction was carried out in the same way as in Example 5 except that acetophenone was used instead of 2'-methylacetophenone in Example 5 to give (1R)-1-phenylethanol. GC yield: not less than 99%. Optical purity: 91% ee.

EXAMPLE 9

Asymmetric Hydrogenation of Acetophenone

The reaction was carried out in the same way as in Example 8 except that RuCl$_2$(S)-BINAP)(DMF)$_n$ was used instead of RuCl$_2$(DPBOL)(DMF)$_n$ in Example 8 to give (1R)-1-phenylethanol. GC yield: not less than 99%. Optical purity: 87% ee.

TABLE 1

| Example | Diphosphine | Ketones | Products | GC Yield/% | Optical Purity/% ee |
|---------|-------------|---------|----------|------------|---------------------|
| 5 | DPBOL | | | >99 | 96(R) |
| 6 | DM-BIPHEP | | | >99 | 88(R) |
| 7 | DM-BINAP | | | >99 | 86(R) |
| 8 | DPBOL | | | >99 | 91(R) |
| 9 | (S)-BINAP | | | >99 | 87(R) |

EXAMPLE 10

Asymmetric Hydrogenation of 3'-Methylacetophenone

The reaction was carried out in the same way as in Example 5 except that 3'-methylacetophenone was used instead of 2'-methylacetophenone in Example 5 to give (1R)-(3-methylphenyl)ethanol. GC yield: 34%. Optical purity: 93% ee.

EXAMPLE 11

Asymmetric Hydrogenation of Methyl 2'-Naphthyl Ketone

The reaction was carried out in the same way as in Example 5 except that methyl 2'-naphthyl ketone was used instead of 2'-methylacetophenone in Example 5 to give (R)-1-(2-methylphenyl)ethanol. GC yield: not less than 99%. Optical purity: 82% ee.

EXAMPLE 12

Asymmetric Hydrogenation of 2'-Methylacetophenone

The reaction was carried out in the same way as in Example 5 except that $RuCl_2(DPEphos)(DMF)_n$ was used instead of $RuCl_2(DPBOL)(DMF)_n$ in Example 5 to give (1R)-1-(2-methylphenyl)ethanol. GC yield: not less than 99%. Optical purity: 41% ee.

EXAMPLE 13

Asymmetric Hydrogenation of Acetophenone

Into a pressure-resistant vessel was placed 11.1 mg (0.012 mmol) of $RuCl_2(DPEphos)\{(S,S)\text{-}DPEN\}$ synthesized in Example 4, and then thereto were added 48 µl (0.024 mmol) of a 0.5M solution of potassium hydroxide in 2-propanol and 3.3 ml of 2-propanol. Under an argon atmosphere, the solution was stirred for 30 minutes. Thereafter, 350 µl (3.0 mmol) of acetophenone was added thereto, and then the solution was stirred under hydrogen atmosphere of 0.8 MPa (8 atm) for 4 hours to give (1R)-1-phenylethanol, which is an alcohol reductant of acetophenone, in a GC yield of not less than 99% and an asymmetric yield of 91% ee.

EXAMPLE 14

Asymmetric Hydrogenation

The reaction was carried out in the same way as in Example 6 except that $RuCl_2(DPBP)(DMF)n$ was used instead of $RuCl_2(DPBOL)(DMF)n$ in Example 8 to give (1R)-1-phenylethanol. GC yield: 96%. Optical purity: 90% ee.

EXAMPLES 15 TO 19

Asymmetric Hydrogenation

The reaction was carried out in the same way as in Example 11 except that each ketone shown in the following Table 2 was used instead of acetophenone in Example 14. The results are shown in Table 2.

TABLE 2

| Example | Ketones | Products | GC Yield/ % | Optical Purity/ % ee |
|---|---|---|---|---|
| 14 | acetophenone | 1-phenylethanol | 96 | 90(R) |
| 15 | 2'-methylacetophenone | 1-(2-methylphenyl)ethanol | >99 | 98(R) |
| 16 | 3'-methylacetophenone | 1-(3-methylphenyl)ethanol | 61 | 89(R) |
| 17 | 4'-methylacetophenone | 1-(4-methylphenyl)ethanol | 68 | 90(R) |

TABLE 2-continued

| Example | Ketones | Products | GC Yield/ % | Optical Purity/ % ee |
|---|---|---|---|---|
| 18 | (1-acetylnaphthalene) | (1-(1-naphthyl)ethanol) | 85 | 98(R) |
| 19 | (di-2-naphthyl ketone derivative) | (corresponding alcohol) | 43 | 67(R) |

EXAMPLES 20 TO 23

Asymmetric Hydrogenation

The reaction was carried out in the same way as in Example 11 except that each ketone shown in the following Table 3 was used instead of 2'-methylacetophenone and the hydrogen pressure was changed in Example 14 to give an alcohol described in the column of "Products" in Table 3. The results are shown in Table 3.

TABLE 3

| Example | Ketones | Products | $H_2$ pressure/ MPa(atm) | GC Yield/ % | Optical Purity/ % ee |
|---|---|---|---|---|---|
| 20 | (4'-methylacetophenone) | (1-(4-methylphenyl)ethanol) | 1.5(15) | >99 | 91(R) |
| 21 | (1-acetylnaphthalene) | (1-(1-naphthyl)ethanol) | 2.0(20) | >99 | 99(R) |
| 22 | (di-naphthyl ketone) | (corresponding alcohol) | 1.5(15) | >99 | 82(R) |
| 23 | (3'-methylacetophenone) | (1-(3-methylphenyl)ethanol) | 1.5(15) | 99 | 92(R) |

EXAMPLE 24

Synthesis of Rh$^+${2,2'-bis(diphenylphosphinyl)benzophenone}{(S,S)-DPEN}(SbF$_6^-$)

(1) Synthesis of [Rh$^+${2,2'-bis(diphenylphosphinyl)benzophenone}(cod)](SbF$_6^-$)

Into 3 ml of methylene chloride were dissolved 55.0 mg (0.1 mmol) of 2,2'-bis(diphenylphosphinyl)benzophenone, and 52.3 mg (0.1 mmol) of [Rh(cod)$_2$]SbF$_6$, and then the solution was stirred at 25° C. for 3 hours. Thereafter, the solvent was distilled off under reduced pressure to give the title compound.

(2) Synthesis of Rh$^+${2,2'-bis(diphenylphosphinyl)benzophenone}{(S,S)-DPEN}(SbF$_6^-$)

Into [Rh$^+${2,2'-bis(diphenylphosphinyl)benzophenone}(cod)](SbF$_6^-$) obtained in the (1) after the distillation under reduced pressure were added 21.2 mg (0.1 mmol) of (S,S)-DPEN and 2 ml of methylene chloride, and then the solution was stirred under hydrogen atmosphere for 1 hour. The solvent was distilled off under reduced pressure and then the residue was dried to give 110 mg (yield: >99%) of the title compound.

$^{31}$P NMR (CDCl$_3$) δ ppm; 48.28, 57.04 (2dd, J$_{P-P}$=40.5 Hz$_o$, J$_{P-Rh}$=157.9 Hz$_o$).

EXAMPLE 25

Asymmetric Reduction Based on Transfer Hydrogenation

Under a nitrogen atmosphere, Rh$^+$(DPBP){(S,S)-DPEN}(SbF$_6^-$) (3% by mol) obtained in Example 18, 36.6 mg (0.3 mmol) of acetophenone, 6.7 mg (18% by mol) of potassium tert-butoxide, 3.6 mL of 2-propanol, and two or three drops of methylene chloride were placed in an autoclave made of stainless steel, and the mixture were caused to react by stirring at 60° C. for 24 hours to give (1R)-phenethyl alcohol. GC yield: not less than 99%.

Optical purity: 68% ee.

EXAMPLE 26 TO 29

Asymmetric Reduction Based on Transfer Hydrogenation

The reaction was carried out in the same way as in Example 25 except that each ketone shown in the following Table 4 was used instead of acetophenone in Example 25. The results are shown in Table 4.

TABLE 4

| Example | Ketones | Products | GC Yield/ % | Optical Purity/ % ee |
|---|---|---|---|---|
| 25 | phenyl methyl ketone | 1-phenylethanol | 99 | 68(R) |
| 26 | 2-methylphenyl methyl ketone | 1-(2-methylphenyl)ethanol | >99 | 95(R) |
| 27 | 3-methylphenyl methyl ketone | 1-(3-methylphenyl)ethanol | 97 | 73(R) |
| 28 | 4-methylphenyl methyl ketone | 1-(4-methylphenyl)ethanol | 95 | 62(R) |
| 29 | 1-naphthyl methyl ketone | 1-(1-naphthyl)ethanol | >99 | 95(R) |

EXAMPLE 30

Asymmetric Reduction Based on Transfer Hydrogenation

Under a nitrogen atmosphere, Rh$^+$(DPBP){(S,S)-DPEN}(SbF$_6^-$) (3% by mol) obtained in Example 18, 36.6 mg (0.3 mmol) of acetophenone, 6.7 mg (18% by mol) of potassium tert-butoxide, 3.6 mL of 2-propanol, and 0.4 mL of dichloroethane were placed in an autoclave made of stainless steel, and the mixture were caused to react by stirring at 60° C. for 24 hours to give (1R)-phenethyl alcohol. GC yield: not less than 87%. Optical purity: 87% ee.

EXAMPLE 31 TO 34

Asymmetric Reduction Based on Transfer Hydrogenation

The reaction was carried out in the same way as in Example 30 except that each ketone shown in the following Table 5 was used instead of acetophenone in Example 30. The results are shown in Table 5.

INDUSTRIAL APPLICABILITY

The present invention provides a novel transition metal complex, preferably an optically active transition metal complex, more preferably a ruthenium complex or rhodium complex which is useful as an asymmetric catalyst giving an excellent optical yield. The complex is used as a catalyst to make it possible to produce an industrially useful alcohol stereoselectively at a high yield.

Accordingly, the metal complex of the present invention and an asymmetric catalyst made thereof are each very useful for producing a stereoselective organic compound, and each have industrial applicability.

The invention claimed is:
1. A transition metal complex represented by the following formula [1]:

$$[LMX_pZ^1{}_n] \quad\quad [1]$$

wherein L represents a compound represented by the formula [2]:

TABLE 5

| Example | Ketones | Products | GC Yield/ % | Optical Purity/ % ee |
|---|---|---|---|---|
| 30 |  acetophenone | 1-phenylethanol | 95 | 87(R) |
| 31 | 2'-methylacetophenone | 1-(2-methylphenyl)ethanol | 51 | 96(R) |
| 32 | 3'-methylacetophenone | 1-(3-methylphenyl)ethanol | 70 | 90(R) |
| 33 | 4'-methylacetophenone | 1-(4-methylphenyl)ethanol | 77 | 82(R) |
| 34 | 1'-acetonaphthone | 1-(1-naphthyl)ethanol | 75 | 96(R) |

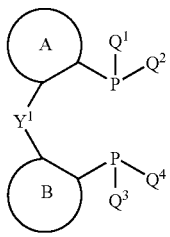

[2]

wherein ring A and ring B each independently represent an aromatic ring which may have a substituent, $Q^1$, $Q^2$, $Q^3$, and $Q^4$ each independently represent an aryl group which may have a substituent or an alicyclic group which may have a substituent, and $Y^1$ represents a spacer; M represents a transition metal; X represents a halogen atom or an anion; $Z^1$ represents a compound represented by the formula [3]:

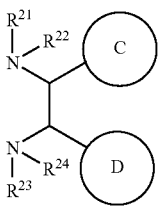

[3]

wherein ring C and ring D each independently represent a phenyl group which may have a substituent or an alicyclic group which may have a substituent, and $R^{21}$, $R^{22}$, $R^{23}$, and $R^{24}$ each independently represent a hydrogen atom or an alkyl group; p represents 1 or 2; and n is a natural number.

2. The transition metal complex according to claim 1, wherein $Y^1$ in the compound represented by the formula [2] is a carbonyl group, a sulfonyl group, a thiocarbonyl group, —CH(OH)— or —CH(SH)—.

3. The transition metal complex according to claim 1, wherein the compound represented by the formula [3] is an optically active compound, and the transition metal complex is an asymmetric transition metal complex.

4. The transition metal complex according to claim 1, wherein the transition metal of the complex is selected from the Groups VIII to X of the periodic table of the element.

5. The transition metal complex according to claim 1, wherein the transition metal of the complex is ruthenium or rhodium.

6. The transition metal complex according to claim 5, wherein the complex is an optically active ruthenium phosphine diamine complex represented by the following formula [1-1a]:

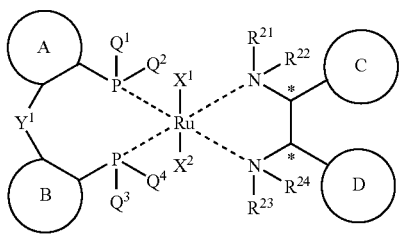

[1-1a]

wherein ring A and ring B each independently represent an aromatic ring which may have a substituent, $Q^1$, $Q^2$, $Q^3$, and $Q^4$ each independently represent an aryl group which may have a substituent, or an alicyclic group which may have a substituent, $Y^1$ represents a spacer selected from a carbonyl group, a sulfonyl group, a thiocarbonyl group, —CH(OH)— or —CH(SH)—, $X^1$ and $X^2$ each independently represent a halogen atom, ring C and ring D each independently represent a phenyl group which may have a substituent or an alicyclic group which may have a substituent, $R^{21}$, $R^{22}$, $R^{23}$, and $R^{24}$ each independently represent a hydrogen atom or an alkyl group, and * represents asymmetric carbon atom.

7. A rhodium phosphine complex represented by the following formula [1-2a]:

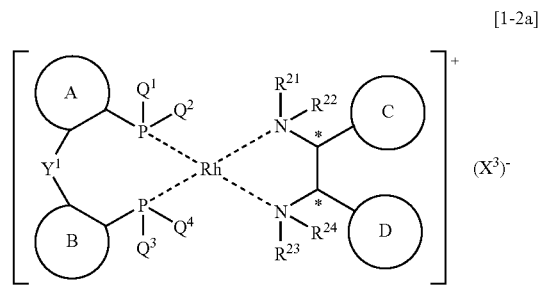

[1-2a]

wherein ring A and ring B each independently represent an aromatic ring which may have a substituent, $Q^1$, $Q^2$, $Q^3$, and $Q^4$ each independently represent an aryl group which may have a substituent, or an alicyclic group which may have a substituent, $Y^1$ represents a spacer selected from a carbonyl group, a sulfonyl group, a thiocarbonyl group, —CH(OH)— or —CH(SH)—, ring C and ring D each independently represent a phenyl group which may have a substituent or an alicyclic group which may have a substituent, $R^{21}$, $R^{22}$, $R^{23}$, and $R^{24}$ each independently represent a hydrogen atom or an alkyl group, $(X^3)^-$ represents an anion, and * represents asymmetric carbon atom.

8. An asymmetric catalyst comprising at least one transition metal complex according to claim 3.

9. An asymmetric catalyst comprising a transition metal compound represented by the formula [4]:

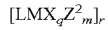

$[LMX_qZ^2_m]_r$      [4]

wherein L represents a compound represented by the formula [2]:

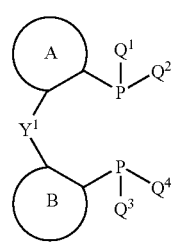

[2]

wherein ring A and ring B each independently represent an aromatic ring which may have a substituent, $Q^1$, $Q^2$, $Q^3$, and $Q^4$ each independently represent an aryl group which may have a substituent or an alicyclic group which may have a substituent, and $Y^1$ represents a spacer; M represents a transition metal; X represents a halogen atom or an anion; $Z^2$ represents a neutral ligand; q represents 1 or 2; r represents 1 or 2; and m is 0 or a natural number;

and an optically active compound represented by the formula [3a]:

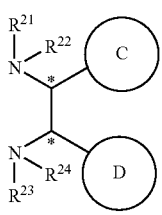

[3a]

wherein ring C and ring D each independently represent a phenyl group which may have a substituent or an alicyclic group which may have a substituent, $R^{21}$, $R^{22}$, $R^{23}$, and $R^{24}$ each independently represent a hydrogen atom or an alkyl group, and * represents asymmetric carbon atom.

10. The asymmetric catalyst according to claim 8, wherein the asymmetric catalyst is an asymmetric hydrogenation catalyst.

11. A compound represented by the following formula [2']:

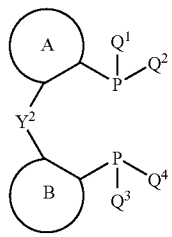

[2']

wherein ring A and ring B each independently represent an aromatic ring which may have a substituent, $Q^1$, $Q^2$, $Q^3$, and $Q^4$ each independently represent an aryl group which may have a substituent or an alicyclic group which may have a substituent, and $Y^2$ represents a carbonyl group (C=O), a sulfonyl group ($SO_2$), a thiocarbonyl group (C=S), —CH(OH)— or —CH(SH)—.

12. A process for producing an optically active alcohol represented by the following formula [12]:

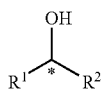

[12]

wherein $R^1$ and $R^2$ each independently represent a hydrocarbon group which may have a substituent, an aliphatic heterocyclic group which may have a substituent, or an aromatic heterocyclic group which may have a substituent (provided that a case where $R^1$ and $R^2$ are equal to each other is excluded), and $R^1$ and $R^2$ may be bonded to each other so as to form a ring together with the adjacent carbon atom, thereby forming a ring which may have a substituent, * represents asymmetric carbon atom, which comprises reacting with a ketone compound represented by the following formula [11]:

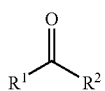

[11]

wherein $R^1$ and $R^2$ have the same meanings as described above, in the presence of the asymmetric catalyst according to claim 9 by asymmetric hydrogenation.

* * * * *